United States Patent
Rodino-Klapac et al.

(10) Patent No.: US 12,377,170 B2
(45) Date of Patent: Aug. 5, 2025

(54) ADENO-ASSOCIATED VIRUS VECTOR DELIVERY OF β-SARCOGLYCAN AND THE TREATMENT OF MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, Columbus, OH (US); Jerry R. Mendell, Columbus, OH (US)

(73) Assignee: Research Institute at Nationwide Children's Hospital, Columbus, OH (US)

(*) Notice: Subject to any disclaimer, the term of this patent is extended or adjusted under 35 U.S.C. 154(b) by 170 days.

(21) Appl. No.: 17/432,417

(22) PCT Filed: Feb. 26, 2020

(86) PCT No.: PCT/US2020/019892
§ 371 (c)(1),
(2) Date: Aug. 19, 2021

(87) PCT Pub. No.: WO2020/176614
PCT Pub. Date: Sep. 3, 2020

(65) Prior Publication Data
US 2023/0241252 A1    Aug. 3, 2023

Related U.S. Application Data

(60) Provisional application No. 62/910,779, filed on Oct. 4, 2019, provisional application No. 62/909,564, filed on Oct. 2, 2019, provisional application No. 62/881,901, filed on Aug. 1, 2019, provisional application No. 62/858,644, filed on Jun. 7, 2019, provisional application No. 62/834,012, filed on Apr. 15, 2019, provisional application No. 62/810,917, filed on Feb. 26, 2019.

(51) Int. Cl.
*A61K 48/00* (2006.01)
*A61K 38/17* (2006.01)
*A61P 21/00* (2006.01)
*C12N 15/86* (2006.01)

(52) U.S. Cl.
CPC ...... *A61K 48/0075* (2013.01); *A61K 38/1719* (2013.01); *A61K 48/0041* (2013.01); *A61K 48/0083* (2013.01); *A61P 21/00* (2018.01); *C12N 15/86* (2013.01); *C12N 2750/14042* (2013.01); *C12N 2750/14071* (2013.01)

(58) Field of Classification Search
CPC ............ A61K 48/0075; A61K 38/1719; A61K 48/0041; A61K 48/0083; A61P 21/00; C12N 15/86; C12N 2750/14042; C12N 2750/14071
See application file for complete search history.

(56) References Cited

U.S. PATENT DOCUMENTS

| | | |
|---|---|---|
| 5,173,414 A | 12/1992 | Lebkowski et al. |
| 5,449,616 A | 9/1995 | Campbell et al. |
| 5,658,776 A | 8/1997 | Flotte et al. |
| 5,672,694 A | 9/1997 | Campbell et al. |
| 5,786,211 A | 7/1998 | Johnson |
| 5,871,982 A | 2/1999 | Wilson et al. |
| 6,008,036 A | 12/1999 | Fanget et al. |
| 6,204,059 B1 | 3/2001 | Samulski et al. |
| 6,258,595 B1 | 7/2001 | Gao et al. |
| 6,262,035 B1 | 7/2001 | Campbell et al. |
| 6,566,118 B1 | 5/2003 | Atkinson et al. |
| 6,632,800 B1 | 10/2003 | Russell et al. |
| 7,282,199 B2 | 10/2007 | Gao et al. |
| 7,759,314 B2 | 7/2010 | Fallon et al. |
| 7,790,449 B2 | 9/2010 | Gao et al. |
| 7,883,858 B2 | 2/2011 | Hood et al. |
| 9,061,059 B2 | 6/2015 | Chakraborty et al. |
| 9,434,928 B2 | 9/2016 | Mendell et al. |

(Continued)

FOREIGN PATENT DOCUMENTS

| | | |
|---|---|---|
| CN | 101896186 A | 11/2010 |
| CO | 20210000227 A2 | 1/2021 |

(Continued)

OTHER PUBLICATIONS

Monies, Dorota, et al. "A first-line diagnostic assay for limb-girdle muscular dystrophy and other myopathies." Human Genomics 10 (2016): 1-7. (Year: 2016).*
Theadom, Alice, et al. "Prevalence of muscular dystrophies: a systematic literature review." Neuroepidemiology 43.3-4 (2015): 259-268. (Year: 2015).*
Chu, Mary Lynn, and Ellen Moran. "The limb-girdle muscular dystrophies: is treatment on the horizon?." Neurotherapeutics 15.4 (2018): 849-862. (Year: 2018).*
Walter, Maggie C., and Peter Reilich. "Recent developments in Duchenne muscular dystrophy: facts and numbers." Journal of cachexia, sarcopenia and muscle 8.5 (2017): 681. (Year: 2017).*
Moore, Steven A., et al. "Limb-girdle muscular dystrophy in the United States." Journal of Neuropathology & Experimental Neurology 65.10 (2006): 995-1003. (Year: 2006).*

(Continued)

*Primary Examiner* — Jennifer Dunston
*Assistant Examiner* — Christina Tran
(74) *Attorney, Agent, or Firm* — Foley & Lardner LLP

(57) ABSTRACT

Described herein are methods of treating muscular dystrophy comprising administering a recombinant AAV (rAAV) scAAVrh74.MHCK7.hSGCB vector, methods of expressing beta-sarcoglycan gene in a patient, pharmaceutical compositions comprising the rAAV, and methods of generating the rAAV. The disclosed methods reduce fibrosis and improve muscle function by restoring B-sarcoglycan expression in muscle tissues. The disclosure further provides preclinical studies in animal models, and a clinical trial involving systemic delivery of the vector to patients, which shows significant improvements in muscle pathology, force production, and overall activity in treated subjects.

10 Claims, 17 Drawing Sheets

Specification includes a Sequence Listing.

(56) References Cited

U.S. PATENT DOCUMENTS

| | | |
|---|---|---|
| 10,105,453 B2 | 10/2018 | Mendell et al. |
| 11,358,993 B2 | 6/2022 | Rodino-Klapac et al. |
| 2001/0029040 A1 | 10/2001 | Toyo-Oka |
| 2003/0225260 A1 | 12/2003 | Snyder |
| 2006/0154250 A1 | 7/2006 | Morris et al. |
| 2007/0099251 A1 | 5/2007 | Zhang et al. |
| 2008/0249052 A1 | 10/2008 | Duan et al. |
| 2009/0054823 A1 | 2/2009 | Bridges et al. |
| 2009/0275107 A1 | 11/2009 | Lock et al. |
| 2009/0280103 A1 | 11/2009 | Flueck |
| 2010/0003218 A1 | 1/2010 | Duan et al. |
| 2010/0008979 A1 | 1/2010 | Tomatsu et al. |
| 2010/0026655 A1 | 2/2010 | Harley |
| 2010/0075866 A1 | 3/2010 | Hood et al. |
| 2010/0112694 A1 | 5/2010 | Marban |
| 2010/0120627 A1 | 5/2010 | Belouchi et al. |
| 2010/0247495 A1 | 9/2010 | Ichim et al. |
| 2010/0266551 A1 | 10/2010 | Richard et al. |
| 2011/0023139 A1 | 1/2011 | Weinstein et al. |
| 2011/0053221 A1 | 3/2011 | Chen et al. |
| 2011/0070210 A1 | 3/2011 | Andrijauskas |
| 2011/0076744 A1 | 3/2011 | Wright et al. |
| 2011/0082192 A1 | 4/2011 | Milne et al. |
| 2011/0104120 A1 | 5/2011 | Xiao et al. |
| 2011/0266551 A1 | 11/2011 | Thompson et al. |
| 2011/0294193 A1 | 12/2011 | Amalfitano et al. |
| 2011/0301226 A1 | 12/2011 | Mendell et al. |
| 2012/0087862 A1 | 4/2012 | Hood et al. |
| 2013/0171172 A1 | 7/2013 | Richard et al. |
| 2014/0010861 A1 | 1/2014 | Bancel et al. |
| 2014/0147432 A1 | 5/2014 | Chakraborty et al. |
| 2014/0179770 A1 | 6/2014 | Zhang et al. |
| 2014/0234255 A1 | 8/2014 | Lai et al. |
| 2014/0249208 A1 | 9/2014 | Chakraborty et al. |
| 2014/0256802 A1 | 9/2014 | Boye et al. |
| 2014/0273231 A1 | 9/2014 | Zhang et al. |
| 2014/0323956 A1 | 10/2014 | Mendell et al. |
| 2015/0111955 A1 | 4/2015 | High et al. |
| 2015/0125429 A1 | 5/2015 | Perlingeiro et al. |
| 2015/0232883 A1 | 8/2015 | Dahlman et al. |
| 2015/0238627 A1 | 8/2015 | Leger et al. |
| 2016/0058890 A1 | 3/2016 | Buj Bello et al. |
| 2018/0256752 A1 | 9/2018 | Buj Bello et al. |
| 2019/0000998 A1 | 1/2019 | Mendell et al. |
| 2019/0202880 A1 | 7/2019 | Rodino-Klapac et al. |
| 2020/0339960 A1 | 10/2020 | Sahenk |
| 2021/0128749 A1 | 5/2021 | Rodino-Klapac et al. |
| 2021/0393801 A1 | 12/2021 | Rodino-Klapac et al. |
| 2023/0390417 A1 | 12/2023 | Sahenk |

FOREIGN PATENT DOCUMENTS

| | | |
|---|---|---|
| EP | 0 127 839 A2 | 12/1984 |
| EP | 0 155 476 A | 9/1985 |
| EP | 2 170 325 A | 4/2010 |
| EP | 2 859 896 A1 | 4/2015 |
| EP | 3 030 666 A | 6/2016 |
| JP | 2006-121961 A | 5/2006 |
| JP | 2015-509711 A | 4/2015 |
| JP | 2016-515831 A | 6/2016 |
| WO | 95/03392 A1 | 2/1995 |
| WO | 95/13365 A1 | 5/1995 |
| WO | 95/13392 A1 | 5/1995 |
| WO | 96/17947 A1 | 6/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |
| WO | 98/09657 A2 | 3/1998 |
| WO | 99/01176 A1 | 1/1999 |
| WO | 99/11764 A2 | 3/1999 |
| WO | WO-99/43360 A1 | 9/1999 |
| WO | 01/83692 A2 | 11/2001 |
| WO | 02/53703 A2 | 7/2002 |
| WO | WO-03/074714 A1 | 9/2003 |
| WO | 2004/058146 A2 | 7/2004 |
| WO | WO-2007/057781 A2 | 5/2007 |
| WO | WO-2009/019505 A2 | 2/2009 |
| WO | 2009/054725 A2 | 4/2009 |
| WO | 2013/016352 A1 | 1/2013 |
| WO | 2013/078316 A1 | 5/2013 |
| WO | WO-2013/123503 A1 | 8/2013 |
| WO | WO-2013/151665 A2 | 10/2013 |
| WO | WO-2013/176772 A1 | 11/2013 |
| WO | WO-2014/037526 A1 | 3/2014 |
| WO | WO-2014/039916 A1 | 3/2014 |
| WO | WO-2014/093622 A2 | 6/2014 |
| WO | WO-2014/093701 A1 | 6/2014 |
| WO | WO-2014/093712 A1 | 6/2014 |
| WO | WO-2014/204725 A1 | 12/2014 |
| WO | WO-2015/018503 A1 | 2/2015 |
| WO | WO-2015/021457 A2 | 2/2015 |
| WO | 2015/110449 A1 | 7/2015 |
| WO | WO-2015/158749 A2 | 10/2015 |
| WO | 2015/197232 A1 | 12/2015 |
| WO | WO-2016/115543 A2 | 7/2016 |
| WO | WO-2017/087395 A1 | 5/2017 |
| WO | WO-2017/165859 A1 | 9/2017 |
| WO | 2017/180857 A1 | 10/2017 |
| WO | 2017/180976 A1 | 10/2017 |
| WO | WO-2017/181014 A1 | 10/2017 |
| WO | WO-2017/181015 A1 | 10/2017 |
| WO | WO-2017/221145 A1 | 12/2017 |
| WO | WO-2018/170408 A1 | 9/2018 |
| WO | WO-2019/012336 A1 | 1/2019 |
| WO | WO-2019/078916 A1 | 4/2019 |
| WO | WO-2019/118806 A1 | 6/2019 |
| WO | WO-2019/152474 A1 | 8/2019 |
| WO | WO-2019/195362 A1 | 10/2019 |
| WO | WO-2019/209777 A1 | 10/2019 |
| WO | WO-2019/245973 A1 | 12/2019 |
| WO | WO-2020/006458 A1 | 1/2020 |
| WO | WO-2020/123645 A1 | 6/2020 |
| WO | WO-2021/035120 A1 | 2/2021 |
| WO | WO-2021/257655 A1 | 12/2021 |

OTHER PUBLICATIONS

Wagner, Anke, et al. "A novel method for the quantification of adeno-associated virus vectors for RNA interference applications using quantitative polymerase chain reaction and purified genomic adeno-associated virus DNA as a standard." Human Gene Therapy Methods 24.6 (2013): 355-363. (Year: 2013).*

McCarty, D. M. (2008). Self-complementary AAV vectors; advances and applications. Molecular therapy, 16(10), 1648-1656. (Year: 2008).*

Cordier et al., "Muscle-Specific Promoters May Be Necessary for Adeno-Associated Virus-Mediated Gene Transfer in the Treatment of Muscular Dystrophies," Human Gene Therapy, Jan. 20, 2001, vol. 12, pp. 205-215.

Cordier et al., "Rescue of Skeletal Muscles of gamma-Sarcoglycan-Deficient Mice with Adeno-Associated Virus-Mediated Gene Transfer," Molecular Therapy, Feb. 2000, vol. 1, No. 2 pp. 119-129.

Herson et al., A phase I trial of adeno-associated virus serotype 1-gamma-sarcoglycan gene therapy for limb girdle muscular type 2C, Brain, 2012, vol. 135, Pt 2, pp. 483-492.

McNally et al., "Mild and Severe Muscular Dystrophy Caused by a Single gamma-Sarcoglycan Mutation", American Journal of Human Genetics, Nov. 1996, vol. 59, No. 5, pp. 1040-1047.

NCBI, GenBank accession No. U34976.1 (Nov. 8, 1995), 2 pages.

Noguchi S, "Human gamma-sarcoglycan mRNA, complete cds.", NCBI, (Nov. 8, 1995), Database accession No. U34976, 2 pages.

Pozsgai et al., "506. [beta]—Sarcoglycan Gene Transfer Prevents Muscle Fibrosis and Inflammation in an Aged LGMD2E Mouse Model," Molecular Therapy, vol. 23 Supplement 1, May 2015, 2 pages.

Rose, comprehensive Virology 3:1-61 (1974).

Dorange et al., "Analytical approaches to characterize AAV vector production & purification: Advances and challenges," Cell & Gene Therapy Insights, 4(2):119-129 (2018).

(56) References Cited

OTHER PUBLICATIONS

Hou et al., "Serious Overestimation in Quantitative PCR by Circular (Supercoiled) Plasmid Standard: Microalgal pcna as the Model Gene," PLoS One 5(3):e9545, 8 pages (Mar. 5, 2010) doi:10.1371/journal.pone.0009545.

Martinez-Fernandez de la Camara et al., "The accurate quantification of AAV genomic titre depends on the conformation of the plasmid reference," ARVO Annual Meeting Abstract, 3 pages, Jul. 2018.

Wu et al., "Adeno-associated virus serotypes: vector toolkit for human gene therapy." Molecular therapy 14.3 (2006): 316-327 (Year: 2006).

Anderson et al., Nucleic Acid Hybridisation: A Practical Approach, IRL Press Limited, Oxford, England, Ch. 4 (1985).

Angelini et al., The clinical spectrum of sarcoglycanopathies. Neurology. 52:176-179 (1999).

Araishi et al., Loss of the sarcoglycan complex and sarcospan leads to muscular dystrophy in beta-sarcoglycan-deficient mice, Hum. Mol. Genet. 8: 1589-1598 (1999).

Barresi et al., Disruption of heart sarcoglycan complex and severe cardiomyopathy caused by beta sarcoglycan mutations, J. Med. Genet. 37: 102-107 (2000).

Beastrom et al., mdx(5cv) mice manifest more severe muscle dysfunction and diaphragm force deficits than do mdx Mice, Am. J. Pathol., 179(5):2464-74 (2011).

Bonnemann et al., Betasarcoglycan (A3b) mutations cause autosomal recessive muscular dystrophy with loss of the sarcoglycan complex, Nat. Genet., 11(3):266-273 (1995).

Bonnemann et al., Genomic screening for beta-sarcoglycan gene mutations: missense mutations may cause severe limb-girdle muscular dystrophy type 2E (LGMD 2E), Hum. Mol. Genet. 5:1953-1961 (1996).

Chao et al., Several log increase in therapeutic transgene delivery by distinct adeno-associated viral serotype vectors, Mol. Ther., 2(6):619-623 (2000).

Chao et al., Sustained and complete phenotype correction of hemophilia B mice following intramuscular injection of AAV1 serotype vectors, Mol. Ther., 4(3):217-222 (2001).

Chicoine et al., Plasmapheresis eliminates the negative impact of AAV antibodies on microdystrophin gene expression following vascular delivery, Mol. Ther., 22(2):338-347 (2014).

Chicoine et al., Vascular delivery of rAAVrh74.MCK.GALGT2 to the gastrocnemius muscle of the rhesus macaque stimulates the expression of dystrophin and laminin a2 surrogates. Mol. Ther. 22:713-724 (2014).

Chu et al., SV40 DNA transfection of cells in suspension: analysis of efficiency of transcription and translation of T-antigen, Gene., 13(2):197-202 (1981).

Clark et al., Highly purified recombinant adeno-associated virus vectors are biologically active and free of detectable helper and wild-type viruses, Hum. Gene Ther. 10:1031-1039 (1999).

Clark et al., Recombinant adeno-associated viral vectors mediate long-term transgene expression in muscle, Hum. Gene. Ther., 8(6):659-669 (1997).

Clark et at., A stable cell line carrying adenovirus-inducible rep and cap genes allows for infectivity titration of adeno-associated virus vectors, Gene. Ther. 3:1124-32 (1996).

Cserjesi et al., Myogenin induces the myocyte-specific enhancer binding factor MEF-2 independently of other muscle-specific gene products, Mol. Cell. Biol., 11(10):4854-4862 (1991).

De et al., High levels of persistent expression of alpha1-antitrypsin mediated by the nonhuman primate serotype rh.10 adeno-associated virus despite preexisting immunity to common human adeno-associated viruses, Mol. Ther. 13:67-76 (2006).

Draviam et al., The -li-core of sarcoglycan is essential for deposition at the plasma membrane, Muscle and Nerve. 34:691-701 (2006).

Dressman et al., Delivery of alpha- and beta-sarcoglycan by recombinant adeno-associated virus: efficient rescue of muscle, but differential toxicity, Hum. Gene. Ther., 13(13):1631-1646 (2002).

Dressman, D., AAV-Mediated gene transfer to models of muscular dystrophy: Insights into assembly of multi-subunit membrane proteins, University of Pittsburgh (1997).

Durbeej et al., Disruption of the beta-sarcoglycan gene reveals pathogenetic complexity of limb-girdle muscular dystrophy type 2E, Mol. Cell. 5:141-151 (2000).

Fanin et al., LGMD2E patients risk developing dilated cardiomyopathy, Neuromuscl. Disord., 13(4):303-309 (2003).

Flotte et al., Gene expression from adeno-associated virus vectors in airway epithelial cells, Am. J. Respir Mol. Biol. 7:349-356. 1992.

Gao et al., Clades of Adeno-associated Viruses are Widely Disseminated in Human Tissues, J. Virol., 78:6381-6388 (2004).

GenBank Accession No. AF085716.1, Adena-associated virus 5 DNA binding trs helicase (Rep22) and capsid protein (VP1) aenes, complete eds, Feb. 9, 1999.

GenBank Accession No. AX753246.1, Sequence 1 from Patent EP1310571, Jun. 23, 2003.

GenBank Accession No. AX753249.1, Sequence 4 from Patent EP1310571, Jun. 23, 2003.

Genbank Accession No. NC_001401.0, Adena-associated virus—2, complete genome, Aug. 13, 2018.

Genbank Accession No. NC_001729.1, Adena-associated virus—3, complete genome, Aug. 13, 2018.

GenBank Accession No. NC_001829.1, Adena-associated virus—4, complete genome, Aug. 13, 2018.

GenBank Accession No. NC_001862, Adena-associated virus 6, complete genome, Jan. 12, 2004.

Genbank Accession No. NC_002077.1, Adena-associated virus—1, complete genome, Aug. 13, 2018.

Genbank Accession No. NM_00232.4, *Homo sapiens* sarcoglycan beta (SGCB), MMA, Feb. 20, 2019.

Genbank Accession No. NP_000233.1, Beta Sarcoglyan (43kD dystrophin-associated glycoprotein) *Homo sapiens*, Mar. 19, 1999.

GenBank: Accession No. NP_000223.1: beta-sarcoglycan sequence, dated Mar. 3, 1999.

Gibertini et al., Fibrosis and inflammation are greater in muscles of beta-sarcoglycan-null mouse than mdx mouse, Cell Tissue Res. 356:427-443 (2014).

Graham et al., A new technique for the assay of infectivity of human adenovirus 5 DNA, Virology, 52(2):456-67 (1973).

Greig et al., Impact of intravenous infusion time on AAV8 vector pharmacokinetics, safety, and liver transduction in cynomolgus macaques, Mol. Ther. Methods Clin. Dev., 3(C):16079 (2016).

Grieger et al., Production and characterization of adeno-associated viral vectors, Nat. Protoc. 1:1412-1428 (2006).

Hakim et al., The passive mechanical properties of the extensor digitorum longus muscle are compromised in 2- to 20-mo-old mdx mice, J. Appl. Physiol. 110: 1656-1663 (2011).

Hermonat et al., Use of adeno-associated virus as a mammalian DNA cloning vector: transduction of neomycin resistance into mammalian tissue culture cells, Proc. Natl. Acad. Sci. USA. 81:6466-70 (1984).

Herzog et al., Stable gene transfer and expression of human blood coagulation factor IX after intramuscular injection of recombinant adeno-associated virus, Proc. Natl. Acad. Sci. USA, 94(11):5804-5809 (1997).

International Application No. PCT/US2017/027583, International Preliminary Report on Patentability, mailed Oct. 25, 2018.

International Application No. PCT/US2017/027583, International Search Report and Written Opinion, mailed Jul. 14, 2017.

International Application No. PCT/US2020/019892, International Preliminary Report on Patentability, mailed Sep. 10, 2021.

International Application No. PCT/US2020/019892, International Search Report and Written Opinion, mailed May 14, 2020.

International Preliminary Report on Patentability, PCT/US2017/027636 (Oct. 16, 2018).

International Search Report and Written Opinion, PCT/US2017/027636 (Jul. 5, 2017).

Johnson et al., Muscle creatine kinase sequence elements regulating skeletal and cardiac muscle expression in transgenic mice, Mol. Cell. Biol., 9(8):3393-3399 (1989).

(56) References Cited

OTHER PUBLICATIONS

Kessler et al., Gene delivery to skeletal muscle results in sustained expression and systemic delivery of a therapeutic protein, Proc. Nat. Acad. Sci. USA, 93(24):14082-14087 (1996).
Straub et al., Animal models for muscular dystrophy show different patterns of sarcolemmal disruption, J. Cell Biol. 139:375-385 (1997).
Sun et al., Correction of Multiple Striated Muscles in Murine Pompe Disease Through Adena-Associated Virus-mediated Gene Therapy, Mol. Ther., 16(8):1366-71 (2008).
Sveen et al., Cardiac involvement in patients with limb-girdle muscular dystrophy type 2 and Becker muscular dystrophy, Arch. Neurol., 65(9):1196-1201 (2008).
Tratschin et al., A human parvovirus, adeno-associated virus, as a eucaryotic vector: transient expression and encapsidation of the procaryotic gene for chloramphenicol acetyltransferase, Mol. Cell. Biol. 4:2072-81 (1984).
Tratschin et al., Adena-associated virus vector for high-frequency integration, expression, and rescue of qenes in mammalian cells, Mol. Cell. Biol. 5:3251-60 (1985).
Voikar et al., Long-term individual housing in C57BL/6J and DBA/2 mice: assessment of behavioral consequences, Genes Brain Behav., 4(4):240-52 (2005).
Wang et al., Construction and analysis of compact muscle-specific promoters for AAV vectors, Gene Ther. 15:1489-1499 (2008).
Wang et al., Loss of miR-29 in myoblasts contributes to dystrophic muscle pathogenesis, Mol. Ther., 20(6):1222-33 (2012).
Wein et al., Translation from a DMD exon 5 IRES results in a functional dystrophin isoform that attenuates dystrophinopathy in humans and mice, Nat. Med. 20: 992-1000 (2014).
Weintraub et al., The myoD gene family: nodal point during specification of the muscle cell lineage, Science. 251:761-766 (1991).
Wong-Kisiel et al., Two siblings with limb-girdle muscular dystrophy type 2E responsive to deflazacort, Neuromusc. Disord. 20:122-124 (2010).
Xiao et al., Efficient long-term gene transfer into muscle tissue of immunocompetent mice by adeno-associated virus vector, J. Virol., 70(11):8098-8108 (1996).
Xiao et al., Production of High-Titer Recombinant Adeno-Associated Virus Vectors in the Absence of Helper Adenovirus, J. Virol., 72:2224-2232 (1998).
Xu et al., An Isolated Limb Infusion Method Allows for Broad Distribution of rAAVrh74.MCK.GALGT2 to Leg Skeletal Muscles in the Rhesus Macaque, Mol. Ther. Methods Clin. Dev., 10:89-104 (2018).
Zanotti et al., Opposing roles of miR-21 and miR-29 in the progression of fibrosis in Duchenne muscular dystrophy., Biochem. Biophys. Acta., 1852:1451-4 (2015).
Zhang et al., Dual AAV therapy ameliorates exercise-induced muscle injury and functional ischemia in murine models of Duchenne muscular dystrophy, Hum. Mol. Genet. 22:3720-9 (2013).
Griffin et al. Preclinical systemic delivery of adeno-associated [alpha]-sarcoglycan gene transfer for limb-girdle mscular dystrophy, Human Gene Therapy, 32(7-8): 390-404, (Apr. 2021).
Inouye et al., Codon optimization of genes for efficient protein expression in mammalian cells by selection of only preferred human codons, Protein Expression and Purification, 109: 47-54, (May 2015).
Mendell et al., Sustained alpha-sarcoglycan gene expression after gene transfer in limb-girdle muscular dystrophy, type 2D, Annals of Neural. 68(5): 629-638, (Oct. 2010).
Raj Deepak et al., Self-complementary adeno-associated viral vectors for gene therapy of a hemophilia B: progress and challenges, Exert Review of Hemtol. England, Informa UK, 4(5): 539-549, (Nov. 2011).
Francois et al., Accurate titration of infectious AAV particles requires measurement of biologically active vector genomes and suitable controls, Mol. Ther., 10:223-236, (Sep. 2018).

Fowler, et al., Improved knockdown from artificial microRNAs in an enhanced miR-155 Backbone: a designer's guide to potent multi-target RNAi, Nucleic Acids Research, 44(5): e48, (Nov. 2015).
Kobayashi et al., Sarcolemma-localized nNOS is required to maintain activity after mild exercise, Nature. 456:511-5 (2008).
Kotin et al., Manufacturing Clinical Grade Recombinant Adena-Associated Virus Using Invertebrate Cell Lines, Hum. Gene Ther., 28(4):350-360 (2017).
Laughlin et al., Cloning of infectious adeno-associated virus genomes in bacterial plasmids, Gene. 23:65-73 (1983).
Laws et al., Progression of kyphosis in mdx mice, J. Appl. Physiol. 97:1970-7 (2004).
Lebkowski et al., Adena-associated virus: a vector system for efficient introduction and integration of DNA into a variety of mammalian cell types, Mol. Cell. Biol. 8:3988-96 (1988).
Lewis et al., Generation of neutralizing activity against human immunodeficiency virus type 1 in serum by antibody gene transfer, J. Virol., 76(17):8769-8775 (2002).
Liu et al., Adeno-associated virus-mediated microdystrophin expression protects young mdx muscle from contraction-induced injury, Mol. Ther., 11(2):245-256 (2005).
Mader et al., A steroid-inducible promoter for the controlled overexpression of cloned genes in eukaryotic cells, Proc. Natl. Acad. Sci. U.S.A., 90(12):5603-5607 (1993).
Marsic et al., Vector design Tour de Force: integrating combinatorial and rational approaches to derive novel adeno-associated virus variants, Molecular Therapy, 22(11):1900-1909 (2014).
McCarty et al., Adeno-associated virus terminal repeat (TR) mutant generates self-complementary vectors to overcome the rate-limiting step to transduction in vivo, Gene. Ther., 10(26):2112-2118 (2003).
McCarty et al., Self-complementary recombinant adeno-associated virus (scAAV) vectors promote efficient transduction independently of DNA synthesis, Gene Ther. 8: 1248-1254 (2001).
McLaughlin et al., Adena-associated virus general transduction vectors: analysis of proviral structures, J. Virol. 62:1963-73 (1988).
Meadows et al., Micro-RNA-29 Overexpression by adeno-associated virus suppresses fibrosis in mdx:utrn+/− Mice (S61.003), Neurology. 82:S61.003 (Abstract) (2014).
Meadows et al., Reducing Skeletal Muscle Fibrosis with AAV-Delivered miR-29 (P04.089), Neural., 1 Supplement, (2012).
Melacini et al., Heart involvement in muscular dystrophies due to sarcoglycan gene mutations, Muscle Nerve. 22:473-479 (1999).
Mendell et al., A phase 1/2a follistatin gene therapy trial for becker muscular dystrophy, Mol. Ther., 23: 192-201 (2015).
Mendell et al., Gene Therapy for Spinal Muscular Atrophy Type 1 Shows Potential to Improve Survival and Motor Functional Outcomes, Mol. Ther. 24:S190 (2016).
Mendell et al., Single-Dose Gene-Replacement Therapy for Spinal Muscular Atrophy, N. Engl. J. Med., 377:1713-1722 (2017).
Merten, AAV vector production: state of the art developments and remaining challenges, Cell Gene Therapy Insights, 2(5):521-551 (2016).
Moore et al., Limb-girdle muscular dystrophy in the United States, J. Neuropathol. Exp. Neurol., 65(10):995-1003 (2006).
Moorwood et al., Isometric and eccentric force generation assessment of skeletal muscles isolated from murine models of muscular dystrophies, Journal of Visualized Experiments. 71:e50036 (2013).
Mori et al., Two novel adeno-associated viruses from cynomolgus monkey: pseudotyping characterization of capsid protein, Virology, 330(2):375-383 (2004).
Murphy et al., Long-term correction of obesity and diabetes in genetically obese mice by a single intramuscular injection of recombinant adeno-associated virus encoding mouse leptin, Proc. Natl. Acad. Sci. USA, 94(25):13921-13926 (1997).
Muscat et al., Multiple 5'-flanking regions of the human alpha-skeletal actin gene synergistically modulate muscle-specific expression, Mol. Cell. Biol., 7(11):4089-4099 (1987).
Muzyczka, Use of adeno-associated virus as a general transduction vector for mammalian cells, Curr. Top. Microbiol. Immunol. 158:97-129 (1992).
Narayanaswami et al., Evidence-based guideline summary: diagnosis and treatment of limb-girdle and distal dystrophies: report of the

(56) References Cited

OTHER PUBLICATIONS guideline development subcommittee of the American Academy of Neurology and the practice issues review panel of the American Association of Neuromuscular & Electrodiagnostic Medicine, Neurology. 83:1453-1463 (2014).
Paul et al., Increased viral titer through concentration of viral harvests from retroviral packaging lines, Hum. Gene. Ther. 4:609-15 (1993).
Perrin et al., An experimental rabies vaccine produced with a new BHK-21 suspension cell culture process: use of serum-free medium and perfusion-reactor system, Vaccine. 13:1244-50 (1995).
Pozsgai et al.,—Sarcoglycan gene transfer decreases fibrosis and restores force in LGMD2E mice, Gene Ther. 23:57-66 (2016).
Pozsgai et al., 172. Pre-Clinical Efficacy Study of Beta-Sarcoglycan Gene Transfer, Malec. Ther., 21(1):s68 (2013).
Pozsgai et al., Beta-Sarcoglycan Gene Transfer Leads to Functional Improvement in a Model of LGMD2E (S61.002), Neur., 82(10):1-3 (2014).
Pozsgai et al., Systemic AAV-mediated (Beta)-sarcoglycan delivery targeting cardiac and Skeletal muscle ameliorates histological and functional deficits in LGMD2E mice, Mol. Ther. 25(4):855-869 (2017).
Rabinowitz et al., Cross-packaging of a single adeno-associated virus (AAV) type 2 vector genome into multiple AAV serotypes enables transduction with broad specificity, J. Virol. 76:791-801 (2002).
Rafael-Fortney et al., Early treatment with lisinopril and spironolactone preserves cardiac and skeletal muscle in duchenne muscular dystrophy mice, Circulation. 124:582-8 (2011).
Rodino-Klapac et al., A translational approach for limb vascular delivery of the micro-dystrophin gene without high volume or high pressure for treatment of Duchenne muscular dystrophy, J. Transl. Med. 5:45 (2007).
Rodino-Klapac et al., Lack of toxicity of alpha-sarcoglycan overexpression supports clinical gene transfer trial in LGMD2D, Neurology. 71: 240-247 (2008).
Rodino-Klapac et al., Persistent expression of FLAG-tagged micro dystrophin in nonhuman primates following intramuscular and vascular delivery, Mol. Ther. 18:109-117 (2010).
Ruffing et al., Mutations in the carboxy terminus of adeno-associated virus 2 capsid proteins affect viral infectivity: lack of an RGD integrin-binding motif Free, J. Gen. Virol., 75:3385-3392 (1994).
Salva et al., Design of tissue-specific regulatory cassettes for high-level rAAV-mediated expression in skeletal and cardiac muscle, Mol. Ther., 15(2):320-9 (2007).
Sambrook et al., Molecular Cloning: A Laboratory Manual, Cold Spring Harbor Laboratory, Cold Spring Harbor, New York (2nd ed. 1989).
Samulski et al., Cloning of adeno-associated virus into pBR322: rescue of intact virus from the recombinant plasmid in human cells, Proc. Natl. Acad. Sci. USA. 79:2077-81 (1982).
Samulski et al., Helper-free stocks of recombinant adeno-associated viruses: normal integration does not require viral gene expression, J. Virol. 63:3822-8 (1989).
Sandona et al., Sarcoglycanopathies: molecular pathogenesis and therapeutic prospects, Exp Rev. Mol. Med. 11:e28 (2009).
Schnepp et al., Highly purified recombinant adeno-associated virus vectors. Preparation and quantitation, Methods Mol. Med. 69:427-43 (2002).
Semenza et al., Hypoxia-inducible nuclear factors bind to an enhancer element located 3' to the human erythropoietin gene, Proc. Natl. Acad. Sci. U.S.A., 88(13):5680-5684 (1991).
Semplicini et al., Clinical and genetic spectrum in limb-girdle muscular dystrophy type 2E, Neurology. 84:1772-81 (2015).
Senapathy et al., Molecular cloning of adeno-associated virus variant genomes and generation of infectious virus by recombination in mammalian cells, J. Biol. Chem. 259:4661-6 (1984).
Shield et al., E-box sites and a proximal regulatory region of the muscle creatine kinase gene differentially regulate expression in diverse skeletal muscles and cardiac muscle of transgenic mice, Mol. Cell. Biol., 16(9):5058-5068 (1996).
Srivastava et al., Nucleotide sequence and organization of the adeno-associated virus 2 genome, J. Virol. 45:555-64 (1983).
Abadi et al., Supplementation with alpha-lipoic acid, CoQ10, and vitamin E augments running performance and mitochondrial function in female mice, PLoS One, 8(4):e60722 (2013).
ABSS (Sequence Alignment; WO2020006458, SEQ ID #1; accessed Mar. 12, 2024) (Year: 2024).
ABSS2 (Sequence Alignment; U.S. Appl. No. 17/255,488, SEQ ID #1; accessed Mar. 12, 2024) (Year: 2024).
Allamand et al., Early adenovirus-mediated gene transfer effectively prevents muscular dystrophy in alpha-sarcoglycan-deficient mice, Gene Ther., 7(16):1385-91 (2000).
Anderson et al., "Quantitative Filter Hybridisation—Chapter 4", Nucleic acid hyridisation a practical approach, 1985, pp. 73-111.
Arnold et al., Electrophysiological Biomarkers in Spinal Muscular Atrophy: Preclinical Proof of Concept, Ann. Clin. Transl. Neural., 1 (1 ):34-44 (Jan. 2014).
Asokan et al., The AAV Vector Toolkit: Poised at the Clinical Crossroads; Molecular Therapy, 20(4):699-708 (2012).
Au et al., "Gene therapy advances: a meta-analysis of AAV Usage in Clinical Settings," Frontiers in Medicine, Feb. 9, 2022, vol. 8 (pp. 1-14).
Bang et al., The complete gene sequence of titin, expression of an unusual approximately 700-kDa titin isoform, and its interaction with obscurin identify a novel Z-line to I-band linking system, Gire. Res. 89:1065-72 (2001).
Bartoli et al., "Safety and efficacy of AAV-mediated calpain 3 gene transfer in a mouse model of limb-girdle muscular dystrophy type 2A", Mol. Ther., 13(2):250-259 (2006).
Bearzi et al., Human cardiac stem cells, Proc. Natl. Acad. Sci. USA. 104:14068-73 (2007).
Behlke, Chemical modification of siRNAs for in vivo use, Oligonucleotides. 18:305-319 (2008).
Belfort et al., Homing endonucleases: from genetic anomalies to programmable genomic clippers Methods Mal. Biol. 1123:1-26 (2014).
Boch et al., Breaking the code of DNA binding specificity of TAL-type III effectors, Science. 326:1509-12 (2009).
Boissel et al., "megaTALs" a rare-cleaving nuclease architecture for therapeutic genome engineering, Nucleic Acids Research, 2014, vol. 42, No. 4 (pp. 2591-2601).
Boissel et al., Assembly and characterization of megaTALs for hyperspecific genome engineering applications, Methods Mal. Biol. 1239:171-96 (2015).
Bolduc et al., "Recessive Mutations in the Putative Calcium-Activated Chloride Channel Anoctamin 5 Cause Proximal LGMD2L and Distal MMD3 Muscular Dystrophies", The American Journal of Human Genetics, 86, Feb. 12, 2010, (pp. 213-221).
Bouquet et al., Miyoshi-like distal myopathy with mutations in anoctamin 5 gene, Rev. Neural. (Paris), 168(2):135-41 (Feb. 2012).
Bramsen et al., Development of therapeutic-grade small interfering RNAs by chemical engineering, Front. Genet. 20:154 (2012).
Carter et al., "Adeno-associated virus vectors," Current Opinions in Biotechnology, 1992, vol. 3, Issue 5, pp. 533-539.
Ceccadi et al., Homologous recombination-deficient tumors are hyper-dependent on POLQ mediated repair, Nature. 518:258-262 (2015).
Cekaite et al., Gene expression analysis in blood cells in response to unmodified and 2'-modified siRNAs reveals TLR-dependent and independent effects, J. Mal. Biol. 365:90-108 (2007).
Centner et al., Identification of muscle specific ring finger proteins as potential regulators of the titin kinase domain, J. Mal. Biol. 306:717-26 (2001).
Cermak et al., "Efficient design and assembly of custom TALEN and other TAL effector-based constructs for DNA targeting," Nucleic Acids Research, 2011, (pp. 1-11).
Cermak et al., Efficient design and assembly of custom TALENs using the Golden Gate platform, Methods Mal. Biol. 1239:133-59 (2015).

(56) References Cited

OTHER PUBLICATIONS

Ceyhan-Birsoy et al., Recessive truncating titin gene, TTN, mutations presenting as centronuclear myopathy, Neuroloov. 81:1205-14 (2013).
Chandrasekharan et al., Genetic defects in muscular dystrophy, Methods Enzymol. 479:291-322 (2010).
Chauveau et al., A rising titan: TTN review and mutation update, Human Mutation. 35:1046-59 (2014).
Chernolovskaya et al., Chemical modification of siRNA, Curr. Opin. Mal. Ther. 12:158-67 (2010).
Chiorini et al., Cloning and characterization of adeno-associated virus type 5, J. Viral., 73(2):1309-19 (Feb. 1999).
Chiorini et al., Cloning of adeno-associated virus type 4 (AAV4) and generation of recombinant AAV4 particles, J. Viral., 71 (9):6823-33 (Sep. 1997).
Cho et al., DNA repair: Familiar ends with alternative endings, Nature. 518:174-6 (2015).
Cox et al., "Therapeutic genome editing: prospects and challenges," Nature Medicine, Feb. 21, 2015, vol. 2 (pp. 121-131).
D'Amario et al., Functionally competent cardiac stem cells can be isolated from endomyocardial biopsies of patients with advanced cardiomyopathies, Gire. Res. 108:857-61 (2011).
Database Genbank [online], Accession No. AJ277892.2, Nov. 14, 2006 issue.
Daya et al., "Gene Therapy Using Adeno-Associated Virus Vectors," Clinical Microbiology Reviews, Oct. 2008, vol. 21, No. 4 (pp. 583-593).
Deleavey et al., Chemical modification of siRNA, Curr. Protoc. Nucleic Acid Chem. Chapter 16: Unit 16.3 (2009).
Doench et al., "Optimized sgRNA design to maximize activity and minimize off-target effects of CRISPR-Cas9", Nature Biotechnology, Feb. 2016, vol. 34, No. 2 (pp. 184-191).
Dreier et al., "Development of Zinc Finger Domains for Recognition of the 5'-ANN-3' Family of DNA Sequences and Their Use in the Construction of Artificial Transcription Factors," The Journal of Biological Chemistry, August 3, vol. 276, No. 31 (pp. 29466-29478) (2001).
Dreier et al., Insights into the molecular recognition of the 5'-GNN-3' family of DNA sequences by zinc finger domains, J. Mal. Biol. 303:489-502 (2000).
Dreier, B. et al, "Development of zinc finger domains for recognition of the 5'-CNN-3' family DNA sequence and their use in the construction of artificial transcription factors", The Journal of Biological Chemistry, vol. 280, No. 42, Oct. 21, 2005, pp. 35588-3597.
Fanin et al., Gender difference in limb-girdle muscular dystrophy: a muscle fiber morphometric study in 101 patients, Clin. Neuropathology, 33:179-801 (2014).
Fonfara et al., "Phylogeny of Cas9 determines functional exchangeability of dual-RNA and Cas9 among orthologous type II CRISPR-Cas systems", Nucleic Acids Research, vol. 42, No. 4, Nov. 22, 2013, pp. 2377-2590 (14 pages).
Forbes et al., "Skeletal muscles of ambulant children with Duchenne muscular dystrophy: validation of multicenter study of evaluation with MR imaging and MR spectroscopy", Radiology, 269:198-207 (2013).
Foye, Whole Genome Sequencing Solved Our Family's Genetic Mystery: Titin, Narrat. Inq. Bioeth 5:206-8 (2015).
Fucini et al., Adenosine modification may be preferred for reducing siRNA immune stimulation, Nucleic Acid Ther. 22:205-210 (2012).
Gaglione et al., Recent progress in chemically modified siRNAs, Mini. Rev. Med. Chem. 10:578-9t (2010).
Gao et al., A novel and efficient model of coronary artery ligation and myocardial infarction in the mouse, Gire. Res. 107:1445-53 (2010).
Gao et al., A novel and efficient model of coronary artery ligation in the mouse, Methods Mal. Bic 1037:299-311 (2013).
Gao et al., Adeno-associated viruses undergo substantial evolution in primates during natural infections, Proc. Natl. Acad. Sci. U.S.A., 2003, vol. 100, pp. 6081-6086.

Gautel et al., The central Z-disk region of titin is assembled from a novel repeat in variable copy numbers, Journal of Cell Science. 109:2747-2754 (1996).
Gebeyehu, et al., "Novel biotinylated nucleotide—analogs for labeling and colorimetric detection of DNA," Nucleic Acids Research, vol. 15, No. 11, (Jun. 11, 1987), p. 4513-4534.
GenBank Accession No. AF028704.1, Adena-associated virus 6, complete genome, Jan. 12, 1998.
GenBank Accession No. AF028705.1, Adeno-associated virus 3B, complete genome, Jan. 12, 1998.
GenBank Accession No. AX753250.1, Sequence 5 from Patent EP1310571, Jun. 23, 2003.
GenBank Accession No. AY631965.1, Adena-associated virus 10 nonstructural protein and caps protein genes, complete eds, Nov. 30, 2004.
GenBank Accession No. AY631966.1, Adena-associated virus 11 nonstructural protein and caps protein genes, complete eds, Nov. 30, 2004.
GenBank Accession No. DO813647.1, Adena-associated virus 12 Rep78 and VP1 genes, complete eds, Feb. 20, 2008.
GenBank Accession No. EU285562.1, Adena-associated virus 13 nonstructural protein and capsid protein genes, complete eds, Sep. 23, 2008.
GenBank Accession No. NC_001401.2, Adeno-associated virus—2, complete genome, Aug. 13, 2018.
GenBank Accession No. NC_006152.1, Adeno-associated virus 5, complete genome, Aug. 13, 2018.
GenBank Accession No. NC_006260.1, Adeno-associated virus—7, complete genome, Aug. 13, 2018.
GenBank Accession No. NC_006261.1, Adeno-associated virus—8, complete genome, Aug. 13, 2018.
Genbank Accession No. J01901, Adeno-associated virus 2, complete genome, Apr. 27, 1993.
GenBank Accession No. U89790.1, Adeno-associated virus 4, complete genome, Aug. 21, 2017.
GenBank Registered No. NG_011618, *Homo sapiens* titin (TTN), RefSeqGene (LRG_391) on chromosome 2 (2020).
Genbank Synthetic construct Homo sapiens clone Image: 100069183, MGC: 199194 anoctamin 5 (ANO5) mRNA, encodes complete protein GenBank: BC172489.1, (2009).
Georganopoulou et al., "A Journey with LGMD: From Protein Abnormalities to Patient Impact", The Protein Journal, Kluwer Academic/Plenum Publishers, Dordrecht, NL, vol. 40, No. 4, Jun. 10, 2021, pp. 466-488.
Gerull et al., Identification of a novel frameshift mutation in the giant muscle filament titin in a large Australian family with dilated cardiomyopathy, J. Mal. Med. (Berl). 84:478-83 (2006).
Gerull et al., Mutations of TTN, encoding the giant muscle filament titin, cause familial dilated cardiomyopathy, Nat. Genet. 30:201-4 (2002).
Goeddel, "Gene Expression Technology: Methods in Enzymology," Academic Press, vol. 185, Jun. 11, 1990, pp. 3-7.
Gombash et al., Adeno-Associated Viral Vector Delivery to the Enteric Nervous System: A Review, Postdoc J., 2015, vol. 3, Issue 8, pp. 1-12.
Govoni et al., "Ongoing therapeutics trials and outcome measures for Duchenne muscular dystrophy", Cell Mol. Life Sci., 70:4585-602 (2013).
Gramlich et al., "Antisense-mediated exon skipping: a therapeutic strategy for titin-based dilated cardiomyopathy," EMBO Molecular Medicine, 7(5): 562-76 (2015).
Gramlich et al., "Stress-induced dilated cardiomyopathy in a knock-in mouse model mimicking human titin-based disease", J. Mal. Cell Cadiol. 47:352-8 (2009).
Granzier et al., "Deleting titin's I-band/A-band junction reveals critical roles for titin in biomechanica sensing and cardiac function", Proc. Natl. Acad. Sci. USA. 111:14589-94 (2014).
Griffin et al., Defective Membrane Fusion and Repair in Anoctamin5-Deficient Muscular Dystrophy, Human Molecular Genetics, vol. 25, No. 10, pp. 1900-1911 (Feb. 23, 2016).
Griffin et al., "Dose-Escalation of Systemically Delivered Adeno-Associated Virus-Mediated alpha-Sarcoglycan in a Mouse Model With Limb-Girdle Muscular Dystrophy Type 2D," Presented at the

(56) References Cited

OTHER PUBLICATIONS

2019 Muscular Dystrophy Association Clinical and Scientific Conference, Apr. 13-17, 2019. (Retrieved from: investorrelations.sarepta.com/staticfiles/8b00e773-3b86-4769-83dc-4d2bf22ffb0c).
Griffin et al., "Systemic Dose Escalation Study of Alpha-Sarcoglycan Provides Functional Improvement in SGCA (I-) Mouse Model of LGMD2D," Molecular Therapy, vol. 26, No. 5S1, May 2018, p. 166.
Grose et al., "Homologous Recombination Mediates Functional Recovery of Dysferlin Deficiency following AAV5 Gene Transfer", PLoS One, Jun. 2012, vol. 7, Issue 6, e39233.
Guilinger et al., "Fusion of catalytically inactive Cas9 to FokI nuclease improves the specificity of genome modification," Nature Biotechnology, vol. 32, No. 6, Jun. 2014 (pp. 577-582).
Gutschner et al., "Genome engineering—Matching supply with demand," Cell Cycle, 15(11): 1395-96 2016.
Hafez et al., "Homing endonucleases: DNA scissors on a mission", Genome. 55:553-69 (2012).
Hagan, "When are mice considered old?" The Jackson Laboratory, https://www.jax.org/news-and-insights/jax-blog/2017/november/when-are-mice-considered-old# Nov. 7, 2017 (8 pages).
Hakim et al., Monitoring murine skeletal muscle function for muscle gene therapy, Methods Mal. Biol., 2011, vol. 709, pp. 75-89.
Handschin et al., Peroxisome proliferator-activated receptor gamma coactivator 1 coactivators, energy homeostasis, and metabolism, Endocrine reviews, 27:728-735 (2002).
Herman et al., "Truncations of titin causing dilated cardiomyopathy", N. Engl. J. Med. 366:619-28, 2012.
Hicks et al., A founder mutation in Anoctamin 5 is a major cause of limb-girdle muscular dystrophy, Brain, 134 (Pt. 1):171-82 (Jan. 2011).
Horii et al., Validation of microinjection methods for generating knockout mice by CRISPR/Cas-mediated genome engineering, Sci Rep. 4:4513 (2014).
International Application No. PCT/US12/66265, International Search Report and Written Opinion, mailed Mar. 28, 2013.
International Application No. PCT/US19/39893, International Preliminary Report on Patentability, mailed Jan. 7, 2021.
International Application No. PCT/US19/39893, International Search Report and Written Opinion, mailed Sep. 25, 2019.
International Application No. PCT/US20/47339, International Preliminary Report on Patentability, mailed Mar. 3, 2022.
International Application No. PCT/US2016/061703, International Preliminary Report on Patentability, mailed May 15, 2018.
International Preliminary Report on Patentability for Appl. Ser. No. PCT/US2019/039893 dated Dec. 29, 2020 (7 pages).
International Preliminary Report on Patentability for Appl. Ser. No. PCT/US2016/062052 dated May 22, 2018.
International Preliminary Report on Patentability on PCT Appl. No. PCT/US2012/066265 dated May 27, 2014 (9 pages).
International Search Report and Written Opinion for Appl. Ser. No. PCT/US2016/062052 dated Feb. 7, 2017 (5 pages).
International Search Report and Written Opinion for Appl. Ser. No. PCTUS2016/061703 dated Feb. 2, 2017 (13 pages).
International Search Report and Written Opinion on PCT Appl. No. PCT/US2020/047339 dated Dec. 10, 2020 (12 pages).
Itoh-Satoh et al., Titan mutations as the molecular basis for dilated cardiomyopathy, Biochem. Biophys. Res. Commun. 291:385-93 (2002).
Jaber et al., Titin isoforms, extracellular matrix, and global chamber remodeling in experimental dilated cardiomyopathy: functional implications and mechanistic insight, Circ. Heart Fail. 1:192-9 (2008).
Jinek et al., "A Programmable Dual-RNA-Guided DNA Endonuclease in Adaptive Bacterial Immunity," Science, Aug. 17, 2012, 337(6096):816-821.
John Hopkins Medicine, "Types of Muscular Dystrophy and Neuromuscular diseases," 2023, 6 pages.
Judge et al., "Design of noninflammatory synthetic siRNA mediating potent gene silencing in vivo", Mol. Ther. 13:494-505 (2006).

Justison et al., Percutaneous assisted venous return isolated limb perfusion, J. Extra Corpor. Technol., 2009, vol. 41, Issue 4, pp. 231-234.
Kajigaya et al., Self-assembled B19 parvovirus caps ids, produced in a baculovirus system, are antigenically and immunogenically similar to native virions, Proc. Natl. Acad. Sci. USA, 88(11):4646-50 (Jun. 1991).
Kariko et al., "Suppression of RNA recognition by Toll-like receptors: the impact of nucleoside modification and the evolutionary origin of RNA," Immunity, Aug. 2005, vol. 23 (pp. 165-175).
Kennell, "Principles and Practices of Nucleic Acid Hybridization," Progress in Nucleic Acid Research and Molecular Biology, Academic Press, vol. 11, 1971, (pp. 259-301).
Kent et al., "Mechanism of microhomology-mediated end-joining promoted by human DNA polymerase theta", Nat. Struct. Mol. Biol. 22:230-237 (2015).
Kirnbauer et al., Virus-like particles of bovine papillomavirus type 4 in prophylactic and therapeutic immunization, Virology, 219(1):37-44 (May 1996).
Kleinstiver et al., The I-TevI nuclease and linker domains contribute to the specificity of monomerh TALENs, G3 (Bethesda). 4:1155-65 (2014).
Kole et al., "RNA therapeutics: beyond RNA interference and antisense oligonucleotides", Nat Rev Drug Discov. Jan. 20, 2012;11(2):125-40. doi: 10.1038/nrd3625.
Kolmerer et al., "Genomic organization of M line titin and its tissue-specific expression in two distinct isoforms", J. Mol. Biol. 256:556-63 (1996).
Kormann et al., "Expression of therapeutic proteins after delivery of chemically modified mRNA in mice," Nature Biotechnology, Feb. 2011, vol. 29, No. 2 (pp. 154-157).
Kornberg et al., "The early history of DNA polymerase: a commentary by Arthur Kornberg", Biochimica et Biophysica Acta. 1000:53-56 (1989).
Kotin et al., "Manufacturing Clinical Grade Recombinant Adeno-Associated Virus Using Invertebrate Cell Lines," Human Gene Therapy, 28(4):Abstract Only, (Apr. 1, 2017).
Kramerova et al., "Null mutation of calpain 3 {p94) in mice causes abnormal sarcomere formation in vivo and in vitro", Hum. Mol. Genet., 13(13):1373-1388 (2004).
Kramerova et al., Failure to up-regulate transcription of genes necessary for muscle adaptation underlies limb girdle muscular dystrophy 2A calpainopathy, Hum. Mol. Genet., 25(11):2194-2207 (2016).
Labeit et al., "Titins: giant proteins in charge of muscle ultrastructure and elasticity", Science. 270:293-6 (1995).
Lewinter et al., Cardiac titin and heart disease, J. Cardiovasc. Pharmacol. 63:207-12 (2014).
Lewinter, "Titin isoforms in heart failure: are there benefits to supersizing", Circulation. 110:109-11 2004.
Li et al., "Modularly assembled designer TAL effector nucleases for targeted gene knockout and gene replacement in eukaryotes," Nucleic Acids Research, 2011, vol. 39, No. 14 (pp. 6315-6325).
Li et al., Electrical impedance myography for the in vivo and ex vivo assessment of muscular dystrophy (mdx) mouse muscle, Muscle Nerve, 49(6):829-35 (Jun. 2014).
Li et al., Electrophysiologic biomarkers for assessing disease progression and the effect of riluzole in SOD1 G93A ALS mice, PLoS One, 8(6):e65976 (Jun. 2013).
Li et al., Intracoronary administration of cardiac stem cells in mice: a new, improved technique for cell therapy in murine models, Basic Res. Cardiol. 106:849-64 (2011).
Lin et al., Transcriptional co-activator PGC-1 alpha drives the formation of slow-twitch muscle fibres, Nature, 418:797-801 (2002).
Liu et al., "Validated Zinc Finger Protein Designs for All 16 GNN DNA Triplet Targets," The Journal of Biological Chemistry, Feb. 8, 2002, vol. 277, No. 6 (pp. 3850-3856).
Louis et al., "EM_EST:BE676391", Jan. 27, 2011 (Jan. 27, 2011), XP055708767, Retrieved from the Internet: RL:http://ibis.internal.epo.org/exam/dbfetch.jsp?id=EM_EST:BE676391 [retrieved on Jun. 25, 2020].
Ma et al., Pol III Promoters to express small RNAs: Delineation of transcription initiation, Mol. Ther. Nucleic Acids. 3:e161 (2014).

(56) References Cited

OTHER PUBLICATIONS

Mahmood et al., "Limb-girdle muscular dystrophies: Where next after six decades from the first proposal (review)," Molecular Medicine reports, 2014, vol. 9 (pp. 1515-1532).
Mak et al., "The crystal structure of TAL effector PthXo1 bound to its DNA target," Science, Feb. 10, 2012, vol. 335, No. 6069 (pp. 716-719).
Makarenko et al., Passive stiffness changes caused by upregulation of compliant titin isoforms in human dilated cardiomyopathy hearts, Gire. Res. 95:708-16 (2004).
Martin et al., Overexpression of Galgt2 in skeletal muscle prevents injury resulting from eccentric contractions in both mdx and wild-type mice, Am. J. Physiol. Cell Physiol., vol. 296, pp. 476-488 (2009).
Mashiko et al., Generation of mutant mice by pronuclear injection of circular plasmid expressing Cas9 and single guided RNA, Sci. Rep. 3:3355 (2013).
Mateos-Gomez et al., Mammalian Polymerase theta promotes alternative-NHEJ amd suppresses recombination, Nature. 518:254-257 (2015).
McCarty et al., Self-complementary AAV Vectors; Advances and Applications, Molecular Therapy, 2008, vol. 16, Issue 10, pp. 1648-1656.
McNally et al., The genetic landscape of cardiomyopathy and its role in heart failure, Cell. Metab. 21:174-182 (2015).
Mendell et al., "Gene Therapy for Muscular Dystrophy: Lessons Learned and Path Forward", Neuroscience Letters, vol. 527, No. 2, Oct. 2012, 21 pages.
Mendell et al., "Limb-girdle muscular dystrophy type 2D gene therapy restores alpha-sarcoglycan and associated proteins," Ann. Neural., 2009, vol. 66 Issue 3, pp. 290-297.
Mendell et al., "Sustained alpha-sarcoglycan gene expression after gene transfer in limb-girdle muscular dystrophy, type 2D," Annals of neurology, 2010, vol. 68, Issue 5, pp. 629?
Mendell et al., Gene Delivery for Limb-Girdle Muscular Dystrophy Type 2D by Isolated Limb Infusion, Human Gene Therapy, 2019, vol. 30, Issue 7, pp. 794-801.
Mingozzi et al. "Therapeutic in vivo gene transfer for genetic disease using AAV: progress and challenges", Nature Reviews Genetics, May 2011, vol. 12 (pp. 341-355).
Monjaret et al., "The Phenotype of Dysferlin-Deficient Mice is not Rescued by Adeno-Associated Virus-Medicated Transfer of Anoctamin 5," Human Gene Therapy Clinical Development, 24(2):65-76 (Jun. 1, 2013).
Moscou et al., "A Simple Cipher Governs DNA Recognition by TAL Effectors", Science, Dec. 11, 2009, vol. 326 (p. 1501).
NCBI Accession No. NG_051363.1, *Homo sapiens* TTN antisense RNA 1 (TTN-AS1), RefSeqGene on chromosome 2, dated Feb. 17, 2020.
NCBI Accession No. XM_012650762.1, Predicted: Propithecus coquereli titin (TTN), mRNA, dated Jun. 1, 2015.
NCBI Accession No. XM_024453100.1, Predicted: *Homo sapiens* titin (TTN), transcript variant X12, mRNA, dated Mar. 1, 2020.
NCBI BLAST Tool: Pairwise Similarity 1, Instant App ('488) SEQ ID No. 1 [1-3977]:: US9981049B2 SEQ ID No. 8 (CAPN3) (2024).
NCBI BLAST Tool: Pairwise Similarity 2, Instant App ('488) SEQ ID No. 1 [1107-3572]:: US9981049B2 SEQ ID No. 8 (CAPN3) (2024).
NCBI Reference Sequence: "anoctamin-5 isoform a [*Homo sapiens*]", GenPept, Mar. 15, 2015, NP_998764.1.
Obermann et al., Molecular structure of the sarcomeric M band: mapping of titin and myosin binding domains in myomesin and the identification of a potential regulatory phosphorylation site in myomesin, EMBO J. 16:211-20 (1997).
Pacak et al., Long-term Skeletal Muscle Protection After Gene Transfer in a Mouse Model of LGMD-2D, Molecular Therapy, 2007, vol. 15, Issue 10, pp. 1775-1781.
Pavlovicova et al., Structure and composition of tubular aggregates of skeletal muscle fibres, Gen. Physiol. Biophys., 22(4):425-40 (Dec. 2003).

Payne et al., Nutritional therapy improves function and complements corticosteroid intervention in mdx mice. Muscle Nerve. Jan. 2006; 33(1):66-77.
Peer et al., Special delivery: targeted therapy with small RNAs, Gene. Ther. 18:1127-33 (2011).
Peled et al., Titin mutation in familial restrictive cardiomyopathy, Int. J. Cardiol. 171:24-30 (2014).
Penttila et al., Eight new mutations and the expanding phenotype variability in muscular dystrophy caused by ANO5, Neurology, 78(12):897-903 (Mar. 2012).
Powers et al., Exercise-induced oxidative stress in humans: cause and consequences, Free Radic. Biol. Med., 51 (5):942-50 (Sep. 2011 ).
Ran et al., "In vivo genome editing using *Staphylococcus aureus* Cas9," Nature, Apr. 9, 2015, vol. 520, (18 pages).
Richard et al., "Mutations In The Proteolytic Enzyme Calpain 3 Cause Limb-Girdle Muscular Dystrophy Type 2A", Cell, 81(1):27-40 (1995).
Roberts et al., Integrated allelic, transcriptional, and phenomic dissection of the cardiac effects of titin truncations in health and disease, Sci. Transl. Med. 7:270ra6 (2015).
Rodino-Klapac et al., "Micro-dystrophin and follistatin co-delivery restores muscle function in aged DMD model," Human Molecular Genetics, Dec. 2013, vol. 22, No. 24 (pp. 4929-4937).
Rodino-Klapac et al., Demonstration of SGCA Expression and Related Outcomes in Phase I/IIa Safety Isolated Limb Perfusion Trial in LGMD2D Subjects, Molecular Theerapy, 2018, vol. 26, Issue 5, Supplemental 1, p. 1, Abstract No. 250.
Roudaut et al., "Restriction of Calpain3 Expression to the Skeletal Muscle Prevents Cardiac Toxicity and Corrects Pathology in a Murine Model of Limb-Girdle Muscular Dystrophy", Circulation, 128(10): 1094-1104, (Sep. 2013).
Rutledge et al., Infectious clones and vectors derived from adeno-associated virus (AAV) serotypes other than AAV type 2, J. Viral., 7291 ):309-19 (Jan. 1998).
Sahenk et al., Systemic delivery of AAVrh74.tMCK.hCAPN3 rescues the phenotype in a mouse model for LGMD2A/R1, Mol. Ther. Methods Clin. Dev., 22:401-414 (2021).
Sambrook et al., Cold spring harbor laboratory press, cold Spring Harbor, N.Y., (2001).
Sambrook et al., Molecular Cloning: A Laboratory Manual, 2 edition (1989).
Sander et al., CRISPR-Cas systems for editing, regulating and targeting genomes, Nat. Biotechnol. 32:347-55 (2014).
Sanganalmath et al., Cell therapy for heart failure: a comprehensive overview of experimental and clincal studes, current challenges, and future directions, Gire. Res. 113:810-34 (2013).
Sarepta Therapeutics: "Sarepta Therapeutics' Investigational Gene Therapy SRP-9003 for the Treatment of Limb-Girdle Muscular Dystrophy Type 2E Shows Sustained Expression and Functional Improvements 2 Years After Administration", Mar. 18, 2021, pp. 1-3, Retrieved from the Internet: URL: https://investorrelations.sarepta.com/news---releases/news-release---details/sarepta-therapeutics---investigational-gene-therapy -srp-9003-0 [retrieved on Jun. 23, 2023].
Schreiber et al., The transcriptional coactivator PGC-1 regulates the expression and activity of the orphan nuclear receptor estrogen-related receptor alpha (ERRalpha), J. Biol. Chem., 278: 9013-9018 (2003).
Segal et al., "Toward controlling gene expression at will: Selection and design of zinc finger domains recognizing each of the 5'-GNN-3' DNA target sequences," Proceedings of the National Academy of Sciences, USA, Mar. 1999, vol. 96 (pp. 2758-2763).
Shih et al., Finding the Achilles' heel of Muscle Giant-TALEN-mediated Gene-editing in Zebrafish Titin', Circulation Research, Oct. 21, 2015, vol. 117, No.(suppl_1), pp. A344. DOI: https://doi.org/10.1161/res.117.suppl_1.344.
Siu et al., Familial dilated cardiomyopathy locus maps to chromosome 2q31, Circulation. 99:1022-6 (1999).
Smith et al., Modification and secretion of human interleukin 2 produced in insect cells by a baculovirus expression vector, Proc. Natl. Acad. Sci. USA, 82(24):8404-8 (1985).

(56) References Cited

OTHER PUBLICATIONS

Sondergaard et al., "AAV.Dysferlin Overlap Vectors Restore Function in Dysferlinopathy Animal Models," Annals of Clinical and Translational Neurology, 2015, vol. 2, Issue 3, pp. 256-270.
Sonntag et al., A viral assembly factor promotes AAV2 capsid formation in the nucleolus, PNAS,2010, vol. 107, Issue 22, pp. 10220-10225.
Sorimachi et al., Tissue-specific expression and alpha-actinin binding properties of the Z-disc titin: implications for the nature of vertebrate Z-discs, J. Mal. Biol. 270:688-95 (1997).
Soutschek et al., "Therapeutic silencing of an endogenous gene by systemic administration of modified siRNAs," Nature, Nov. 2004, pp. 173-178, vol. 432.
Steentoft et al., Precision genome editing: a small revolution for glycobiology, Glycobiology. 24:663-80 (2014).
Strobel, et al. "Antioxidant Supplementation Reduces Skeletal Muscle Mitochondrial Biogenesis", Official Journal of the American College of Sports Medicine, 2011, pp. 1017-1024.
Thiruvengadam et al., "Anoctamin 5 Knockout Mouse Model Recapitulates LGMD2L Muscle Pathology and Offers Insight Into in vivo Functional Deficits," Journal of Neuromuscular Diseases, 2021, vol. 8 (S243-S255).
Torella, et al., "Cardiovascular development: towards biomedical applicability; Resident cardiac stem cells", CMLS Cellular and Molecular Life Sciences 64(6): 661-673 (2007).
Tsai et al., "GUIDE-seq enables genome-wide profiling of off-target cleavage by CRISPR-Cas nucleases," Nature Biotechnology, Feb. 2015, vol. 33, No. 2 (pp. 187-197).
Tsai et al., Dimeric CRISPR RNA-guided FokI nucleases for highly specific genome editing, Nat. Biotechnol. 32:569-76 (2014).
Van Akkooi et al., Isolated limb perfusion for an irresectable melanoma recurrence in a Jehovah's witness, Eur. J. Cardiothorac. Surg., 2006, vol. 30, Issue 2, pp. 408-410.
Volkov et al., Selective protection of nuclease-sensitive sites in siRNA prolongs silencing effect, Oligonucleotides. 19:191-202 (2009).
Wang et al., "The potential of adeno-associated viral vectors for gene delivery to muscle tissue", Exp. Opin. on Drug. Del., 11(3):345-364 (2014).
Wang et al., Rapid and efficient assembly of transcription activator-like effector genes by User cloning, J. Genet. Genomics. 41:339-47 (2014).
Wang et al., Recombinant AAV serotype 1 transduction efficiency and tropism in the murine brain, Gene Ther., 2003, vol. 10, Issue 17, pp. 1528-1534.
Watson et al., "Recombinant DNA," Scientific American, Second Edition, 2001 (pp. 153-154).
Weber et al., "A Modular Cloning System for Standardized Assembly of Multigene Constructs," Feb. 2011, vol. 6, No. 2, e16765 (11 pages).
Whitehead et al., Silencing or stimulation? siRNA delivery and the immune system, Annual Review of Chemical and Biomolecular Engineering. 2:77-96 (2011).
Wikipedia, "Adeno-associated virus," downloaded Dec. 29, 2017 (pp. 1-18).
Wikipedia, "Limb-girdle muscular dystrophy," 11 pages, Retrieved Oct. 26, 2023, from https://en.wikipedia.org/wiki/Limb-girdle_muscular_dystrophy (11 pages).
Winkler, Oligonucleotide conjugates for therapeutic applications, Ther. De/iv. 4:791-809 (2013).
Witting et al: "Anoctamin 5 muscular dystrophy in Denmark: prevalence, genotypes, phenotypes, cardiac findings, and muscleprotein expression", Case Reports, May 14, 2013, PMID: 23670307 DOI: 10.1007/s00415-013-6934-y.
Wolfs et al., MegaTevs: single-chain dual nucleases for efficient gene disruption, Nucliec Acids Res. 42:8816-29 2014).
Wu et al., Mutational analysis of the adeno-associated virus type 2 (AAV2) capsid gene and construction of AAV2 vectors with altered tropism, J. Viral., 74(18):8635-47 (Sep. 2000).
Xu et al., "Genetic disruption of Ano5 in mice does not recapitulate human ANO5-deficient muscular dystrophy," Skeletal Muscle, 2015, vol. 5, No. 43 (pp. 1-14).
Xu et al., Postnatal overexpression of the CT GalNAc transferase inhibits muscular dystrophy in mdx mice without altering muscle growth or neuromuscular development: evidence for a utrophin-independent mechanism, Neuromuscul. Disord., 2007, vol. 17, Issue 3, pp. 209-220.
Yalvac et al., Impaired regeneration in calpain-3 null muscle is associated with perturbations in mTORC1 signaling and defective mitochondrial biogenesis, Skelet. Muscle, 7:27, 18 pages (2017).
Yan et al., Inverted terminal repeat sequences are important for intermolecular recombination and circularization of adeno-associated virus genomes, J. Viral., 79(1 ):364-79 (Jan. 2005).
Yuasa et al., "Gene therapy of muscular dystrophy: Systemic gene delivery to skeletal muscles" Jan. 2007, Drug Delivery System 22(2):140-147, doi. org/10.2745/dds.22.140 (English Abstract).
Zetsche at el., "Cpfl Is a Single RNA-Guided Endonuclease of a Class 2 CRISPR-Cas System," Cell, Oct. 22, 2015, vol. 163, No. 3 (pp. 759-771).
Zhao et al., BPV1 E2 protein enhances packaging of full-length plasmid DNA in BPV1 pseudovirions, Virology, 272(2):382-93 (Jul. 2000).
Zhou et al., Pressure Overload by Transverse Aortic Constriction Induces Maladaptive Hypertrophy in a Titin-Truncated Mouse Model, Biomed. Res. Int. 2015:163564 (2015).
Zou et al., "An internal promoter underlies the difference in disease severity between N- and C-terminal truncation mutations of Titin in zebrafish", eLife, Oct. 16, 2015, vol. 4, pp. e09406. DOI: https://doi.org/10.7554/eLife.09406.
Matsuda et al., Visualization of dystrophic muscle fibers in mdx mouse by vital staining with Evans blue: evidence of apoptosis in dystrophin-deficient muscle, J. Biochem., 118(5):959-964 (1995).
Tratschin et al., "Adeno-Associated Virus Vector for High-Frequency Integration, Expression, and Rescue of Genes in Mammalian Cells", Molecular and Cellular Biology, vol. 5, Issue 11, Nov. 1985, pp. 3251-3260.
Thomas et al., "B4GALNT2 (GALGT2) Gene Therapy Reduces Skeletal Muscle Pathology in the FKRP P448L Mouse Model of Limb Girdle Muscular Dystrophy 2I", Am. J_ Pathol., 186(9):2429-2448 (2016).
Werling et al., "Systematic comparison and validation of quantitative real-time PCR methods for the quantitation of adeno-associated viral products," Human Gene Therapy Methods, 26.3:82-92 (Jun. 2015).
Hartigan-O'Connor et al., "Developments in gene therapy for muscular dystrophy," Microscopy Research and Technique 48:223-238 (2000).
Pozsgai, E.R., Adeno-Associated Virus Mediated ß-Sarcoglycan Gene Replacement Therapy for the Treatmentof Limb Girdle Muscular Dystrophy Type 2E [Doctoral dissertation, Ohio State University]. OhioLINK Electronic Theses and Dissertations Center. (2016) http://rave.ohiolink.edu/etdc/view?acc_num=osu147697211337827.

* cited by examiner

β-Sarcoglycan

α-Sarcoglycan

Colocalization (Merge)

ADENO-ASSOCIATED VIRUS VECTOR DELIVERY OF β-SARCOGLYCAN AND THE TREATMENT OF MUSCULAR DYSTROPHY

This application claims priority to U.S. Provisional Application No. U.S. Provisional Application No. 62/810,917, filed Feb. 26, 2019, U.S. Provisional Application No. 62/834,012, filed Apr. 15, 2019, U.S. Provisional Application No. 62/858,644, filed Jun. 7, 2019, U.S. Provisional Application No. 62/881,901, filed Aug. 1, 2019, U.S. Provisional Application No. 62/909,564, filed Oct. 2, 2019 and U.S. Provisional Application No. 62/910,779, filed Oct. 4, 2019, all of which are incorporated by reference herein in their entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 54016_Seqlisting.txt; Size: 33,466 bytes; Created: Feb. 12, 2020.

FIELD OF THE INVENTION

Described herein are therapy vectors such as AAV vectors expressing β-sarcoglycan and method of using these vectors to reduce and prevent fibrosis in subjects suffering from a muscular dystrophy.

BACKGROUND

Limb-girdle muscular dystrophy (LGMD) type 2E (LGMD2E) is an autosomal recessive disorder resulting from mutations in the gene encoding β-sarcoglycan (SGCB), causing loss of functional protein. LGMD2E represents a relatively common and severe form of LGMD in the United States with worldwide reports of incidence of 1/200,000-1/350,000.(2) The absence of β-sarcoglycan leads to a progressive dystrophy with chronic muscle fiber loss, inflammation, fat replacement and fibrosis, all resulting in deteriorating muscle strength and function. (3,4) As a complex, the sarcoglycans (α-, β, γ-, δ-), ranging in size between 35 and 50 kD, (5) are all transmembrane proteins that provide stability to the sarcolemma offering protection from mechanical stress during muscle activity.(3) Loss of β-sarcoglycan in LGMD2E usually results in varying degrees of concomitant loss of other sarcoglycan proteins contributing to the fragility of the muscle membrane leading to loss of myofibers.1 Although the range of clinical phenotype of LGMD2E varies, diagnosis typically occurs before age 10 and with loss of ambulation occurring by mid to late teens. Patients present with elevated serum creatine kinase (CK), proximal muscle weakness, difficulty arising from the floor and progressive loss of ambulation. Cardiac involvement occurs in as many as fifty percent of cases Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983}; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in see U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sci USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics.

An emerging form of therapy for LGMD2E is viral-mediated gene delivery to restore wild-type protein to affected muscle resulting in restoration of muscle function. Considering that a subset of patients can develop cardiomyopathy, (8, 9, 10, 13) this would have to be considered in the long-term care of these patients. In previous reports, the Sgcb-null mouse was well characterized. Araishi et al.3 developed the β-sarcoglycan-deficient mouse with accompanying loss of all of the sarcoglycans as well as sarcospan, with at least minor preservation of merosin, the dystroglycans and dystrophin, reproducing the clinical picture seen in LGMD2E. The histological changes in this animal model were also a prototype for the clinical counterpart, including the prominence of skeletal muscle fibrosis.(14) Dressman et al. (25) injected the transverse abdominal muscle using rAAV2.CMV.SGCB. Expression persisted for 21 months and muscle fibers were protected from recurrent necrosis. The use of self-complementary AAV to enhance transgene expression,16 a muscle-specific promoter to better target skeletal muscle (20, 26) and the optimization of a human β-sarcoglycan gene (hSGCB) has also been described.

Functional improvement in patients suffering from LGMD and other muscular dystrophies require both gene restoration and reduction of fibrosis. There is a need for methods of reducing fibrosis that may be paired with gene restoration methods for more effective treatments of LGMD and other muscular dystrophies.

SUMMARY

Described herein are gene therapy vectors, e.g. AAV, expressing the β-sarcoglycan gene and methods of delivering β-sarcoglycan to the muscle to reduce and/or prevent fibrosis; and/or to increase muscular force, and/or to treat a mammalian subject suffering from muscular dystrophy.

In one aspect, described herein is a method of treating muscular dystrophy in a subject in need thereof comprising the step of administering a recombinant adeno-associated virus (rAAV) scAAVrh74.MHCK7.hSGCB to a subject in need thereof, wherein the rAAV is administered using a systemic route of administration and at a dose of about $1.0 \times 10^{12}$ vg/kg to about $5.0 \times 10^{14}$ vg/kg based on a supercoiled plasmid as the quantitation standard or $1.0 \times 10^{13}$ vg/kg to about $1.0 \times 10^{14}$ vg/kg based on a linearized plasmid as the quantitation standard; wherein the serum creatine kinase (CK) level in the subject is decreased after administration of the rAAV as compared to serum CK level before administration of the rAAV.

In another aspect, provided is a method of treating muscular dystrophy in a subject in need thereof comprising the step of administering a recombinant adeno-associated virus (rAAV) scAAVrh74.MHCK7.hSGCB, wherein the level of beta-sarcoglycan gene expression in a cell of the subject is increased after administration of the rAAV as compared to the level of beta-sarcoglycan gene expression before administration of the rAAV; wherein the number of beta-sarcoglycan positive fibers in the muscle tissue of the subject is increased after administration of the rAAV as compared to the number of beta-sarcoglycan positive fibers before administration of the rAAV; or wherein motor function is improved in said subject as compared to the motor function of said subject before administration of the rAAV, and wherein the motor function is determined by a 100 meter timed walk test.

In another aspect, this disclosure provides a method of treating a limb-girdle muscular dystrophy in a subject in need, comprising administering to the subject an rAAV intravenous infusion over approximately 1 to 2 hours at a dose of about $5.0 \times 10^{13}$ vg/kg or about $2.0 \times 10^{14}$ vg/kg based on a supercoiled plasmid as the quantitation standard, or about $1.85 \times 10^{13}$ vg/kg or $7.41 \times 10^{13}$ vg/kg based on a linearized plasmid as the quantitation standard, and wherein the rAAV comprises a nucleotide sequence of SEQ ID NO: 3 or SEQ ID NO: 19. In another aspect, the disclosure describes a method of expressing beta-sarcoglycan gene in a subject's cell comprising administering to the subject the scAAVrh74.MHCK7.hSGCB construct that comprises a nucleotide sequence that is at least 90%, 95%, or 99% identical to SEQ ID NO: 19. In one aspect, the disclosure provides a method of increasing beta-sarcoglycan positive fibers and/or decreasing CK level in a subject's muscle tissue comprising administering to the subject the scAAVrh74.MHCK7.hSGCB construct nucleotide sequence that is at least 90%, 95%, or 99% identical to SEQ ID NO: 19.

In one aspect, described herein is a method of increasing the expression of alpha-sarcoglycan in a subject in need thereof comprising administering to the subject an rAAV comprising a scAAVrh74.MHCK7.hSGCB construct with a nucleotide sequence that is at least 90%, 95%, or 99% identical to SEQ ID NO: 3 or SEQ ID NO: 19. In another aspect, provided herein is a method of increasing localization of alpha-sarcoglycan to a cell membrane in a subject in need thereof comprising administering to the subject the scAAVrh74.MHCK7.hSGCB construct nucleotide sequence that is at least 90%, 95%, or 99% identical to SEQ ID NO: 3 or SEQ ID NO: 19. In another aspect, provided is a method of increasing sarcoglycan expression in muscle tissue or improving muscle function of a subject comprising administering to the subject an rAAV comprising a nucleotide sequence that is at least 90%, 95%, or 99% identical to SEQ ID NO: 19. In another aspect, the disclosure provides a method of increasing sarcoglycan expression in muscle tissue of a subject comprising administering to the subject a construct comprising a nucleotide sequence encoding a first sarcoglycan, and detecting increased expression of at least a second sarcoglycan in the cell membrane of the cell expressing said first sarcoglycan.

In another aspect, described is a composition, comprising an rAAV scAAVrh74.MHCK7.hSGCB vector, a buffer agent, an ionic strength agent, and a surfactant. In another aspect, described herein is a pharmaceutical composition comprising a recombinant AAV (rAAV) scAAVrh74.MHCK7.hSGCB, wherein the scAAVrh74.MHCK7.hSGCB comprising a nucleotide sequence that is at least 90%, 95% or 99% identical to SEQ ID NO: 19.

In another aspect, provided is a method of generating a recombinant AAV scAAVrh74.MHCK7.hSGCB, comprising transferring a plasmid to a cell, wherein the plasmid comprises a nucleotide sequence that is at least 90%, 95%, or 99% identical to SEQ ID NO: 24. In particular, the plasmid comprises a nucleotide sequence of SEQ ID NO: 24. In another embodiment, the plasmid comprises a nucleotide sequence of SEQ ID NO: 19.

In another aspect, described here in a recombinant AAV vector comprising a polynucleotide sequence encoding β-sarcoglycan. In some embodiments, the polynucleotide sequence encoding β-sarcoglycan comprises a sequence e.g. at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 1 and encodes protein that retains β-sarcoglycan activity. In some embodiments, the polynucleotide sequence encoding β-sarcoglycan comprises the nucleotide sequence set forth in SEQ ID NO: 1. In some embodiments, the polynucleotide sequence encoding β-sarcoglycan consists of the nucleotide sequence set forth in SEQ ID NO: 1.

In another aspect, a recombinant AAV vector described herein comprises a polynucleotide sequence encoding β-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the amino acid sequence of SEQ ID NO: 2, and the protein retains β-sarcoglycan activity.

In another aspect, described herein is a recombinant AAV vector comprising a polynucleotide sequence encoding functional β-sarcoglycan that comprises a nucleotide sequence that hybridizes under stringent conditions to the nucleic acid sequence of SEQ ID NO: 1, or a complement thereof.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

When ranges are used herein for physical properties, such as molecular weight, concentration, or dosage, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

In another aspect, the recombinant AAV vectors described herein may be operably linked to a muscle-specific control element. For example the muscle-specific control element is human skeletal actin gene element, cardiac actin gene element, myocyte-specific enhancer binding factor MEF, muscle creatine kinase (MCK), tMCK (truncated MCK), myosin heavy chain (MHC), MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypozia-inducible nuclear factors, steroid-inducible element or glucocorticoid response element (GRE).

In some embodiments, the muscle-specific promoter is MHCK7 (SEQ ID NO: 4). An exemplary rAAV described herein is pAAV.MHCK7.hSCGB which comprises the nucleotide sequence of SEQ ID NO: 3. Within the nucleotide sequence of SEQ ID NO: 3, the MCHK7 promoter spans nucleotides 130-921, a SV40 chimeric intron (SEQ ID NO: 20) spans nucleotides 931-1078, the β-sarcoglycan sequence (SEQ ID NO: 1) spans nucleotides 1091-2047 and the poly A (SEQ ID NO: 21) spans nucleotides 2054-2106. In some embodiments, the rAAV pAAV.MHCK7.hSCGB comprises a nucleotide sequence of SEQ ID NO: 19. Within the nucleotide sequence of SEQ ID NO: 19, the MCHK7 promoter spans nucleotides 128-919, a SV40 chimeric intron spans nucleotides 929-1076, the β-sarcoglycan sequence spans nucleotides 1086-2042 and the poly A spans nucleotides 2049-2101.

In some embodiments, the rAAV pAAV.MHCK7.hSCGB comprises a nucleotide sequence that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to the nucleotide sequence set forth in SEQ ID NO: 3 or SEQ ID NO: 19, or a nucleotide sequence that encodes a polypeptide that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to SEQ ID NO: 2.

In one embodiment, the polynucleotide sequence encodes a protein that retains sarcoglycan activity, including beta- and/or alpha-sarcoglycan activity. In another embodiment, the polynucleotide sequence encodes a protein that retains beta-sarcoglycan activity.

In some embodiments, the muscle-specific promoter is tMCK (SEQ ID NO: 6). An exemplary rAAV described herein is pAAV.tMCK.hSCGB which comprises the nucleotide sequence of SEQ ID NO: 5. Within the nucleotide sequence of SEQ ID NO: 5, the tMCK promoter spans nucleotides 141-854, an SV40 chimeric intron spans nucleotides 886-1018, the β-sarcoglycan sequence spans nucleotides 1058-2014 and the poly A spans nucleotides 2021-

2073. In some embodiments, the polynucleotide sequence encoding a pAAV.tMCK.hSCGB comprises a sequence e.g. at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% or more identical to the nucleotide sequence set forth in SEQ ID NO: 5, wherein the polynucleotide sequence encodes a protein that retains sarcoglycan activity, including but not limited to, beta- and/or alpha-sarcoglycan activity.

The AAV can be any serotype, for example AAV1, AAV2, AAV3, AAV4, AAV5, AAV6, AAV7, AAV8, AAV9, AAV-10, AAV-11, AAV-12, AAV-13 and AAVrh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

Compositions comprising any of the rAAV vectors described herein are also contemplated.

In some embodiments, the disclosure provides a composition or pharmaceutical composition that comprises an scAAVrh74.MHCK7.hSCGB rAAV vector comprising a nucleotide sequence that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to the nucleotide sequence set forth in SEQ ID NO: 3 or SEQ ID NO: 19, or comprising a nucleotide sequence that encodes a polypeptide that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to SEQ ID NO: 2. In addition, the disclosure provides a provides a composition or pharmaceutical composition that comprises an scAAVrh74.MHCK7.hSCGB rAAV vector comprising a nucleotide sequence of SEQ ID NO: 3 or SEQ ID NO: 19, or comprising a nucleotide sequence that encodes a polypeptide comprising the amino acid sequence of SEQ ID NO: 2.

Provided are methods of treating muscular dystrophy in a subject in need thereof comprising the step of administering a recombinant adeno-associated virus (rAAV) scAAVrh74.MHCK7.hSGCB, wherein the rAAV is administered using a systemic route of administration and at a dose of about $1.0 \times 10^{12}$ vg/kg to about $5.0 \times 10^{14}$ vg/kg.

Also provided are composition for treating muscular dystrophy, wherein the composition comprises a recombinant adeno-associated virus (rAAV) scAAVrh74.MHCK7.hSGC at a dose of about $1.0 \times 10^{12}$ vg/kg to about $5.0 \times 10^{14}$ vg/kg and the composition is formulated for systemic administration.

In addition, provided are uses of a recombinant adeno-associated virus (rAAV) scAAVrh74.MHCK7.hSGC for the preparation of a medicament for treating muscular dystrophy, wherein the medicament comprises scAAVrh74.MHCK7.hSGC at a dose of about $1.0 \times 10^{12}$ vg/kg to about $5.0 \times 10^{14}$ vg/kg and the medicament is formulated for systemic administration.

In any of the provided methods, compositions and uses, the level of beta-sarcoglycan gene expression in a cell of the subject is increased after administration of the rAAV as compared to the level of beta-sarcoglycan gene expression before administration of the rAAV; wherein the serum creatine kinase (CK) level in the subject is decreased after administration of the rAAV as compared to serum CK level before administration of the rAAV; and/or wherein the number of beta-sarcoglycan positive fibers in the muscle tissue of the subject is increased after administration of the rAAV as compared to the number of beta-sarcoglycan positive fibers before administration of the rAAV.

In another embodiment, in any of the provided methods, compositions and uses, motor function is improved in said subject as compared to the motor function of said subject before administration of the rAAV, and wherein the motor function is determined by a 100 meter timed walk test. For example, motor function is improved by at least 5% in 1 month or thirty days post-gene transfer, at least 10% in 2 months or sixty days post-gene transfer, or at least 15% in 3 months or ninety days post gene transfer. In some embodiments, the motor function is improved by at least 5%, 10%, 15%, 20%, 25%, 30%, 40%, 45%, or 50%.

For example, in any of the provided methods, compositions and uses, the systemic route of administration is an intravenous route. For example, the rAAV is administered using an intravenous route and the dose of the rAAV administered is about $1.85 \times 10^{13}$ vg/kg or about $7.41 \times 10^{13}$ vg/kg based on a linearized plasmid as the quantification standard or the dose of the rAAV administered is about $5 \times 10^{13}$ vg/kg or about $2 \times 10^{14}$ vg/kg based on a supercoiled plasmid as the quantification standard.

In some embodiments, the dose of rAAV administered using an intravenous route and the dose is about $1.0 \times 10^{13}$ vg/kg to about $5 \times 10^{14}$ based on a supercoiled plasmid as the quantitation standard or about $1.0 \times 10^{13}$ vg/kg to about $1.0 \times 10^{14}$ vg/kg based on a linearized plasmid as the quantitation standard.

In addition, the dose of the rAAV administered is about $1.5 \times 10^{13}$ vg to about $2 \times 10^{16}$ vg, or $1.5 \times 10^{13}$ vg to $1 \times 10^{16}$ vg, or about $1.5 \times 10^{13}$ vg to about $2 \times 10^{15}$ vg, or about $1.5 \times 10^{13}$ vg to about $1 \times 10^{15}$ vg. In addition, in any of the methods, compositions and uses, the dose of rAAV is administered at a concentration of about 10 mL/kg. In any of the methods, compositions or uses provided, the muscular dystrophy is limb-girdle muscular dystrophy.

In addition, provided are methods of treating muscular dystrophy in a subject in need thereof comprising the step of administering a recombinant adeno-associated virus (rAAV) scAAVrh74.MHCK7.hSGCB, wherein the rAAV is administered using a systemic route of administration and at a dose of about $1.0 \times 10^{12}$ vg/kg to about $5.0 \times 10^{14}$ vg/kg; wherein the level of beta-sarcoglycan gene expression in a cell of the subject is increased after administration of the rAAV as compared to the level of beta-sarcoglycan gene expression before administration of the rAAV; wherein the serum CK level in the subject is decreased after administration of the rAAV as compared to serum CK level before administration of the rAAV; or wherein the number of beta-sarcoglycan positive fibers in the muscle tissue of the subject is increased after administration of the rAAV as compared to the number of beta-sarcoglycan positive fibers before administration of the rAAV. For example, in any of the provided methods, the systemic route of administration is an intravenous route and the dose of the rAAV administered is about $5.0 \times 10^{13}$ vg/kg based on a supercoiled plasmid as the quantitation standard. In another embodiment, the dose of the rAAV administered is about $2.0 \times 10^{14}$ vg/kg based on a supercoiled plasmid as the quantitation standard. In another embodiment, the dose of the rAAV administered is about $7.41 \times 10^{13}$ vg/kg based on a linearized plasmid as the quantitation standard. In another embodiment, the dose of rAAV administered is about $1.85 \times 10^{13}$ vg/kg based on a linearized plasmid as the quantitated standard. In addition, the dose of the rAAV administered is about $1.5 \times 10^{13}$ vg to about $2 \times 10^{16}$ vg, or $1.5 \times 10^{13}$ vg to $1 \times 10^{16}$ vg, or about $1.5 \times 10^{13}$ vg to about $2 \times 10^{15}$ vg, or about $1.5 \times 10^{13}$ vg to about $1 \times 10^{5}$ vg. In addition, in any of the methods, the dose of rAAV is administered at a concentration of about 10 mL/kg. In any of the methods provided, the muscular dystrophy is limb-girdle muscular dystrophy.

In some embodiments, the disclosure includes a method of treating muscular dystrophy in a subject in need thereof comprising the step of administering a recombinant adeno-associated virus (rAAV) scAAVrh74.MHCK7.hSGCB, wherein motor function is demonstrably improved in said subject as compared to motor function of said subject before administration of the rAAV, and wherein motor function is determined by a 100 m timed walk test. In some aspects, motor function is improved by at least 5% in 1 month or thirty days post-gene transfer, at least 10% in 2 months or sixty days post-gene transfer, or at least 15% in 3 months or ninety days post gene transfer. In some aspects, motor function is improved by at least about 5%, about 10%, about 15%, about 20%, about 25%, about 30%, about 40%, about 45%, or about 50%.

Provided are methods of increasing the level of alpha-sarcoglycan in a subject in need thereof comprising administering to the subject the scAAVrh74.MHCK7.hSGCB construct that comprises a nucleotide sequence of SEQ ID NO: 3 or SEQ ID NO: 19. In addition, provided are composition for increasing the level of alpha-sarcoglycan in a subject in need, wherein the composition comprises scAAVrh74.MHCK7.hSGCB construct comprising a nucleotide sequence of SEQ ID NO: 3 or SEQ ID NO: 19. Also provides are uses of scAAVrh74.MHCK7.hSGCB construct that comprises a nucleotide sequence of SEQ ID NO: 3 or SEQ ID NO: 19 for the preparation of a medicament for increasing the level of alpha-sarcoglycan in a subject in need thereof. In some aspects, the alpha-sarcoglycan is colocalized to the membrane of a cell expressing a beta-sarcoglycan encoded by scAAVrh74.MHCK7.hSGCB.

In some embodiments, the scAAVrh74.MHCK7.hSGCB construct comprises an intron sequence. In one embodiment, the intron sequence comprise a nucleotide sequence of SEQ ID NO: 20. In another embodiment, the scAAVrh74.MHCK7.hSGCB construct comprises a polyA sequence. In one embodiment, the poly A sequence comprises a nucleotide sequence of SEQ ID NO: 21. In another embodiment, the scAAVrh74.MHCK7.hSGCB construct comprises a 5' inverted terminal repeat (ITR) sequence. In one embodiment, the 5'ITR sequence comprises a nucleotide sequence of SEQ ID NO: 22. In another embodiment, the scAAVrh74.MHCK7.hSGCB construct comprises a 3' inverted terminal repeat (ITR) sequence. In one embodiment, the 3'ITR sequence comprises a nucleotide sequence of SEQ ID NO: 23.

Also provided are methods of increasing sarcoglycan expression in muscle tissue of a subject comprising administering to the subject a construct comprising a nucleotide sequence encoding a first sarcoglycan, and detecting increased expression of at least a second sarcoglycan in the cell membrane of the cell expressing said first sarcoglycan. In some aspects, the first sarcoglycan is β-sarcoglycan (SGCB), and said second sarcoglycan is α-sarcoglycan (SGCA), γ-sarcoglycan (SGCG), or δ-sarcoglycan (SGCD).

In any of the methods, uses and compositions of treating muscular dystrophy provided, the subject is 4-15 years of age, has confirmed beta-sarcoglycan (SGCB) mutation in both alleles, was negative for AAVrh74 antibodies and/or had >40% or normal 100 meter walk test. In any of the methods, uses and compositions of treating muscular dystrophy provided, the subject is a pediatric subject. In some embodiments, the subject is a pediatric subject, such as a subject ranging in age from 1 to 10 years. In some embodiments, the subject is 4 to 15 years of age. The subject, in on embodiment, is an adolescent subject, such as a subject ranging in age from 10 to 19 years. In addition, the subject, in on embodiment, is a young adult subject such as a subject ranging in age from late teens or early twenties, such as the subject may range in age from 15 to 29 years of age. In some embodiment, the subject is a middle-aged adult or an elderly subject, such that the middle-aged adult may range in age from 25-55 years of age and the elderly subject may range in age over 50 years of age.

In some embodiments, the rAAV is administered by injection, infusion or implantation. For example, the rAAV is administered by infusion over approximately 1 to 2 hours. In addition, the rAAV is administered by an intravenous route through a peripheral limb vein.

In the methods of treating muscular dystrophy in a subject in need thereof comprising the step of administering a recombinant adeno-associated virus (rAAV) scAAVrh74.MHCK7.hSGCB, wherein the rAAV is administered using a systemic route of administration and at a dose of about $1.0 \times 10^{12}$ vg/kg to about $5.0 \times 10^{14}$ vg/kg based on a supercoiled plasmid as the quantitation standard and the rAAV comprises the human β-sarcoglycan nucleotide sequence of SEQ ID NO: 1. In addition, the rAAV comprises the MHCK7 promoter sequence of SEQ ID NO: 4. In some embodiments, the rAAV is of the serotype AAVrh.74. In addition, the rAAV comprises the scAAVrh74.MHCK7.hSGCB construct nucleotide sequence of SEQ ID NO: 3 or SEQ ID NO: 19.

In another embodiment, the scAAVrh74.MHCK7.hSGCB construct comprises an intron sequence. In one embodiment, the intron sequence comprise a nucleotide sequence of SEQ ID NO: 20. In another embodiment, the scAAVrh74.MHCK7.hSGCB construct comprises a polyA sequence. In one embodiment, the poly A sequence comprises a nucleotide sequence of SEQ ID NO: 21. In another embodiment, the scAAVrh74.MHCK7.hSGCB construct comprises a 5' inverted terminal repeat (ITR) sequence. In one embodiment, the 5'ITR sequence comprises a nucleotide sequence of SEQ ID NO: 22. In another embodiment, the scAAVrh74.MHCK7.hSGCB construct comprises a 3' inverted terminal repeat (ITR) sequence. In one embodiment, the 3'ITR sequence comprises a nucleotide sequence of SEQ ID NO: 23.

In an exemplary embodiment, methods of treating muscular dystrophy in a subject in need thereof comprise the step of administering a recombinant adeno-associated virus (rAAV) scAAVrh74.MHCK7.hSGCB, wherein the rAAV is administered using a systemic route of administration and at a dose of about $1.0 \times 10^{12}$ vg/kg to about $5.0 \times 10^{14}$ vg/kg, wherein the subject is suffering from limb-girdle muscular dystrophy, and the rAAV is administered by intravenous infusion over approximately 1 to 2 hours at a dose of about $5.0 \times 10^{13}$ vg/kg or about $2.0 \times 10^{14}$ vg/kg based on a supercoiled plasmid as the quantitation standard, or about $1.85 \times 10^{13}$ vg/kg or $7.41 \times 10^{13}$ vg/kg based on a linearized plasmid as the quantitation standard, and wherein the rAAV comprises the scAAVrh74.MHCK7.hSGCB construct nucleotide sequence of SEQ ID NO: 3 or SEQ ID NO: 19.

In addition, the disclosure provides a composition for treating limb-girdle muscular dystrophy comprising a dose of recombinant adeno-associated virus (rAAV) scAAVrh74.MHCK7.hSGCB, wherein the rAAV comprises the scAAVrh74.MHCK7.hSGCB construct nucleotide sequence of SEQ ID NO: 3 or SEQ ID NO: 19, and the composition is formulated to deliver a dose of about $5.0\times10^{13}$ vg/kg or about $2.0\times10^{14}$ vg/kg based on a supercoiled plasmid as the quantitation standard, or about $1.85\times10^{13}$ vg/kg or about $7.41\times10^{13}$ vg/kg based on a linearized plasmid as the quantitation standard by intravenous infusion over approximately 1 to 2 hours.

The disclosure also provides for use of a dose of recombinant adeno-associated virus (rAAV) scAAVrh74.MHCK7.hSGCB for the preparation of a medicament for the treatment of limb-girdle muscular dystrophy, wherein the dose of rAAV about $5.0\times10^{13}$ vg/kg or about $2.0\times10^{14}$ vg/kg based on a supercoiled plasmid as the quantitation standard, or about $1.85\times10^{13}$ vg/kg or about $7.41\times10^{13}$ vg/kg based on a linearized plasmid as the quantitation standard and the medicament is formulated to deliver the dose by intravenous infusion over approximately 1 to 2 hours.

The disclosure further provides a method of improving muscle function of a subject comprising administering to the subject a construct comprising a nucleotide sequence with at least 90% identity, at least 95% identity, at least 99% identity, or 100% identity to SEQ ID NO: 1, 3, 5, or 19. In addition, provided are composition for improving muscle function of a subject, wherein the composition comprises a construct comprising a nucleotide sequence with at least 90% identity, at least 95% identity, at least 99% identity or 100% identity to SEQ ID NO: 1, 3, 5, or 19. Also provides are uses of a construct comprising a nucleotide sequence with at least 90% identity, at least 95% identity, at least 99% identity or 100% identity to SEQ ID NO: 1, 3, 5, or 19 for the preparation of a medicament for improving muscle function of a subject.

In any of the provided methods uses or compositions, the subject suffers from a genetic mutation in a gene encoding a sarcoglycan or a muscular dystrophy. In some aspects, the sarcoglycan is β-sarcoglycan (SGCB), α-sarcoglycan (SGCA), γ-sarcoglycan (SGCG), or δ-sarcoglycan (SGCD). In some aspects, the sarcoglycan is β-sarcoglycan or α-sarcoglycan.

In any of the provided methods, uses or compositions, the level of beta-sarcoglycan gene expression in a cell of the subject is increased after administration of the rAAV as compared to the level of beta-sarcoglycan gene expression before administration of the rAAV.

In addition, in any of the provided methods, uses or compositions, the expression of the beta-sarcoglycan gene in the cell is detected by measuring the beta-sarcoglycan protein level on a Western blot or immunohistochemistry in muscle biopsied before and after administration of the rAAV.

In any of the provided methods, uses or compositions, the level of beta-sarcoglycan protein is increased by at least 25%, or at least 26%, or at least 27%, or at least 28%, or at least 29%, or at least 30%, or at least 31%, or at least 32%, or at least 33%, or at least 34%, or at least or 35% or at least 36%, or at least 37%, or at least 38%, or at least 39%, or at least 40%, or at least 41%, or at least 42%, or at least 43%, or at least 44%, or at least 45% or at least 46%, or at least 47%, or at least 48%, or at least 49%, or at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 85%, or at least 90% or at least 95%, or at least 98% after administration of rAAV. For example, the level of the level of beta-sarcoglycan protein is increased by at least 33% as detected by measuring the beta-sarcoglycan protein level on a Western blot in muscle biopsied before and after administration of the rAAV, or the level of beta-sarcoglycan protein is increased by at least 38% or at least 39% as detected by measuring the beta-sarcoglycan protein level by immunohistochemistry in muscle biopsies before and after administration of the rAAV In any of the methods, uses or compositions provided herein, the serum CK level in the subject is decreased after administration of the rAAV as compared to serum CK level before administration of the rAAV. For example, the serum level CK level in the subject is decreased by at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 81%, or at least 82%, or at least 83%, or at least 84%, or at least 85%, or at least 86% or at least 87%, or at least 88%, or at least 89%, or at least 90% or at least 95%, or at least 98% by 60 to 90 days or 60 days or 90 days after administration of rAAV as compared to the serum CK level before administration of the rAAV.

In any of the methods, uses or compositions provided herein, the number of beta-sarcoglycan positive fibers in the muscle tissue of the subject is increased after administration of the rAAV as compared to the number of beta-sarcoglycan positive fibers before administration of the rAAV. For example, the number of beta-sarcoglycan positive fibers is detected by measuring the beta-sarcoglycan protein level by Western blot or immunohistochemistry on muscle biopsies before and after administration of the rAAV. For example, the number of beta-sarcoglycan positive fibers in the muscle tissue of the subject is increased by at least 25%, or at least 26%, or at least 27%, or at least 28%, or at least 29%, or at least 30%, or at least 31%, or at least 32%, or at least 33%, or at least 34%, or at least 35% or at least 36%, or at least 37%, or at least 38%, or at least 39%, or at least 40%, or at least 41%, or at least 42%, or at least 43%, or at least 44%, or at least 45% or at least 46%, or at least 47%, or at least 48%, or at least 49%, or at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 85%, or at least 90% or at least 95%, or at least 98% after administration of rAAV.

In any of the methods, compositions and uses provided herein, the level of alpha-sarcoglycan in the subject is increased after administration of the rAAV as compared to the level of alpha-sarcoglycan before administration of the rAAV. The level of alpha-sarcoglycan is detected by measuring the alpha-sarcoglycan protein level by immunohistochemistry or Western blot on muscle biopsies before and after administration of the rAAV.

Another embodiment provides for methods expressing beta-sarcoglycan gene in a cell comprising administering to the subjects the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

Also provided are compositions for expressing beta-sarcoglycan gene in a cell, wherein the composition comprises the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

The disclosure also provides for uses of the scAAVrh74.MHCK7.hSGCB construct nucleotide sequence for the preparation of a medicament for the expressing beta-sarcoglycan gene in a cell, wherein the scAAVrh74.MHCK7.hSGCB construct nucleotide sequence is at least 90%, 95%, or 99% identical to SEQ ID NO: 3 or SEQ ID NO: 19 or comprising the nucleotide sequence of SEQ ID NO: 3 or SEQ ID NO: 19.

In any of the provided methods, uses or compositions for expressing beta-sarcoglycan gene in a cell, expression of the beta-sarcoglycan gene in the cell is detected by measuring the beta-sarcoglycan protein level on a Western blot or immunohistochemistry in muscle biopsies before and after administration of the scAAVrh74.MHCK7.hSGCB construct. For example, the cell has more than one AAV viral copy number. In addition, the beta-sarcoglycan gene is measured in the subject by detecting greater than 1 rAAV vector genome copy per nucleus.

Also provided are compositions for decreasing serum CK levels in a subject in need thereof, wherein the composition comprises the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

The disclosure also provides for uses of the scAAVrh74.MHCK7.hSGCB construct nucleotide sequence for the preparation of a medicament for decreasing serum CK levels in a subject in need thereof, wherein the scAAVrh74.MHCK7.hSGCB construct nucleotide sequence is at least 90%, 95%, or 99% identical to SEQ ID NO: 3 or SEQ ID NO: 19 or comprising the nucleotide sequence of SEQ ID NO: 3 or SEQ ID NO: 19.

In any of these methods, uses, and compositions, the serum CK level in the subject is decreased by at least 82% by 60 days after administration of the rAAV as compared to the serum CK level before administration of the rAAV.

Methods of increasing beta-sarcoglycan positive fibers in a muscle tissue of a subject comprising administering to the subject the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19 are provided.

Also provided are compositions for increasing beta-sarcoglycan positive fibers in muscle tissue of a subject, wherein the composition comprises the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

The disclosure also provides for uses of the scAAVrh74.MHCK7.hSGCB construct nucleotide sequence for the preparation of a medicament for increasing beta-sarcoglycan positive fibers in muscle tissue of a subject, wherein the scAAVrh74.MHCK7.hSGCB construct nucleotide sequence is at least 90%, 95%, or 99% identical to SEQ ID NO: 3 or SEQ ID NO: 19 or comprising the nucleotide sequence of SEQ ID NO: 3 or SEQ ID NO: 19.

In any of these methods, uses, and compositions, the number of beta-sarcoglycan positive fibers is detected by measuring the beta-sarcoglycan protein level by Western blot or immunohistochemistry on muscle biopsies before and after administration of the rAAV. In addition, in any of the methods, uses and compositions, the number of beta-sarcoglycan positive fibers is measured by detecting greater than 1 rAAV vector genome copy per nucleus.

Another embodiment provides for methods of increasing the expression of alpha-sarcoglycan in a subject in need thereof comprising administering to the subject the scAAVrh74.MHCK7.hSGCB construct that comprises a nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

Also provided are compositions for increasing the expression of alpha-sarcoglycan in a subject in need thereof, wherein the composition comprises the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

The disclosure also provides for uses of the scAAVrh74.MHCK7.hSGCB construct nucleotide sequence for the preparation of a medicament for increasing the expression of alpha-sarcoglycan in a subject, wherein the scAAVrh74.MHCK7.hSGCB construct nucleotide sequence is at least 90%, 95%, or 99% identical to SEQ ID NO: 3 or SEQ ID NO: 19 or comprising the nucleotide sequence of SEQ ID NO: 3 or SEQ ID NO: 19.

Also provided are methods of increasing localization of alpha-sarcoglycan to a cell membrane in a subject in need thereof comprising administering to the subject the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

Also provided are compositions for increasing localization of alpha-sarcoglycan to a cell membrane in a subject in need thereof, wherein the composition comprises the scAAVrh74.MHCK7.hSGCB construct nucleotide sequence that is at least 90%, 95%, or 99% identical to SEQ ID NO: 3 or SEQ ID NO: 19 or comprising the nucleotide sequence of SEQ ID NO: 3 or SEQ ID NO: 19.

The disclosure also provides for uses of the scAAVrh74.MHCK7.hSGCB construct nucleotide sequence for the preparation of a medicament for increasing localization of alpha-sarcoglycan to a cell membrane in a subject in need thereof, wherein the scAAVrh74.MHCK7.hSGCB construct nucleotide sequence is at least 90%, 95%, or 99% identical to SEQ ID NO: 3 or SEQ ID NO: 19 or comprising the nucleotide sequence of SEQ ID NO: 3 or SEQ ID NO: 19.

In any of these methods, uses and compositions the level of alpha-sarcoglycan is detected by measuring the alpha-sarcoglycan protein level by Western blot or immunohistochemistry on muscle biopsies before and after administration of the rAAV. In addition, in any of the provided methods, uses and compositions, alpha-sarcoglycan is colocalized to the membrane of a cell expressing a beta-sarcoglycan encoded by scAAVrh74.MHCK7.hSGCB.

Another embodiment provides for methods of increasing sarcoglycan expression in muscle tissue of a subject in need thereof, comprising administering to the subject the scAAVrh74.MHCK7.hSGCB construct that comprises a nucleotide sequence that is at least 90%, 95%, or 99% identical to SEQ ID NO: 1, SEQ ID NO: 3, SEQ ID NO: 5 or SEQ ID NO: 19 or comprising the nucleotide sequence of SEQ ID NO: 1, SEQ ID NO: 3, SEQ ID NO: 5 or SEQ ID NO: 19.

Also provided are compositions for increasing the expression of sarcoglycan expression in muscle tissue of a subject in need thereof, wherein the composition comprises the scAAVrh74.MHCK7.hSGCB construct nucleotide sequence that is at least 90%, 95%, or 99% identical to SEQ ID NO: 1, SEQ ID NO: 3, SEQ ID NO: 5 or SEQ ID NO: 19 or comprising the nucleotide sequence of SEQ ID NO: 1, SEQ ID NO: 3, SEQ ID NO: 5 or SEQ ID NO: 19.

The disclosure also provides for uses of the scAAVrh74.MHCK7.hSGCB construct nucleotide sequence for the preparation of a medicament for increasing sarcoglycan expression in muscle tissue of a subject in need thereof, wherein the scAAVrh74.MHCK7.hSGCB construct nucleotide sequence is at least 90%, 95%, or 99% identical to SEQ ID NO: 1, SEQ ID NO: 3, SEQ ID NO: 5 or SEQ ID NO: 19 or comprising the nucleotide sequence of SEQ ID NO: 1, SEQ ID NO: 3, SEQ ID NO: 5 or SEQ ID NO: 19.

In any of these methods, uses and compositions for increasing sarcoglycan expression in muscle tissue, the subject suffers from a genetic mutation in a gene encoding a sarcoglycan or a muscular dystrophy. For example in any of these methods, uses or compositions, the sarcoglycan is β-sarcoglycan (SGCB), α-sarcoglycan (SGCA), γ-sarcoglycan (SGCG), or δ-sarcoglycan (SGCD).

Methods of producing a recombinant AAV vector particle comprising culturing a cell that is transferred with a plasmid described herein and recovering recombinant AAV particles from the supernatant of the transfected cells are also provided. Viral particles comprising any of the recombinant AAV vectors described herein are also contemplated. In one embodiment, the method of generating the rAAV comprising transferring an AAV vector plasmid to a host cell. In another embodiment, the plasmid comprises a nucleotide sequence that is at least 90%, 95%, or 99% identical to SEQ ID NO: 24. In another aspect, the disclosure provides a cell that comprising an AAV vector plasmid that comprises a nucleotide sequence of SEQ ID NO: 24. The cell described herein comprises an insect cell, e.g., a *Drosophila* cell (e.g., an S2 cell or Kc cell), a silkworm cell (e.g., a Bme21 cell), or a mosquito cell (e.g., a C6/36 cell); or a mammalian cell (preferably a human cell, e.g., a human primary cell or an established cell line). In one embodiment, the mammalian cell comprises a 293 cell, a COS cell, a HeLa cells, or a KB cell.

In another embodiment, the plasmid comprises a nucleotide sequence that is at least 90%, 95%, or 99% identical to SEQ ID NO: 1, 3, 5, or 19. In some embodiments, the the vector plasmid comprises a nucleotide sequence of any one of SEQ ID NO: 1, 3, 5, or 19. In some embodiments, the AAV vector plasmid is stably expressed in the host cell. The host cell stably harboring the AAV vector plasmid can be used to generate rAAV. In one embodiment, the AAV vector plasmid is a pAAV.MHCK7.hSGCB. KAN plasmid.

The method of producing recombinant AAV vector particles provided herein may further comprise a step of transferring a packaging plasmid and/or a helper virus to the host cell. For example, the methods further comprise a step wherein the packaging cell comprises a stably integrated AAV cap gene and/or wherein the packaging cell comprises a stably integrated AAV rep gene. The invention also provides for a cell comprising a plasmid that comprises a nucleotide sequence that is at least 90%, 95%, or 99% identical to SEQ ID NO: 24 or an plasmid that comprises a nucleotide sequence of SEQ ID NO: 24. Also provides is a cell comprising a nucleotide sequence of SEQ ID NO: 1, 3, 5, or 19.

Methods of reducing fibrosis in a mammalian subject in need thereof is also provided. In this regard, the method comprises administering a therapeutically effective amount of an AAV vector described herein (or composition comprising an AAV vector described herein) to the mammalian subject. In some embodiments, the mammalian subject suffers from muscular dystrophy. In some embodiments, administration of an AAV vector described herein (or composition comprising an AAV vector described herein) reduces fibrosis in skeletal muscle or in cardiac muscle of the subject.

The term "muscular dystrophy" as used herein refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type 1D congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 2I muscular dystrophy, limb-girdle type 2I muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In some embodiments, the subject is suffering from limb-girdle muscular dystrophy. In some embodiments, the subject is suffering from limb-girdle muscular dystrophy type 2E (LGMD2E).

The term "fibrosis" as used herein refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include collagen, e.g. collagen 1, collagen 2 or collagen 3, and fibronectin.

In another aspect, described herein is a method of increasing muscular force and/or muscle mass in a mammalian subject comprising administering a therapeutically effective amount of an AAV vector described herein (or composition comprising an AAV vector described herein) to the mammalian subject. In one embodiment, the subject is a human.

In any of the methods of the invention, the subject may be suffering from muscular dystrophy such as limb-girdle muscular dystrophy or any other dystrophin-associated muscular dystrophy.

Also provided is a method of treating muscular dystrophy in a mammalian subject comprising administering a therapeutically effective amount of an AAV vector described herein (or composition comprising an AAV vector described herein) to the mammalian subject. In some embodiments, the muscular dystrophy is limb-girdle muscular dystrophy.

In any of the methods of the invention, the rAAV is administered by intramuscular injection or intravenous injection. In addition, in any of the method of the invention, the rAAV is administered systemically, such as parental administration by injection, infusion or implantation.

The compositions of the invention are formulated for intramuscular injection or intravenous injection. In addition, the compositions of the invention are formulated for systemic administration, such as parental administration by injection, infusion or implantation.

In addition, any of the compositions formulated for administration to a subject suffering from muscular dystrophy (such as limb-girdle muscular dystrophy or any other dystrophin-associated muscular dystrophy). In some embodiments, the composition may further comprise a second recombinant AAV vector comprising a polynucleotide sequence set forth in SEQ ID NO: 9 or SEQ ID NO: 8.

In any of the uses of the invention, the medicament is formulated for intramuscular injection or intravenous injection. In addition, in any of the uses of the invention, the medicament is formulated for systemic administration, such as parental administration by injection, infusion or implantation. In addition, any of the medicaments may be prepared for administration to a subject suffering from muscular dystrophy (such as limb-girdle muscular dystrophy or any other dystrophin associated muscular dystrophy). In some embodiments, the medicament may further comprise a second recombinant AAV vector comprising a polynucleotide sequence set forth in SEQ ID NO: 9 or SEQ ID NO: 8.

The invention also provides for a formulation or composition, comprising an rAAV virion that comprises an AAVrh74 derived capsid, a buffer agent, an ionic strength agent, and a surfactant. In the provided formulation or composition, the rAAV is at a concentration of about $1.0 \times 10^{12}$ vg/ml to about $5.0 \times 10^{14}$ vg/ml or at a concentration of about $5.0 \times 10^{12}$ vg/ml to about $1.0 \times 10^{14}$ vg/ml. In addition, the rAAV is at a concentration of about $2.0 \times 10^{13}$ vg/ml, $4 \times 10^{13}$ vg/ml, or $5 \times 10^{13}$ vg/ml. In the provided formations or compositions, the rAAV may be an scAAVrh74.MHCK7.hSGCB viral particle or an scAAVrh74.MHCK7.hSGCB vector. For example, in any of the provided formulations or compositions scAAVrh74.MHCK7.hSGCB comprises a nucleotide sequence of SEQ ID NO: 19.

In any of the provided formulations or compositions, the buffer agent comprises one or more of tris, tricine, Bis-tricine, HEPES, MOPS, TES, TAPS, PIPES, and CAPS. For example, the buffer agent comprises the tris with pH 8.0 at concentration of about 5 mM to about 40 mM or the buffer agent comprises the tris with pH 8.0 at about 20 mM.

In any of the provided formulations or compositions, the ionic strength agent comprises one or more of potassium chloride (KCl), potassium acetate, potassium sulfate, ammonium sulfate, ammonium chloride (NH$_4$Cl), ammonium acetate, magnesium chloride (MgCl$_2$), magnesium acetate, magnesium sulfate, manganese chloride (MnCl$_2$), manganese acetate, manganese sulfate, sodium chloride (NaCl), sodium acetate, lithium chloride (LiCl), and lithium acetate. For example, the ionic strength agent comprises MgCl$_2$ at a concentration of about 0.2 mM to about 4 mM or the ionic strength agent comprises NaCl at a concentration of about 50 mM to about 500 mM, or the ionic strength agent comprises MgCl$_2$ at a concentration of about 0.2 mM to about 4 mM and NaCl at a concentration of about 50 mM to about 500 mM, or the ionic strength agent comprises MgCl$_2$ at a concentration of about 1 mM and NaCl at a concentration of about 200 mM.

In any of the provided formulations or compositions, the surfactant comprises one or more of a sulfonate, a sulfate, a phosphonate, a phosphate, a Poloxamer, and a cationic surfactant. For example, the Poloxamer comprises one or more of Poloxamer 124, Poloxamer 181, Poloxamer 184, Poloxamer 188, Poloxamer 237, Poloxamer 331, Poloxamer 338, and Poloxamer 407. The Poloxamer may be at a concentration of about 0.00001% to about 1%. An exemplary surfactant is Poloxamer 188 at a concentration of about 0.001%.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

DETAILED DESCRIPTION

Figure 1:
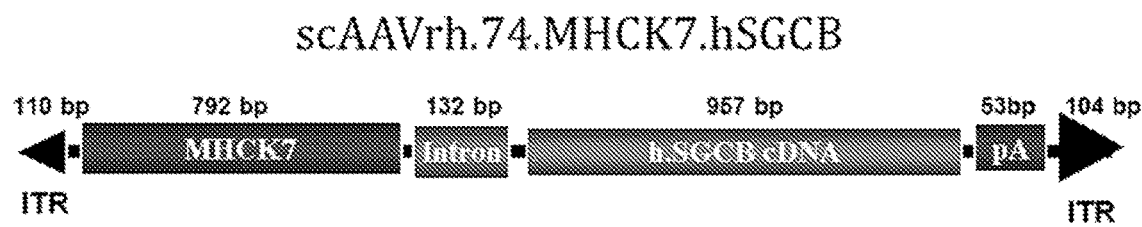
FIG. 1 provides a schematic of therapeutic β-sarcoglycan transgene cassette. Self-complementary AAV vector containing the codon-optimized human β-sarcoglycan gene (hSGCB). A muscle specific MHCK7 promoter drives expression. The cassette also contains a chimeric intron to augment processing and polyadenylation signal for stability.

The present disclosure is based on the discovery that administration of an AAV vector comprising a polynucleotide expressing β-sarcoglycan results in a reduction or complete reversal of muscle fibrosis in a limb-girdle muscular dystrophy animal model. As demonstrated in the Examples, administration of the AAV vector described herein resulted in the reversal of dystrophic features including fewer degenerating fibers, reduced inflammation and improved functional recovery by protection against eccentric contraction with increased force generation.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion," or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV

Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote skeletal muscle specific expression, AAV1, AAV5, AAV6, AAV8 or AAV9 may be used.

DNA plasmids of the invention comprise rAAV genomes. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. Embodiments include, but are not limited to, the rAAV named pAAV.MHCK7.hSCGB which comprises the polynucleotide sequence set forth in SEQ ID NO: 3 or SEQ ID NO: 19; and pAAV.tMCK.hSCGB which comprises the polynucleotide sequence set forth in SEQ ID NO: 5.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.,* 10(6): 1031-1039 (1999); Schenpp and Clark, *Methods Mol. Med.,* 69 427-443 (2002); U.S. Pat. No. 6,566,118 and WO 98/09657.

In another embodiment, the invention contemplates compositions comprising rAAV of the present invention. Compositions described herein comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). The titers of rAAV may be determined by the supercoiled plasmid quantitation standard or the linearized plasmid quantitation standard.

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is muscular dystrophy, such as limb-girdle muscular dystrophy. Thus, provided is a method of transducing a target cell with an rAAV scAAVrh74.MHCK7.hSGCB, which comprises a nucleotide sequence of SEQ ID NO: 3 or 19.

Combination therapies are also contemplated by the invention. Combination as used herein includes both simultaneous treatment or sequential treatments. Combinations of methods of the invention with standard medical treatments (e.g., steroids, corticosteroids, and/or glucocorticoids including but not limited to one or more of prednisone, prednisolone; and deflazacort) are specifically contemplated, as are combinations with novel therapies. In this regard, the combinations include administering to a subject one or more steroids, corticosteroids, and/or glucocorticoids including but not limited to one or more of prednisone, prednisolone; and deflazacort before administering an rAAV of the inventive methods to the subject, simultaneously with administering the rAAV to the subject, or after administering the rAAV to the subject.

In related embodiments of a combination therapy contemplated by the invention, the glucocorticoid includes, but is not limited to beclomethasone, betamethasone, budesonide, cortisone, dexamethasone, hydrocortisone, methylprednisolone, or triamcinolone.

It is recognized that an antigen specific T-cell response may occur in a subject administered with the rAAV vector. This is an expected response between 2-4 weeks following gene transfer. One possible consequence to such antigen specific T-cell responses is clearance of the transduced cells and loss of transgene expression. To dampen the host immune response to the rAAV based therapy, before the therapy, for example, twenty-four hours prior to the therapy procedure, subjects can be started on approximately 1 mg/kg/day prophylactic prednisone or comparable glucocorticoid by mouth with a maximum dose of 60 mg/day. IV administration of a comparable glucocorticoid at the approximate dose of 1 mg/kg/day would also be allowable if needed. Treatment will continue for approximately one month. A tapering protocol for prednisone or comparable glucocorticoid can be implemented based on individual subjects' immune response to the gene transfer, assessed by ELISpot assay and also by liver function monitoring with GGT.

A therapeutically effective amount of the rAAV vector is a dose of rAAV ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg, 6e14 vg/kg, 7e14 vg/kg, 8e14 vg/kg, or 9e14 vg/kg. The invention also comprises compositions comprising these ranges of rAAV vector.

For example, a therapeutically effective amount of rAAV vector is a dose of 1e13 vg/kg, about 2e13 vg/kg, about 3e13 vg/kg, about 4e13 vg/kg, about 5e13 vg/kg, about 6e13 vg/kg, about 7e13 vg/kg, about 7.4e13 vg/kg, about 8e13 vg/kg, about 9e13 vg/kg, about 1e14 vg/kg, about 2e14 vg/kg, about 3e14 vg/kg, about 4e14 vg/kg and 5e14 vg/kg. The titer or dosage of AAV vectors can vary based on the physical forms of plasmid DNA as a quantitation standard. For example, the value of titer or dosage may vary based off of a supercoiled standard qPCR titering method or a linear standard qPCR tittering method. In one embodiment, a therapeutically effective amount of rAAV is a dose of 5e13 vg/kg based on a supercoiled plasmid as the quantitation standard or a dose of 1.85e13 vg/kg based on a linearized plasmid as the quantitation standard. In another embodiment, a therapeutically effective amount of rAAV is a dose of 2e14 vg/kg based on the supercoiled plasmid as the quantitation standard or a dose of 7.41e13 vg/kg based on the linearized plasmid as the quantitation standard. In another embodiment, the therapeutically effective amount of scAAVrh74.MHCK7.hSGCB is a dose ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg, 6e14 vg/kg, 7e14 vg/kg, 8e14 vg/kg, or 9e14 vg/kg, based on the supercoiled plasmid as the quantitation standard. The invention also comprises compositions comprising these doses of rAAV vector.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the β-sarcoglycan.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein.

Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling. Thus, in another aspect, the application is directed to a formulation that comprises an rAAV that comprises an AAVrh74 derived capsid, a buffer agent, an ionic strength agent, and a surfactant. In one embodiment, the rAAV is at a concentration of about $1.0 \times 10^{12}$ vg/ml to about $5.0 \times 10^{14}$ vg/ml. In another embodiment, the rAAV is at a concentration of about $5.0 \times 10^{12}$ vg/ml to about $1.0 \times 10^{14}$ vg/ml based on a supercoiled plasmid as the quantitation standard. In another embodiment, the rAAV is at a concentration of about $2.0 \times 10^{13}$ vg/ml based on a supercoiled plasmid as the quantitation standard. In one embodiment, the rAAV is an scAAVrh74.MHCK7.hSGCB vector. In one embodiment, the concentration of rAAV in the composition or formulation is from $1 \times 10^{13}$ vg/ml to $2 \times 10^{14}$ vg/ml based on a supercoiled plasmid as the quantitation standard. In another embodiment, the concentration is $2 \times 10^{13}$ vg/ml, $4 \times 10^{13}$ vg/ml, or $5 \times 10^{13}$ vg/ml based on a supercoiled plasmid as the quantitation standard. In one embodiment, the buffer agent comprises one or more of tris, tricine, Bis-tricine, HEPES, MOPS, TES, TAPS, PIPES, and CAPS. In another embodiment, the buffer agent comprises tris with pH 8.0 at concentration of about 5 mM to about 40 mM. In one embodiment, the buffer agent comprises tris with pH 8.0 at about 20 mM. In one embodiment, the ionic strength agent comprises one of more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. In one embodiment, the ionic strength agent comprises $MgCl_2$ at a concentration of about 0.2 mM to about 4 mM. In another embodiment, the ionic strength agent comprises NaCl at a concentration of about 50 mM to about 500 mM. In another embodiment, the ionic strength agent comprises $MgCl_2$ at a concentration of about 0.2 mM to about 4 mM and NaCl at a concentration of about 50 mM to about 500 mM. In another embodiment, the ionic strength agent comprises $MgCl_2$ at a concentration of about 1 mM and NaCl at a concentration of about 200 mM. In one embodiment, the surfactant comprises one or more of a sulfonate, a sulfate, a phosphonate, a phosphate, a Poloxamer, and a cationic surfactant. In one embodiment, the Poloxamer comprises one or more of Poloxamer 124, Poloxamer 181, Poloxamer 184, Poloxamer 188, Poloxamer 237, Poloxamer 331, Poloxamer 338, and Poloxamer 407. In one embodiment, the surfactant comprises the Poloxamer at a concentration of about 0.00001% to about 1%. In another embodiment, the surfactant comprises Poloxamer 188 at a concentration of about 0.001%. For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of β-sarcoglycan. The present invention thus provides methods of administering/delivering rAAV which express β-sarcoglycan to a mammalian subject, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., *Science*, 251: 761-766 (1991)], the myocyte-specific enhancer binding factor MEF-2 [Cserjesi and Olson, *Mol Cell Biol* 11: 4854-4862 (1991)], control elements derived from the human skeletal actin gene [Muscat et al., *Mol Cell Biol*, 7: 4089-4099 (1987)], the cardiac actin gene, muscle creatine kinase sequence elements [See Johnson et al., *Mol Cell Biol*, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., *Proc Natl Acad Sci USA*, 88: 5680-5684 (1991)), steroid-inducible elements and promoters including the glucocorticoid response element (GRE) (See Mader and White, *Proc. Natl. Acad. Sci. USA* 90: 5603-5607 (1993)), and other control elements.

Muscle tissue is an attractive target for in vivo DNA delivery, because it is not a vital organ and is easy to access. The invention contemplates sustained expression of miR-NAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of a polynucleotide of interest (e.g., a polynucleotide sequence encoding β-sarcoglycan) to a recipient cell either in vivo or in vitro, via a replication-deficient rAAV described resulting in expression of β-sarcoglycan by the recipient cell.

Thus, also described herein are methods of administering an effective dose (or doses, administered essentially simultaneously or doses given at intervals) of rAAV that encode β-sarcoglycan to a mammalian subject in need thereof.

All publications and patents mentioned herein are hereby incorporated by reference in their entirety as if each individual publication or patent was specifically and individually indicated to be incorporated by reference. In case of conflict, the present application, including any definitions herein, will control.

The invention is further described in the following Examples, which do not limit the scope of the invention described in the claims.

Figure 11:
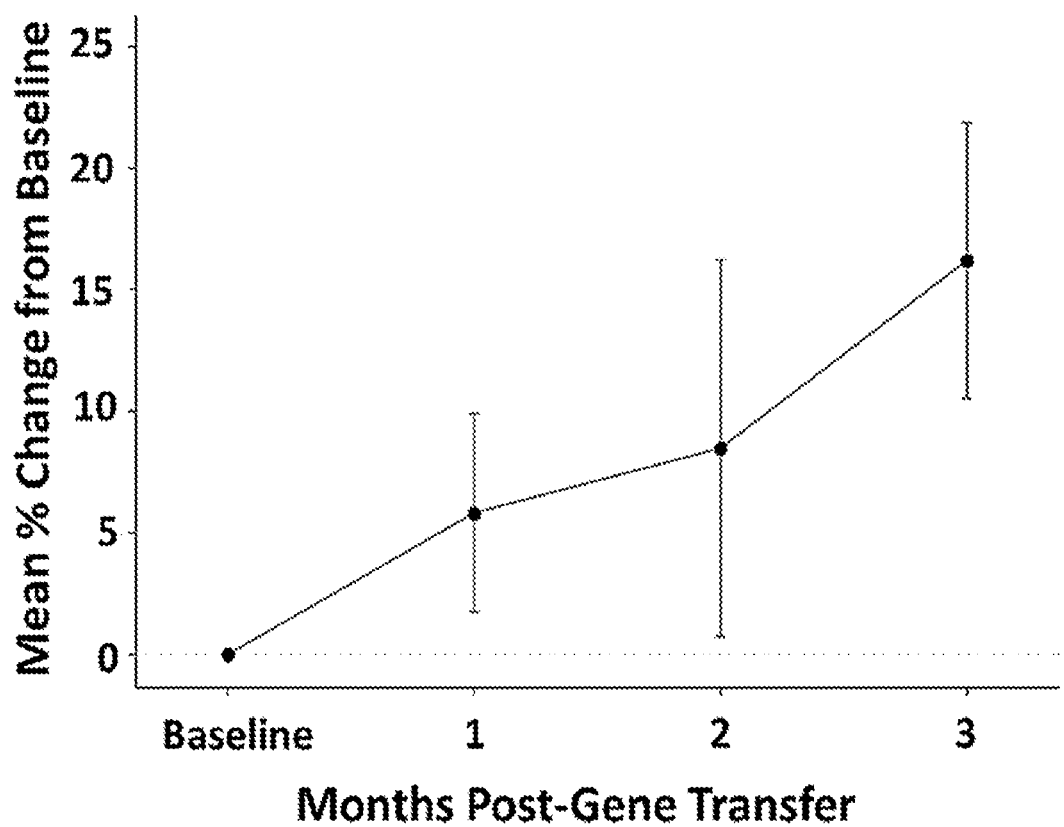
FIG. 11 shows the mean percent change from baseline or improvement on the 100 meter timed test in three subjects over the first three months post-gene transfer with scAAVrh.74.MHCK7.hSGCB.

In another embodiment, the disclosure provides a method of generating the rAAV pAAV.MHCK7.hSCGB, which comprises transferring an AAV vector plasmid to a host cell. The methods of transferring a DNA to a host cell are known in the art, which include but are not limited to transfection, infection, transformation, electroporation, and transduction. In one embodiment, the vector plasmid comprises a nucleotide sequence that is at least 90%, 95%, or 99% identical to SEQ ID NO: 24. In another embodiment, the vector plasmid comprises a nucleotide sequence of SEQ ID NO: 24. In another aspect, the disclosure provides a host cell comprising an AAV vector plasmid that comprises a nucleotide sequence of SEQ ID NO: 24. In some embodiment, the AAV vector plasmid is stably expressed in the host cell. The host cell stably harboring the AAV vector plasmid can be used to generate rAAV. In one embodiment, the AAV vector plasmid is a pAAV.MHCK7.hSGCB. KAN plasmid. The pAAV.MHCK7.hSGCB. KAN plasmid is illustrated in FIG. 11.

In one embodiment, the vector plasmid comprises a nucleotide sequence that is at least 90%, 95%, or 99% identical to SEQ ID NO: 1, 3, 5, or 19. In one embodiment, the vector plasmid comprises a nucleotide sequence of SEQ ID NO: 1, 3, 5, or 19. The method of generating rAAV, in one embodiment, further comprises transferring a packaging plasmid and/or a helper virus to the host cell. The packaging plasmid, in some embodiments, comprises an AAV rep and/or cap gene that is operably linked to a promoter. The promoter, in one embodiment, is an AAV transcription promoter. In one embodiment, the host cell is a packaging cell. In one embodiment, the packaging cell comprises a stably integrated AAV cap gene. In another embodiment, the packaging cell comprises a stably integrated AAV rep gene.

As used herein, the term "host cell" refers to a cell that can be used to express an exogenous DNA sequence. Non-limiting examples of a host cell comprise a microorganism, a yeast cell, an insect cell, and/or a mammalian cell. The host cell can be used as a recipient for an AAV helper construct, a packaging plasmid, an AAV vector plasmid, an accessary function vector, or other DNA. The term as used here encompasses the progeny of the original cell after expressing the exogenous DNA sequence in the original host cell. Non-limiting examples of host cells for AAV production include Sf9 insect cells and HEK 293T cells. In one embodiment, the cell described herein comprises an insect cell, e.g., a *Drosophila* cell (e.g., an S2 cell or Kc cell), a silkworm cell (e.g., a Bme21 cell), or a mosquito cell (e.g., a C6/36 cell); or a mammalian cell (preferably a human cell, e.g., a human primary cell or an established cell line). In one embodiment, the mammalian cell comprises a 293 cell, a COS cell, a HeLa cells, or a KB cell. The AAV vector plasmid can be introduced to the host cells, e.g., Sf9 or 293T, by infection (virus or baculovirus), transient transfection using reagents (e.g., liposomal, calcium phosphate) or physical means (e.g., electroporation), or other means know in the art. In another embodiment, the host cell lines are stably integrated with the rAAV plasmids into their genomes. Such stable cell lines can be established by incorporating a selection marker into the vector plasmid.

In one embodiment, the host cell is a packaging cell for production of AAV viral particles. Thus, in another aspect, the disclosure provides a host cell that comprises an AAV vector plasmid that comprises a nucleotide sequence that is at least 90%, 95%, or 99% identical to SEQ ID NO: 24. In one embodiment, the AAV vector plasmid that comprises a nucleotide sequence of SEQ ID NO: 24. In another embodiment, the host cell comprises a nucleotide sequence of SEQ ID NO: 1, 3, 5, or 19.

EXAMPLES

Preclinical studies using scAAVrh74.MHCK7.hSGCB are described in International Patent Publication No. WO 2017/180976, which is incorporated by reference herein in its entirety.

Example 1

Materials and Methods

Animal models—All procedures were approved by The Research Institute at Nationwide Children's Hospital Institutional Animal Care and Use Committee (protocol AR12-00040). B6.129-Sgcb$^{tm1Kcam/1J}$ heterozygous mice were purchased from the Jackson Laboratory (Bar Harbor, ME, USA; Strain #006832). Sgcb$^{-/-}$ mice were generated by breeding heterozygous mice. KO mice were bred and maintained as homozygous animals in standardized conditions in the Animal Resources Core at the Research Institute at Nationwide Children's Hospital. Mice were maintained on Teklad Global Rodent Diet (3.8z5 fiber, 18.8% protein, 5% fat chow) with a 12:12-h dark:light cycle. Identification of SGCB$^{-/-}$ mice was performed by genotyping using PCR. All animals were housed in standard mouse cages with food and water ad libitum.

Beta-sarcoglycan gene construction. The full-length human beta-sarcoglycan cDNA (GenBank Accession No. NM_0034994.3) was codon optimized and synthesized by GenScript Inc, Piscataway, NJ, USA. Codon optimization through GenScript uses an algorithm that takes into account parameters that include transcription, mRNA processing and stability, translation and protein folding to design a cDNA sequence that results in maximum expression in muscle tissue (genscript.com).

For the pAAV.tMCK.hSGCB construct, the cDNA was then cloned into a plasmid containing AAV2 ITRs and the cassette included a consensus Kozak sequence (CCACC), an SV40 chimeric intron and a synthetic polyadenylation site (53 bp). The recombinant tMCK promoter was a gift from Dr Xiao Xiao (University of North Carolina). It is a modification of the previously described CK6 promoter27 and includes a modification in the enhancer upstream of the promoter region containing transcription factor binding sites. The enhancer is composed of two E-boxes (right and left). The tMCK promoter modification includes a mutation converting the left E-box to a right E-box (2R modification) and a 6-bp insertion (S5 modification). The pAAV.tMCK-.hSGCB vector was constructed by ligation of 1040 bp KpnI/XbaI fragment from pUC57-BSG (Genscript Inc.) into the KpnI/XbaI sites of pAAV.tMCK.hSGCA.26

The pAAV.MHCK7.hSGCB vector was constructed by removing the tMCK promoter and SV40 chimeric intron with NotI/KpnI sites and inserting a PCR amplified fragment containing the MHCK7 promoter and identical SV40 chimeric intron with NotI/KpnI sites. MHCK7 is an MCK based promoter which utilizes a 206-bp enhancer taken from ~1.2 kb 5' of the transcription start site within the endogenous muscle creatine kinase gene with a proximal promoter (enh358MCK, 584-bp)[3,12]. The MHCK7 promoter itself contains this modified CK7 cassette from the MCK family of genes ligated to a 188-bp α-MyHC (α-myosin heavy chain) enhancer 5' of the CK portion to enhance cardiac expression[12]. The creatine kinase portion of the promoter (CK) is 96% identical between tMCK and MHCK7. Finally, the pAAV.MHCK7.hSGCB vector was constructed by ligation of the 960 bp NotI/KpnI MHCK7+Intron fragment from pAAV.MHCK7.DYSF5'DV44 into the NotI/KpnI sites of pAAV.tMCK.hSGCB (Pozgai et al., Gene Ther. 23: 57-66, 2016)

rAAV production. A modified cross-packaging approach, previously reported by Rodino-Klapac et al. (J. Trans. Med. 5:45, 2007), was used to produce the rAAV vector. Here, a triple transfection method with CaPO$_4$ precipitation in HEK293 cells allows for AAV2 ITRs to be packaged into a different AAV capsid serotype. (28,29) The production plasmids were (i) pAAV.tMCK.hSGCB or pAAV.MHCK7.hSGCB, (ii) rep2-caprh.74 modified AAV helper plasmids encoding cap serotype 8-like isolate rh.74 and (iii) an adenovirus type 5 helper plasmid (pAdhelper) expressing adenovirus E2A, E4 ORF6 and VA I/II RNA genes. Vectors were purified and encapsided vg titer (utilizing a Prism 7500 Taqman detector system; PE Applied Biosystems, Carlsbad, CA, USA) was determined as previously described. 30 The primer and fluorescent probe targeted the tMCK promoter and were as follows: tMCK forward primer, 5'-ACC CGA GAT GCC TGG TTA TAA TT-3' (SEQ ID NO: 10); tMCK reverse primer, 5'-TCC ATG GTG TAC AGA GCC TAA GAC-3' (SEQ ID NO: 11); and tMCK probe, 5'-FAM-CTG CTG CCT GAG CCT GAG CGG TTA C-TAMRA-3' (SEQ ID NO: 12). The primer and fluorescent probe targeted the MHCK7 promoter and were as follows: MHCK7 forward primer, 5'-CCA ACA CCT GCT GCC TCT AAA-3' (SEQ ID NO: 16); MHCK7 reverse primer, 5'-GTC CCC CAC AGC CTT GTT C-3' (SEQ ID NO: 17); and MHCK7 probe, 5'-FAM-TGG ATC CCC-Zen-TGC ATG CGA AGA TC-3IABKFQ-3' (SEQ ID NO: 18).

Systemic Gene Delivery: Systemic delivery was achieved through injection of vector into the tail vein of sgcb$^{-/-}$ mice. Mice were injected with $3\times10^{12}$ vg of scAAVrh.74.MHCK7.hSGCB ($2.0\times10^{14}$ vg/kg) diluted in saline using a 30 gauge ultra-fine insulin syringe. Mice were restrained in a holding tube placing the tail back through tail slot to warm it up in order dilate the blood vessels for ease of injection. After locating the artery down the center line of the tail, the injection was performed in one of the purple/blue lateral veins that run alongside the tail artery. All treated mice were injected at 4-5 weeks of age and euthanized 6-months post-injection.

Immunofluorescence. Cryostat sections (12 μm) were incubated with a monoclonal human beta-sarcoglycan primary antibody (Leica Biosystems, New Castle, UK; Cat. No. NCL-L-b-SARC) at a dilution of 1:50 in a block buffer (1×TBS, 10% Goat Serum, 0.1% Tween) for 1 h at room temperature in a wet chamber. Sections were then washed with TBS three times, each for 20 min and re-blocked for 30 min. AlexaFluor 594 conjugated goat anti-mouse secondary IgG1 antibody (Life Technologies, Grand Island, NY, USA; Cat. No. A21125) was applied at a 1:250 dilution for 45 min. Sections were washed in TBS three times for 20 min and mounted with Vectashield mounting medium (Vector Laboratories, Burlingame, CA, USA). Four random ×20 images covering the four different quadrants of the muscle section were taken using a Zeiss AxioCam MRC5 camera. Percentage of fibers positive for beta-sarcoglycan staining (450% of muscle membrane staining intensity) was determined for each image and averaged for each muscle.

Western blot analysis. Tissue sections or muscle biopsies were collected into a micro-centrifuge and homogenized with 100 μl homogenization buffer (125 mM Tris-HCl, 4% SDS, 4 M urea) in the presence of 1 protease inhibitor cocktail tablet (Roche, Indianapolis, IN, USA). After homogenization, the samples were centrifuged at 10,000 rpm for 10 min at 4° C. Protein was quantified on NanoDrop (Thermo Scientific, Waltham, MA, USA). Protein samples (20 μg) were electrophoresed on a 3-8% polyacrylamide Tris-acetate gel (NuPage, Invitrogen, Carlsbad, CA, USA) for 1 h 5 min at 150 V and then transferred onto a PVDF membrane (Amersham Biosciences, Piscataway, NJ, USA) for 1 h 15 min at 35 V. The membrane was blocked in 5% non-fat dry milk in TBST for 1 h, and then incubated with a rabbit polyclonal human beta-sarcoglycan antibody (Novus Biologicals, Littleton, CO, USA; Cat. No. NBP-1-90300 1:100 or 1:250 dilution) and a 1:5000 of a monoclonal mouse gamma-tubulin antibody (Sigma-Aldrich, St Louis, MO, USA; Cat. No. T6557) or a 1:5000 dilution of a mouse monoclonal mouse α-actinin antibody (Sigma-Aldrich, St Louis, MO, USA; Cat. No. A7811). A 1:500 dilution of a rabbit polyclonal mouse cardiac troponin I antibody (Abcam, Cambridge, MA; Cat. No. ab47003) and a 1:1000 dilution of a rabbit monoclonal mouse vinculin antibody (Invitrogen, Frederick, MD; Cat. No. 70062) were used. Anti-mouse (Millipore, Billerica, MA, USA; Cat. No. AP308P) and anti-rabbit (Life Technologies; Cat. No. 656120) secondary-HRP antibodies were used for ECL immunodetection.

Biodistribution qPCR analysis. Taqman quantitative PCR was performed to quantify the number of vector genome copies present in targeted and untargeted contralateral muscle as previously described.(18,30) A vector-specific primer probe set was used to amplify a sequence of the intronic region directly downstream from the tMCK promoter that is unique and located within the scAAVrh.74.tMCK.hSGCB transgene cassette. The following primers and probe were used in this study: tMCK and MHCK7 intron Forward Primer 5'-GTG AGG CAC TGG GCA GGT AA-3' (SEQ ID NO: 13); tMCK and MHCK7 intron Reverse Primer 5'-ACC TGT GGA GAG AAA GGC AAAG-3' (SEQ ID NO: 14); and tMCK and MHCK7 intron Probe 5'-6FAM-ATC AAG GTT ACA AGA CAG-GTT TAA GGA GAC CAA TAG AAA-tamra-3' (IDT) (SEQ ID NO: 15). Copy number is reported as vector genomes per microgram of genomic DNA.

Immunohistochemistry for immune cell staining. Immunohistochemistry was used to identify immune cells. Frozen tissue sections on Fisherbrand Superfrost charged microscope slides were incubated with rat anti-mouse monoclonal antibodies using an anti-rat Ig HRP Detection kit (BD Pharmagen, San Jose, CA, USA; Cat: 551013): CD3 (Cat: 555273), CD4 (Cat: 550280), CD8 (Cat: 550281) and Mac-3 for macrophages (Cat: 550292). All primary antibodies were diluted at 1:20 with phosphate-buffered saline. Positive immune staining was visualized using DAB chromagen diluted in DAB buffer with Streptavidin-HRP peroxidase ectastain ABC Peroxidase. Ten random ×40 images were taken for each muscle and each corresponding stain. The number of mono-nuclear cells was counted and expressed as total number per $mm^2$.

Immunofluorescence: Cryostat sections (12 μm) from the tibialis anterior (TA), gastrocnemius (GAS), quadriceps (QUAD), psoas major (PSOAS), gluteal (GLUT), triceps (TRI), and diaphragm muscles along with the heart were subjected to immunofluorescence staining for the hSGCB transgene via our previously used protocol as described in Pozgai et al., Gene Therap. 23: 57-66, 2016. Sections were incubated with a mouse monoclonal human beta-sarcoglycan primary antibody (Leica Biosystems, New Castle, UK; Cat. No. NCL-L-b-SARC) at a dilution of 1:100. Four random 20× images covering the four different quadrants of the muscle section were taken using a Zeiss AxioCam MRC5 camera. Percentage of fibers positive for beta-sarcoglycan staining (>50% of muscle membrane staining) was determined for each image and averaged for each muscle.

Morphometric Analysis: Hematoxylin and eosin (H&E) staining was performed on 12 μm thick cryosections of muscle from 7 month old C57BL6 WT mice (n=5), $sgcb^{-/-}$ mice (n=5), and rAAV.MHCK7.hSGCB 6 month treated $sgcb^{-/-}$ mice (n=5) for analysis. The percentage of myofibers with central nuclei was determined in the TA, GAS, QUAD, PSOAS, GLUT, TRI, and diaphragm muscles. Additionally, muscle fiber diameters were measured in the GAS, PSOAS, and TRI muscles. Four random 20× images per muscle per animal were taken with a Zeiss AxioCam MRC5 camera. Centrally nucleated fibers were quantified using the NIH ImageJ software and fiber diameters were measured using Zeiss Axiovision LE4 software.

XLaser Monitoring of Open Field Cage Activity: An open-field activity chamber was used to determine overall activity of experimental mice. Mice at 7 months old from the C57BL6 WT (n=6) and untreated $sgcb^{-/-}$ (n=6) control groups along with the rAAV.MHCK7.hSGCB 6 month treated $sgcb^{-/-}$ mice (n=6) were subjected to analysis following a previously described protocol (Kobayashi et al., Nature 456: 511-5, 2008, Beastrom et al., Am. J. Pahol. 179: 2464-74, 2011) with several modifications. All mice were tested at the same time of day in the early morning near then end of the night cycle when mice are most active. All mice were tested in an isolated room, under dim light and with the same handler each time. To reduce anxiety and keep behavioral variables at a minimum, which could potentially affect normal activity of the mice and consequently the results of the assay, the mice tested were not individually housed (Voikar et al., Genes Brain Behav. 4: 240-52, 2005). Mice were activity monitored using the Photobeam Activity System (San Diego Instruments, San Diego, CA). This system uses a grid of invisible infrared light beams that traverse the animal chamber front to back and left to right to monitor the position and movement of the mouse within an X-Y-Z plane. Activity was recorded for 1 hour cycles at 5-minute intervals. Mice were acclimatized to the activity test room for an initial 1 hour session several days prior to beginning data acquisition. Mice were tested in individual chambers in sets of 4. Testing equipment was cleaned between each use to reduce mouse reactionary behavioral variables that could alter our results. Data collected was converted to a Microsoft Excel worksheet and all calculations were done within the Excel program. Individual beam breaks for movement in the X and Y planes were added up for each mouse to represent total ambulation, and beam breaks in the Z plane were added up to obtain vertical activity within the 1 hour time interval.

Example 2 scAAVrh.74.MHCK7.hSGCB Construction

The transgene cassette containing a codon-optimized full-length human SCGB cDNA as shown in FIG. 1 was constructed. The cassette includes a consensus Kozak sequence (CCACC), an SV40 chimeric intron, a synthetic polyadenylation site, and the muscle-specific MHCK7 used to drive expression of the cassette. This is an MCK based promoter which utilizes a 206-bp enhancer taken from ~1.2 kb 5' of the transcription start site within the endogenous muscle creatine kinase gene with a proximal promoter (enh358MCK, 584-bp)[3,12]. The cassette was packaged into a self-complementary (sc) AAVrh.74 vector that is 93% homologous to AAV8. AAVrh.74 has been shown in mice and non-human primates to be safe and effective, particularly in crossing the vascular barrier when delivered to muscle through the circulation.(17, 18, 21)

Example 3

Long-Term Efficacy of High Dose scAAVrh.74.MHCK7.hSGCB Systemic Delivery

Following the strong results of the previous studies with at a dose of $1.0 \times 10^{12}$ vg total dose ($5.0 \times 10^{13}$ vg/kg) scAAVrh.74.MHCK7.hSGCB, vector was delivered through a tail vein injection to 6 $SGCB^{-/-}$ mice at a high dose of $3.0 \times 10^{12}$ vg total dose ($2.0 \times 10^{14}$ vg/kg) to assess transgene expression and efficacy of the vector when delivered systemically at a long-term time point of 24 weeks. Mice were injected at 4-5 weeks of age and a full necropsy on all 6 mice was performed at 24 weeks post-injection. The following muscles were extracted for analysis: TA, gastrocnemius, quadriceps, gluteal, PSOAS major, tricep, diaphragm and heart. Organs were also removed for toxicology and biodistribution studies. In short, hSGCB transgene expression was as high (98.77% across all muscles) following 24 weeks treatment at this high dose compared to our previously studied dose (98.10% across all muscles) and all muscles from treated mice were again almost fully transduced. This was accompanied by improved muscle histopathology and improved function.

β-Sarcoglycan Expression

Figure 2A:
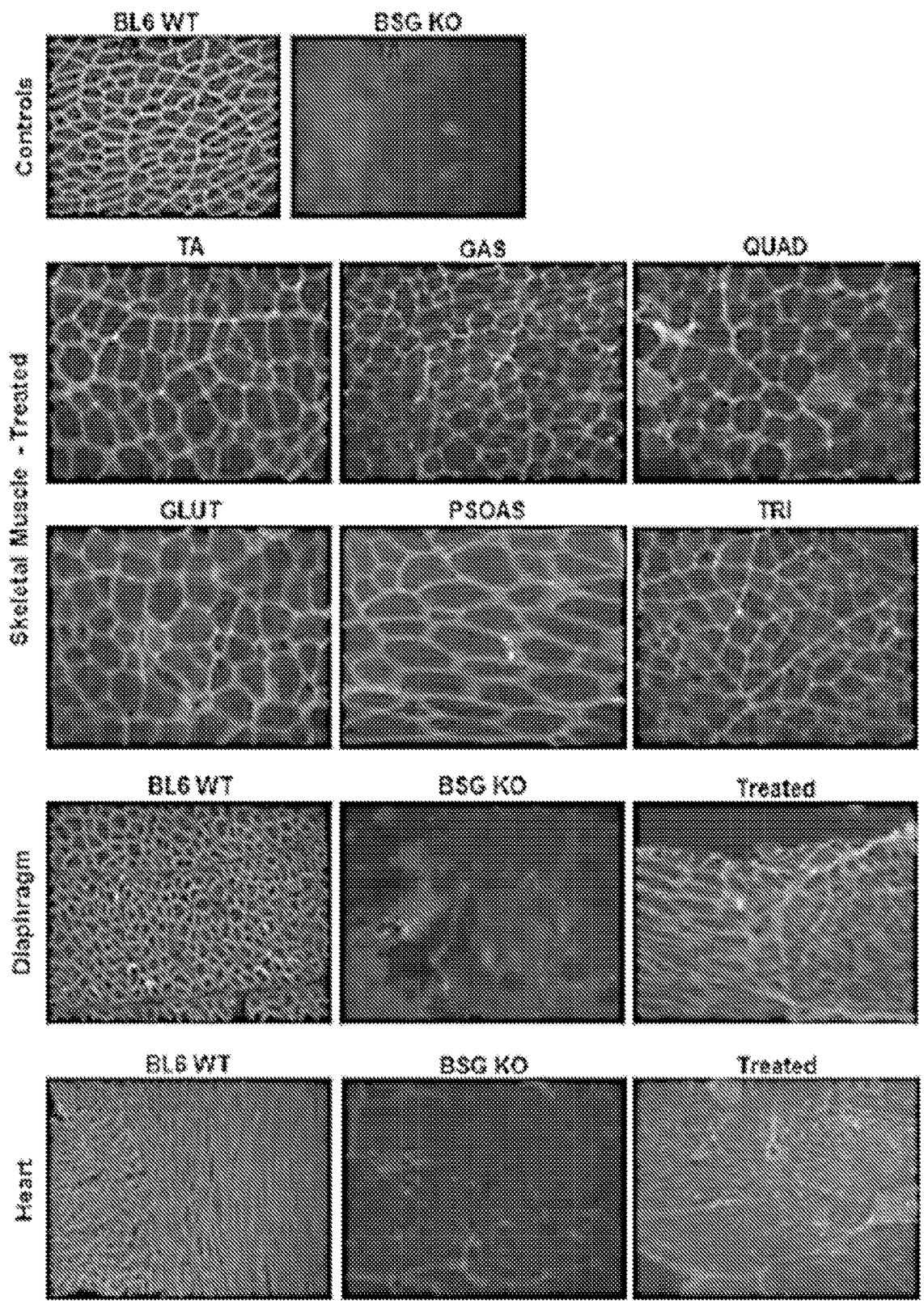
FIG. 2A-2B demonstrates human β-sarcoglycan expression in skeletal muscle, A) Immunofluorescence imaging of skeletal muscles, diaphragm, and heart from SGCB$^{-/-}$ mice intravenously injected with 3e12 vg total dose scAAVrh.74.MHCK7.hSGCB. Representative images with all muscles displaying ≥98% transduction. 20× images are shown. B) Western blotting showing expression of hSGCB transgene (43 kDA) in clinical dose (#716) and high dose (#785, 786) treated muscles. N=6 for treatment group, 100 kDa corresponds to α-Actinin loading control.
Figure 2B:
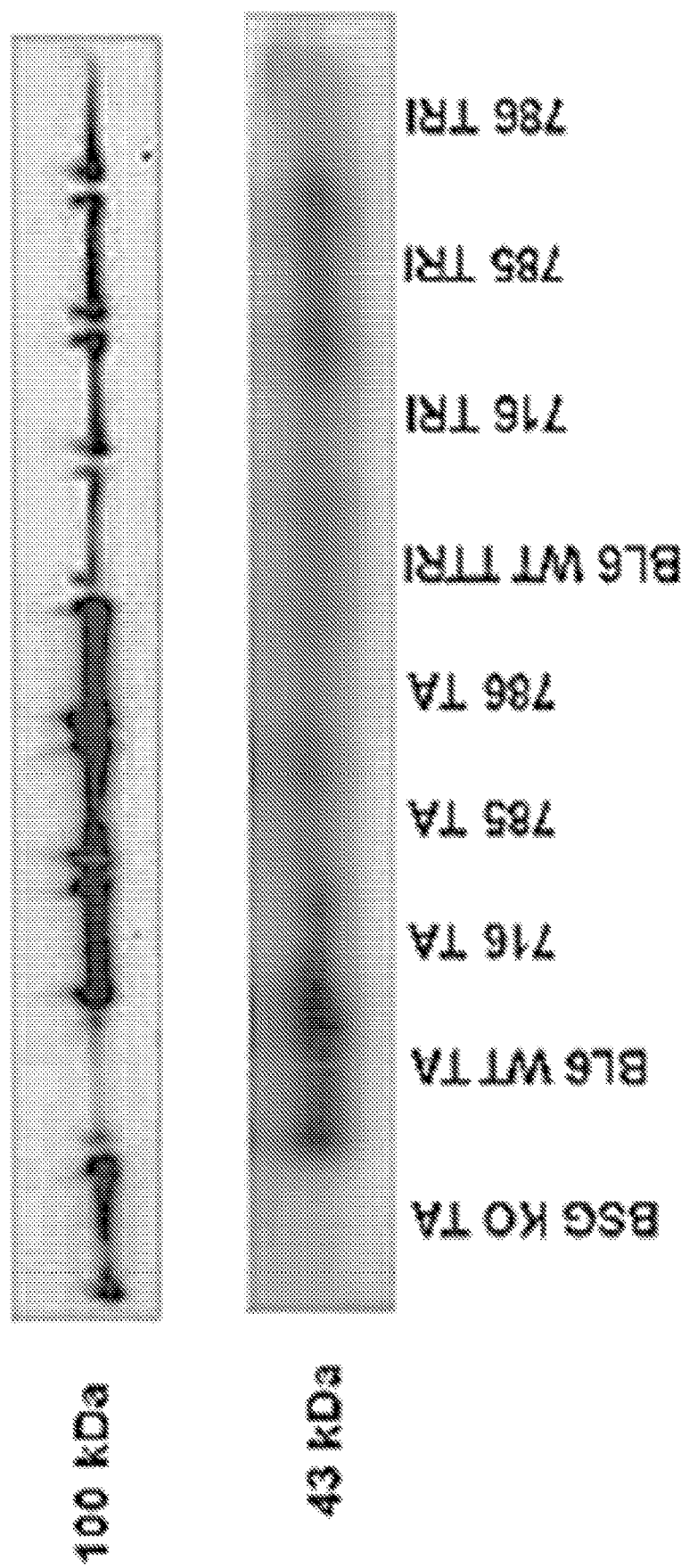

Immunofluorescence (IF) staining for human β-sarcoglycan was used to determine hSGCB transgene expression in six skeletal muscles, in additional to the diaphragm and heart of all the KO mice given a systemic injection of hSGCB vector. These muscles included the TA, gastrocnemius (GAS), quadriceps (QUAD), gluteal (GLUT), psoas major (PSOAS), and triceps (TRI). For the purposes of expression analysis and transduction efficiency, images for the muscles from six treated mice were utilized for quantification. Four 20× images were taken of each muscle and the percent of hSGCB positive fibers was determined for each image resulting in the average percent transduction for each muscle from each mouse, and these data are presented in Appendix C. The results shown in the panel below in FIG. 2A are representative images from the treated mice and demonstrate once again ≥98% transduction in all muscles analyzed including the diaphragm and heart. Finally, the Western blot also depicted in FIG. 2B shows expression of hSGCB in the TA and TRI muscle similar to what was achieved following delivery of the initial clinical dose.

Histopathology of Treated Muscle

Figure 3:
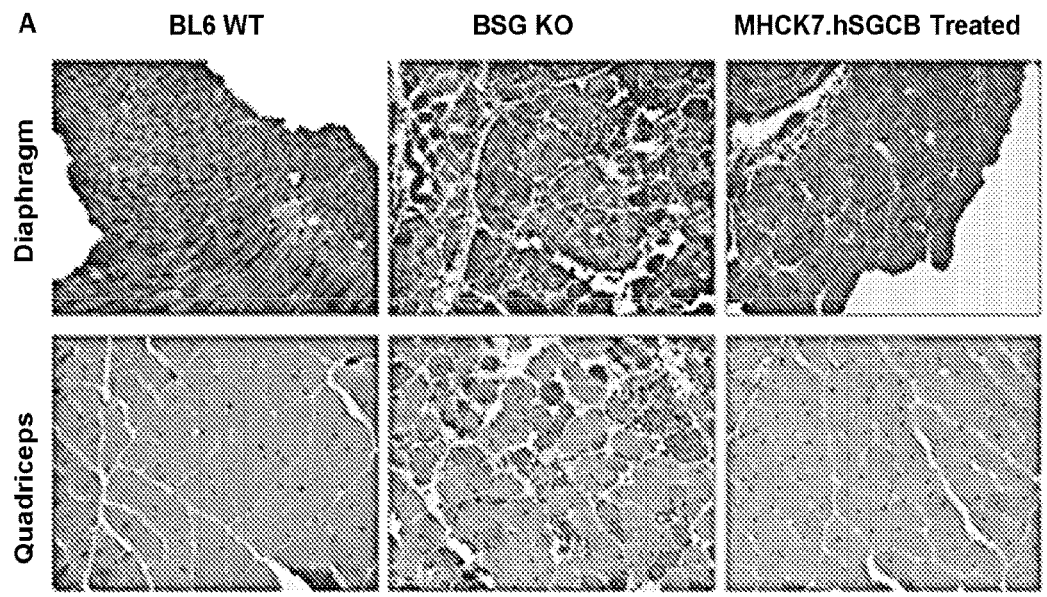
FIG. 3 demonstrates the effect of systemic treatment with high dose scAAVrh74.MHCK7.hSGCB on muscle pathology. (A) H&E stain of quadriceps and diaphragm muscle from C57BL/6 WT, SGCB-/-, and scAAVrh.74.MHCK7.hSGCB treated mice, (B) Quantification of reduction in centrally nucleated fibers, (C) normalization of fiber distribution, and (D) increase in average fiber size. N=6 for each group.*=p<0.05; =p<0.01; *=p<0.001; ****=p<0.0001.
Figure 3:
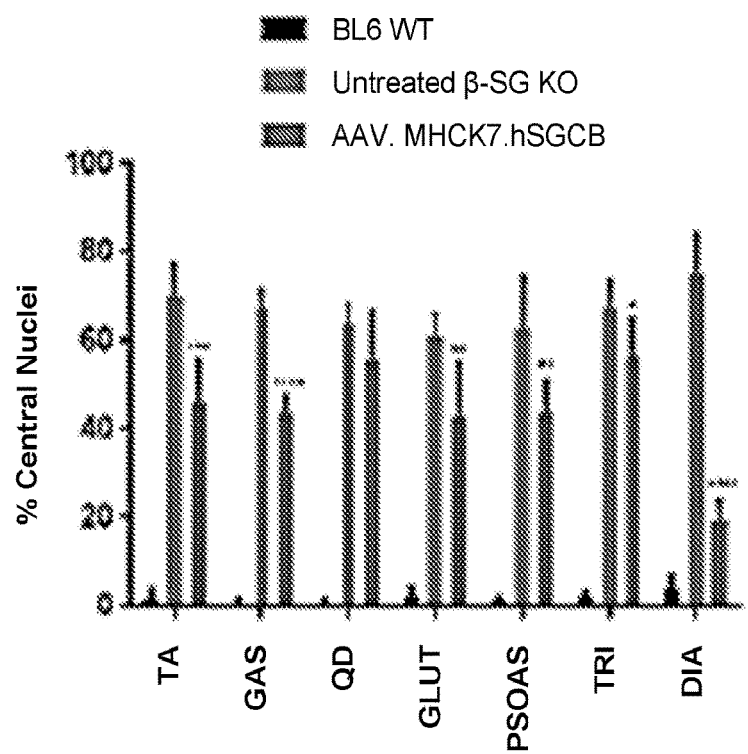
Figure 3:
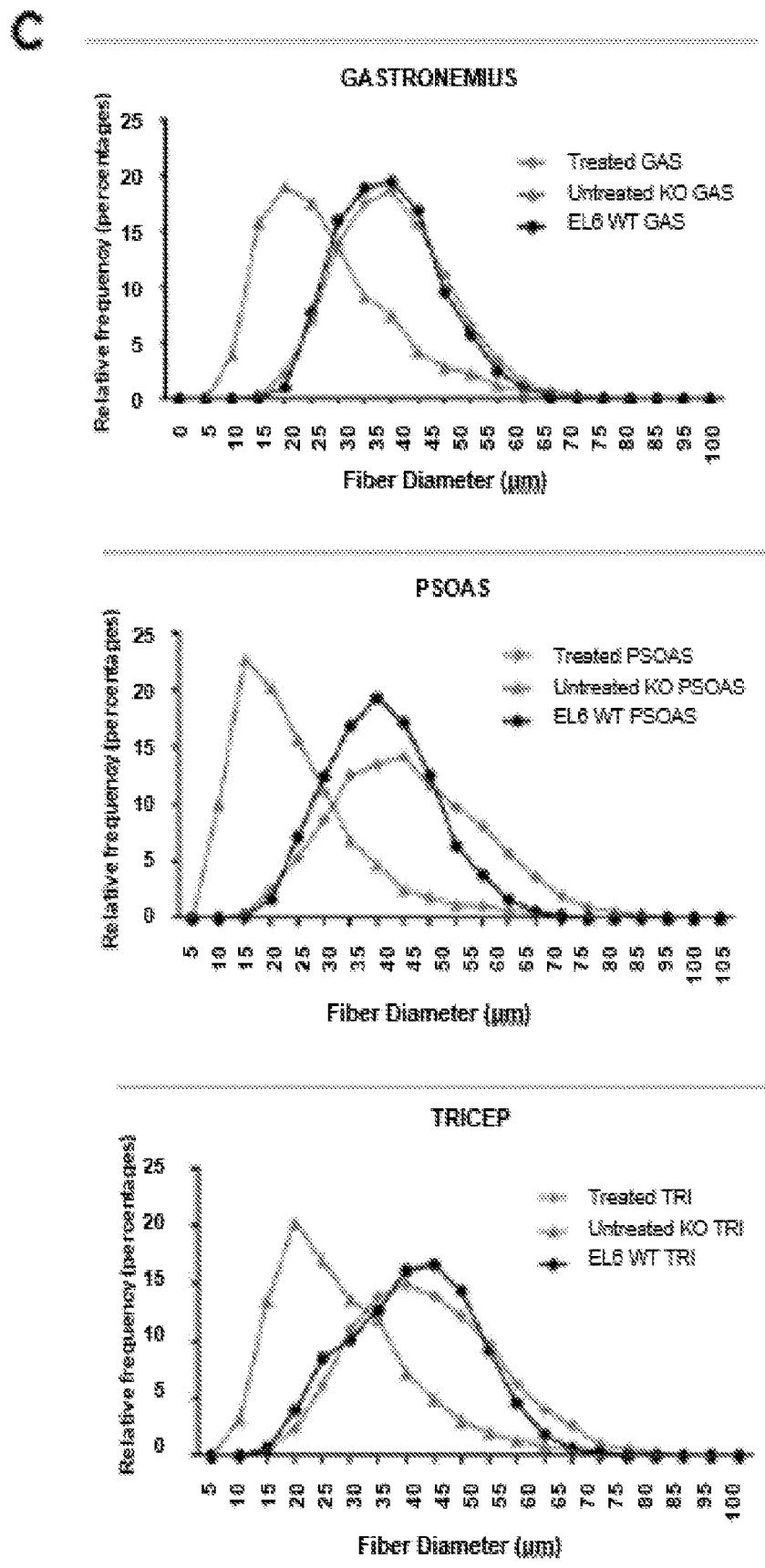
Figure 3:
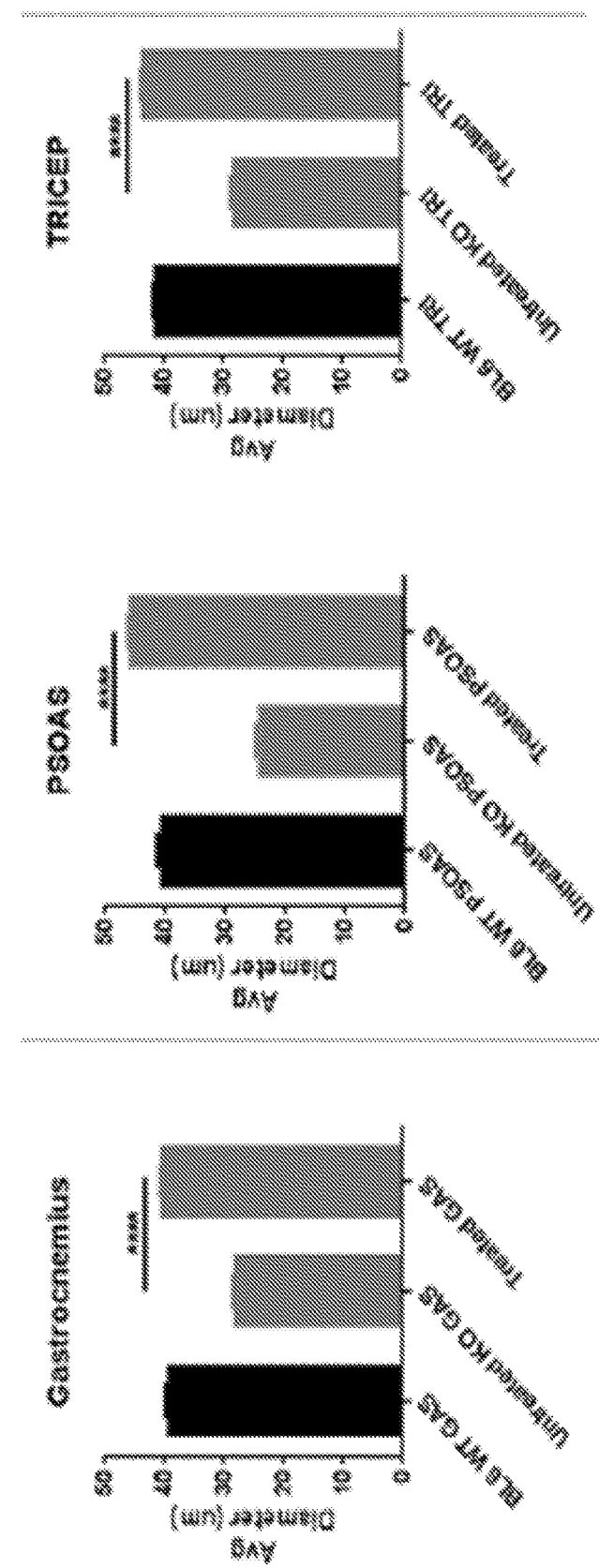

As it was discussed previously, muscles from SGCB$^{-/-}$ mice, both skeletal and cardiac, exhibit widespread myopathy including pronounced myofiber atrophy and hypertrophy with multiple focal areas of necrosis. Also present are increasing numbers of mononuclear cell inflammation (lymphocytes and macrophages, with scattered neutrophils) and increased dystrophic calcification, fatty infiltration, central nucleation, and fibrosis. Hematoxylin & eosin staining in FIG. 3 below illustrates this dystrophic phenotype in SGCB$^{-/-}$ mice when compared to normal wild type mice and the improvement of muscle pathology following treatment. Quantification of histological parameters shows a reduction in central nucleation (CN) in numerous different skeletal muscles as a result of β-sarcoglycan gene transfer. A more in depth analysis of muscle histopathology reveals a normalization of fiber size distribution accompanied by an increase in average fiber diameter in diseased mice treated with vector in all three muscles examined (gastrocnemius, psoas, and tricep) (FIG. 3).

Functional Assessment of Systemic Delivery

Figure 4:
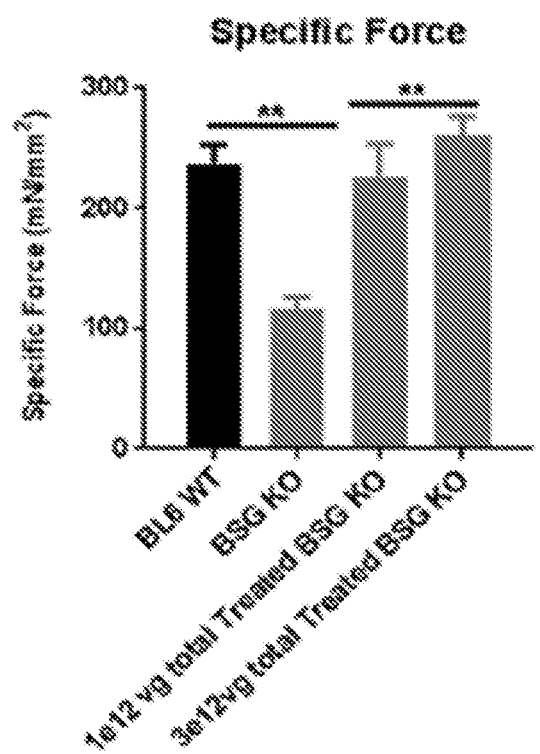
FIG. 4 demonstrates correction of force deficits in the diaphragm of SGCB$^{-/-}$ mice. Following 24 weeks of treatment diaphragm muscle strips were harvested from mice to measure force production following stimulus. Treatment restored force to WT levels and provided a greater restoration compared to the previously studied dose (1e12 vg total dose) (WT: n=5; KO: n=4; Low Dose: n=6; High Dose: n=6).**=p<0.01.

To determine whether high dose hSGCB gene transfer provides an even greater functional benefit to diseased muscle, the functional properties of the diaphragm muscle from SGCB$^{-/-}$ mice treated with high dose scAAVrh.74.MHCK7.hSCGB. Histopathology was demonstrated and established a functional deficit in diaphragms and hearts of SGCB$^{-/-}$-mice. β-sarcoglycan KO diaphragms demonstrated a 50.9% reduction in specific force output compared to BL6 WT mice (116.24 mN/mm$^2$ vs. 236.67 mN/mm$^2$). Tail vein delivery of high dose scAAVrh.74.MHCK7.hSGCB resulting in nearly 100% hSGCB expression in the diaphragm lead to restoration of diaphragm specific force output which improved to 259.97 mN/mm$^2$ (n=6) (FIG. 4). These data show that high dose hSGCB gene transfer does provide a greater functional benefit to diseased muscle deficient for β-sarcoglycan.

Figure 5:
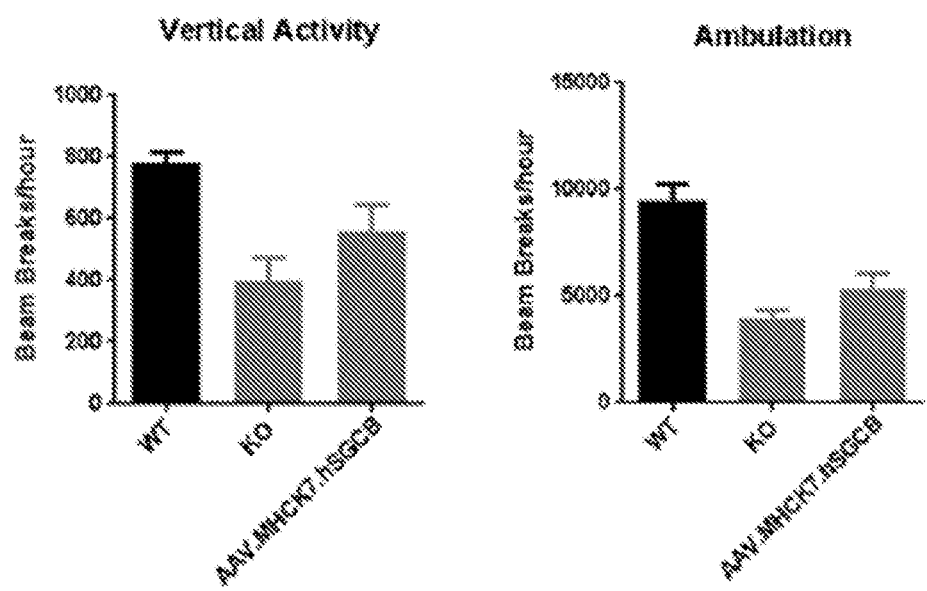
FIG. 5 demonstrates overall ambulation in x and y planes is significantly decreased in KO mice and slightly improved in MHCK7 treated mice. Vertical activity rearing onto hindlimbs was slightly improved in MCHK7 treated mice (n=6).

In order to determine if high dose AAV.hSGCB therapy provides an overall functional benefit to diseased SGCB$^{-/-}$ mice as occurred with delivery of our clinical dose and ultimately improves the phenotype of SGCB$^{-/-}$ mice, laser-monitoring of open-field cage activity was performed on all groups of mice. The graphs in FIG. 5 below depict a significant decrease by 58.6% in total ambulation in x and y planes along with a 48.9% decrease in hindlimb vertical rearing in KO mice compared to WT. High dose scAAVrh.74.MHCK7.hSGCB treated mice were overall more active compared to KO by qualitative observation and that is illustrated in the quantification of activity where total ambulation increased by 36.2% and hindlimb vertical rearing increased by 39.0% in MCHK7 treated mice (n=6 per group) (FIG. 5).

Intravenous injection of scAAVrh.74.MHCK7.hSGCB at a higher dose of 3.0×10$^{12}$ vg total dose (2.0×10$^{14}$ vg/kg) lead to nearly complete transduction and restoration of hSGCB expression in limb skeletal muscles, diaphragm, and importantly cardiac muscle (≥98%) (FIG. 2). The fact that high levels of transduction was achieved in all muscles throughout the body using relatively low doses (5.0×10$^{13}$ vg/kg and 2.0×10$^{14}$ vg/kg) due to the self-complementary AAV vector and rh.74 serotype gives this therapy great promise for translation to LGMD2E patients. The severe dystrophic pathology seen in all muscles in the absence of β-sarcoglycan was significantly improved following treatment (FIG. 3). These results led to the observed increase in specific force output in the diaphragm and increased open-field cage activity (FIGS. 4, 5).

Example 4

Toxicology & Vector Biodistribution

The purpose of this study was to assess any potential toxicity or safety concerns of SGCB gene therapy in male and female SGCB$^{-/-}$ mice at 24 weeks after delivery of the test article scAAVrh.74.MHCK7.hSGCB. Test article was given at 3.0×1012 vg total dose (2.0×10$^{14}$ vg/kg) by the intravenous (IV) route to 4-5 week old SGCB$^{-/-}$ mice in a total volume 520 µL split into two injections of 260 µL each 5 hours apart to achieve the desired dose. To assess the safety of our vector, hematoxylin & eosin staining was performed on cryosections of muscle tissue and all offsite organs harvested from a group of six SGCB$^{-/-}$ mice treated with vector along with two WT and two KO controls injected with LRS (Table 1).

TABLE 1 scAAVrh.74.MHCK7.hSGCB Safety Study Design

| Group | Genotype | Vector Titer (vg Total Dose) | Mouse No. | Sex | Age at Injection | Age at Necropsy |
|---|---|---|---|---|---|---|
| 1 | SGCB-/- | 3.0 × 10$^{12}$ | 785 | Male | 4 weeks | 28 weeks |
| | | | 786 | Female | 4 weeks | 28 weeks |
| | | | 787 | Female | 4 weeks | 28 weeks |
| | | | 788 | Male | 4 weeks | 28 weeks |
| | | | 789 | Male | 4 weeks | 28 weeks |
| | | | 790 | Male | 4 weeks | 28 weeks |

TABLE 1-continued scAAVrh.74.MHCK7.hSGCB Safety Study Design

| Group | Genotype | Vector Titer (vg Total Dose) | Mouse No. | Sex | Age at Injection | Age at Necropsy |
|---|---|---|---|---|---|---|
| 2 | SGCB-/- | None | 1 | Male | N/A | 28 weeks |
|   |   |   | 2 | Male | N/A | 28 weeks |
| 3 | Wild-type | None | 1 | Male | N/A | 28 weeks |
|   |   |   | 2 | Male | N/A | 28 weeks |

These sections were then formally reviewed for toxicity by a veterinary pathologist and no adverse effects were detected in most samples from any of the mice with the exception of a few focal areas of hepatitic lesions in the livers of two treated mice (#789 and 790). Protein expression and vector biodistribution were also assessed using qPCR and Western blotting, and these data indicate no hSGCB transgene expression in any non-muscle tissue except for the livers of mice #785 and #787.

Histopathology Review of Vector Transduced Tissue

In order to determine the safety and toxicology profile of $2.0\times10^{14}$ vg/kg scAAVrh.74.MHCK7.hSGCB using systemic delivery, a variety of skeletal muscles including the diaphragm, along with the heart and five other organs were harvested from a group of vector dosed SGCB$^{-/-}$ mice and controls and H&E sections of each tissue were formally reviewed by an independent veterinary pathologist. Group details and study design are shown in Table 1.

Dosing cohorts for scAAVrh.74.MHCK7.hSGCB histopathology studies. Two BL6 WT mice and two SGCB$^{-/-}$ mice were injected with LRS to serve as appropriate age-matched controls. Six SGCB$^{-/-}$ were given $3.0\times1012$ vg total dose by IV. Mice were euthanized 24 weeks post-injection at and endpoint age of 28 weeks.

In summary, IV injection of high dose scAAVrh.74.MHCK7.hSGCB did not elicit any microscopic changes in myofibers of any skeletal muscles examined. Any changes noted in muscle were seen in both treated and control mice and were considered incidental findings. In addition, no treatment-related lesions were seen in most of the non-muscle tissues evaluated histologically, with only the livers of mice #789 and #790 showing small focal hepatic lesions.

To further evaluate clinical liver function, the levels of liver enzymes in the serum of these mica was assessed. Two untreated BL6 WT mice and two untreated SGCB$^{-/-}$ mice along with six scAAVrh.74.MHCK7.hSGCB treated mice for analysis of Alanine Aminotransferase (ALT) and Aspartate Aminotransferase (AST) levels to determine if they are elevated compared to normal levels. Table 2 below indicates untreated SGCB$^{-/-}$ mice present with elevated ALT and AST levels at an average of 288 U/L and 784.5 U/L respectively, outside of the normal range in healthy mice. AAV dosed SGCB-/- mice however present with average ALT and AST levels that are not elevated and in the normal range at 89.5 U/L and 330.75 U/L for ALT and AST respectively.

Taken together, these data indicate that this test article was well tolerated by the test subjects. Furthermore, relative to reference specimens from two age-matched, untreated SGCB$^{-/-}$ mice, independent histopathology review indicated administration of scAAVrh.74.MHCK7.hSGCB substantially decreased myofiber atrophy and destruction in treated SGCB$^{-/-}$ mice, thus showing that the test article can ameliorate the degree of myopathy associated with profound deficiencies of SGCB.

TABLE 2

Liver Enzyme Level Analysis in Serum From SGCB$^{-/-}$ Mice Treated Systemically With scAAVrh.74.MHCK7.hSGCB

| Mouse Number | Strain | AAV Treated | ALT (U/L) | AST (U/L) | Average ALT (U/L) | Average AST (U/L) |
|---|---|---|---|---|---|---|
| 785 | BSG KO | Y | 71 | 291 | 89.5 | 330.75 |
| 786 | BSG KO | Y | N/A | N/A | | |
| 787 | BSG KO | Y | N/A | N/A | | |
| 788 | BSG KO | Y | 55 | 267 | | |
| 789 | BSG KO | Y | 182 | 563 | | |
| 790 | BSG KO | Y | 50 | 202 | | |
| BL6 WT-1 | BSG KO | N | N/A | N/A | 69 | 132 |
| BL6 WT-2 | BSG KO | N | 69 | 132 | | |
| BSG KO-1 | BSG KO | N | 480 | 862 | 288 | 784.5 |
| BSG KO-2 | BSG KO | N | 96 | 707 | | |

Normal ALT Range: 27-195 U/L

Normal AST Range: 43-397 U/L

Table 2 provides analysis of Alanine Aminotransferase and Aspartate Aminotransferase levels in the serum of untreated BL6 WT (n=2) and SGCB$^{-/-}$ (n=2) along with scAAVrh.74.MHCK7.hSGCB treated SGCB$^{-/-}$ mice (n=6). Averages reported in far right two columns are for each of the three cohorts. Reported in Units/L. N/A indicates samples were hemolyzed and unable to be analyzed.

Vector Genome Biodistribution

The presence of test article-specific DNA sequences was examined using a real time, quantitative PCR assay (qPCR). Biodistribution analysis was performed on tissue samples collected from four vector dosed SGCB$^{-/-}$ animals. A positive signal is anything equal to or greater than 100 single-stranded DNA copies/μg genomic DNA detected. Tissues were harvested at necropsy and vector specific primer probe sets specific for sequences of the MHCK7 promoter were utilized. Table 3 depicts the vector genome copies detected in each tissue sample from high dose ($3.0\times10^{12}$ vg total dose) scAAVrh.74.MHCK7.hSGCB injected mice (#785, 786, 789, 790) along with the vg copy numbers from the same tissue samples in our previously studied clinical dose ($1.0\times10^{12}$ vg total dose) treated mice (#712, 713).

scAAVrh.74.MHCK7.hSGCB transcript was detected at varying levels in all collected tissues. As expected, the highest levels were seen in skeletal muscle and the heart. The lowest levels were detected in gonad, lung, kidney, and spleen. Of note, the vector genome copy numbers were similar in each tissue when comparing the original clinical dose ($5.0\times10^{13}$ vg/kg) with this high dose ($2.0\times10^{14}$ vg/kg) cohort. These data indicate that the test article was efficiently delivered into all investigated tissues of vector dosed mice.

TABLE 3

Quantitative PCR Results Following High Dose
scAAVrh.74.MHCK7.hSGCB Systemic Delivery in SGCB-/- Mice Vector genome copies/µg

| | $1.0 \times 10^{12}$ vg dose | | $3.0 \times 10^{12}$ vg dose | | | |
|---|---|---|---|---|---|---|
| Tissue | #712 | #713 | #785 | #786 | #789 | #790 |
| Gonad | 1.54e+004 | 2.31e+004 | 7.27E+04 | 2.43E+06 | 2.32E+05 | 2.02E+05 |
| Heart | 9.81e+005 | 1.23e+006 | 2.07E+06 | 3.59E+06 | 2.04E+06 | 4.60E+06 |
| Lung | 2.34e+005 | 3.21e+005 | 4.54E+05 | 9.19E+05 | 2.55E+06 | 1.08E+06 |
| Kidney | 1.30e+005 | 9.16e+004 | 5.46E+05 | 1.48E+06 | 2.63E+06 | 5.91E+06 |
| Liver | 3.51e+007 | 4.07e+007 | 7.31E+07 | 3.46E+07 | 4.75E+05 | 1.84E+06 |
| Spleen | 3.30e+005 | 1.84e+005 | 5.39E+05 | 9.72E+05 | 9.87E+05 | 1.02E+06 |
| Diaphragm | 9.82e+005 | 1.29e+006 | 3.85E+06 | 4.11E+05 | 5.50E+06 | 2.57E+06 |
| TRI | 1.82e+006 | 1.29e+006 | 1.77E+06 | 2.21E+06 | 5.41E+06 | 2.52E+06 |
| QD | 9.20e+005 | 1.14e+006 | 1.47E+06 | 3.45E+06 | 3.79E+06 | 3.65E+06 |
| GAS | 1.37e+006 | 8.04e+005 | 2.06E+06 | 1.35E+06 | 7.09E+06 | 2.35E+06 |
| TA | 1.80e+006 | 1.11e+006 | 2.02E+06 | 1.15E+06 | 2.23E+06 | 2.51E+06 |

Figure 6:
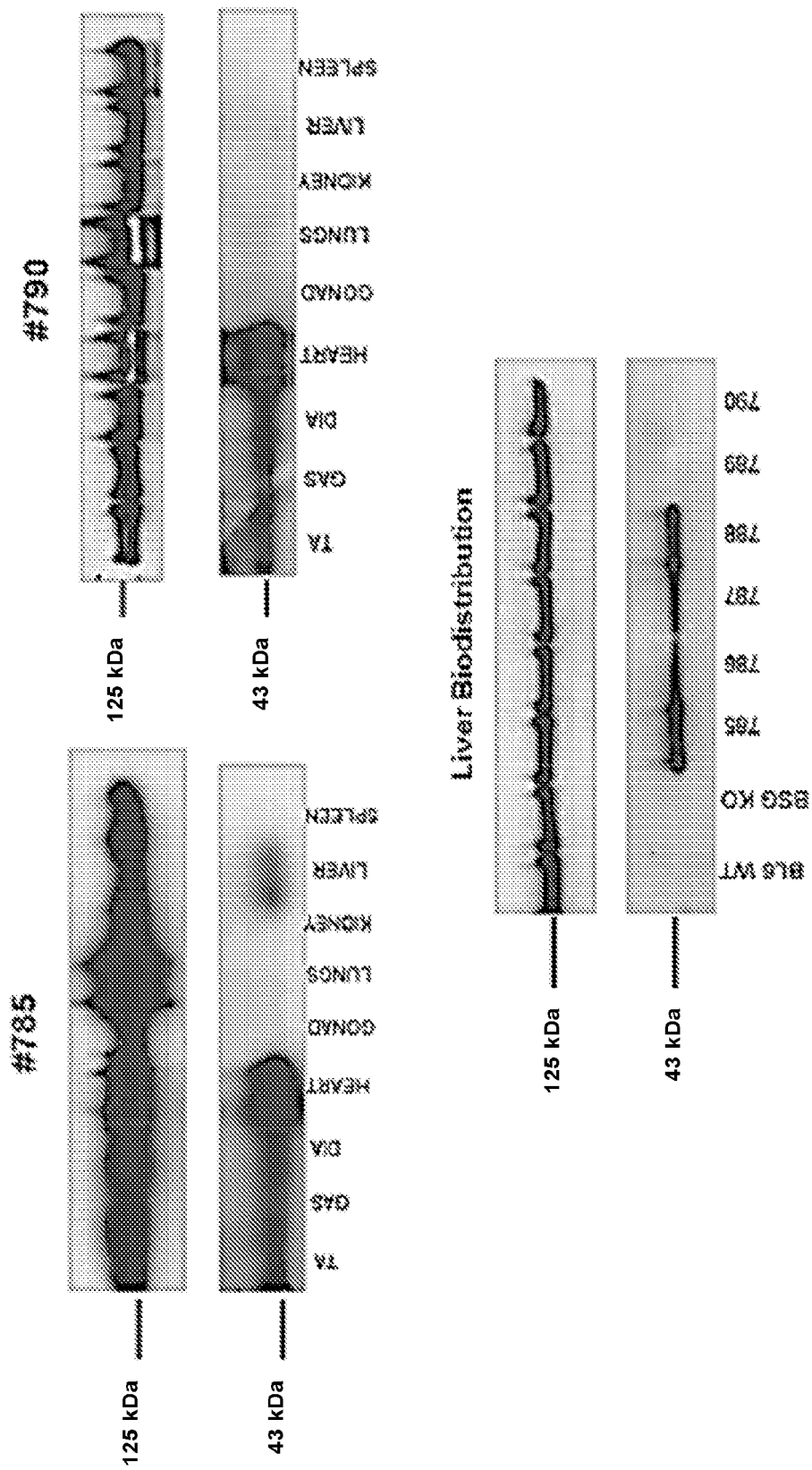
FIG. 6 provides biodistribution westerns on muscles and organs from two high dose ($2.0 \times 10^{14}$ vg/kg) scAAVrh.74.MHCK7.hSGCB systemically injected SGCB$^{-/-}$ mice. 43 kDa corresponds to β-sarcoglycan protein. 125 kDa corresponds to Vinculin loading control.

Table 3 provides vector genome copy numbers organs and muscles from four high dose treated SGCB$^{-/-}$ mice. Values are shown in vg/µg genomic DNA As the qPCR results above indicate, intravenous delivery of high dose scAAVrh.74.MHCK7.hSGCB results in distribution of vector transcript to varying levels in most tissues, however with the highest levels occurring in muscle. Therefore, the objective of this portion of the study was to determine the protein expression of the human β-sarcoglycan transgene in these tissues to ensure the functionality of the muscle specific MHCK7 promoter. Western blotting was used to detect β-sarcoglycan expression in the tissue samples from four of the treated mice (#785, 787, 789, and 790).

β-sarcoglycan protein expression was observed in varying amounts in all skeletal muscle samples as well as heart samples, and was detected in the livers of mice #785, and 787. (Table 4, FIG. 6). To investigate the expression in liver further, Western blotting for β-sarcoglycan protein expression was performed on liver tissue from all six treated mice (#785, 786, 787, 788, 789, and 790). The results of this Western shown in FIG. 6 indicate we do see β-Sarcoglycan protein expression in four of the six livers from vector dosed mice (#785, 786, 787, and 788). Below in Table 5 lists the detailed p-sarcoglycan protein expression results from all six mice in which full biodistribution westerns were performed (#785, 796, 787, 788, 789, and 790).

TABLE 4

β-Sarcoglycan Protein Biodistribution Following High Dose
scAAVrh.74.MHCK7.hSGCB Systemic Delivery in SGCB-/- Mice

| | Mouse # | | | | | |
|---|---|---|---|---|---|---|
| Tissue | 785 | 786 | 787 | 788 | 789 | 790 |
| TA | X | N/A | X | N/A | X | X |
| GAS | X | N/A | X | N/A | X | X |
| DIA | X | N/A | X | N/A | X | X |
| HEART | X | N/A | X | N/A | X | X |
| GONADS | | N/A | | N/A | | |
| LUNGS | | N/A | | N/A | | |
| KIDNEY | | N/A | | N/A | | |
| LIVER | X | X | X | X | | |
| SPLEEN | | N/A | | N/A | | |

Table 4 provides β-Sarcoglycan protein expression in individual tissues from six SGCB-/- mice treated systemically with $2.0 \times 10^{14}$ vg/kg scAAVrh.74.MHCK7.hSGCB. An X indicates protein expression in the corresponding tissue. NA=assay not performed This cardiac expression using the MHCK7 promoter is very encouraging at dosing levels that could be applied clinically, and given the high incidence of heart involvement in the β-sarcoglycan deficiency in the LGMD2E patients, systemic delivery would be most beneficial to these patients clinically. SGCB$^{-/-}$ mice given an intravenous tail vein injection of scAAVrh.74.MHCK7.hSGCB at this proposed high dose of $3.0 \times 10^{12}$ vg total dose ($2.0 \times 10^{14}$ vg/kg) were fully necropsied and all muscles and organs extracted were stained by H&E and sent to an independent veterinary pathologist for review. The livers from four vector dosed mice (#785, 786, 787, and 788) did show expression of the β-Sarcoglycan transgenic protein which has been demonstrated previously with systemic dosing (Salva et al., Mol Ther, 2007. 15(2): p. 320-9). Two of six treated animals (#789 and 790) were reported to have minimal to mild focal hepatic lesions however all other organs and muscles reviewed from the six treated mice showed no adverse effects. To evaluate any clinical manifestations of the mild hepatic lesions in the livers from mice #789 and #790, we measured liver enzyme levels, Alanine Aminotransferase and Aspartate Aminotransferase, in the serum from all six treated mice. The results of this experiment shown in Table 4 depict the average AST and ALT levels from the six treated mice are within the normal range, indicating no clinical liver enzyme abnormalities. The livers from animals #789 and #790 presented with a lower vg copy number (Table 3) in addition to absent β-Sarcoglycan transgenic protein expression. Taken together, this data indicates that the transgenic β-Sarcoglycan protein may have been cleared from the liver in these two animals; however there was no impact on skeletal muscle expression or liver function.

At the high dose ($2.0 \times 10^{14}$ vg/kg), there does appear to be persistent p-Sarcoglycan expression in liver which was not observed in lower dose treated animals ($5.0 \times 10^{13}$ vg/kg). There has been no overt toxicity observed at any doses provided. The trial will be initiated at a NOAEL dose ($5.0 \times 10^{13}$ vg/kg). Liver toxicity in patients was closely monitored, and liver enzyme elevations have been effectively managed using corticosteroids in another systemic delivery trial for spinal muscular atrophy using AAV (Mendell et al., N Engl J Med 2017; 377:1713-1722).

Example 5

LGMD2E Open-Label Trial

Recombinant AAVrh74 carrying the human SGCB gene under control of the muscle-specific MHCK7 promoter (scAAVrh74.MHCK7.hSGCB) was delivered one-time via a systemic infusion through a peripheral vein. The vector is delivered in approximately 10 ml/kg Lactated Ringer's, if needed, to be infused over approximately 1-2 hours. Patient were Glucocorticosteroid adrenal suppression is at most very minimal after 30 days but in the interest of caution, the maximum dose for each enrollee will reduced by 50% for 1 week, and again by 50% for 1 week before stopping.

Cohort 1 included 3 treated subjects 4-15 years of age which had confirmed SGCB mutation in both allele, were negative for AAVrh74 antibodies and >40% of normal 100 meter walk test. Each of the subjects received a dose of $5 \times 10^{13}$ vg/kg. Sixty days after dosing, needle muscle biopsies were done on the tibialis anterior and biceps muscles with appropriate anesthesia under advisement of anesthesiologist (or anesthetist). The biopsies may be done under ultrasound guidance. Each subject received 1 mg/kg prednisone 1 day prior to gene transfer, taped the dose for 30 days.

Biopsies were read and if ≥50% of muscle fibers express SGCB in TA and biceps of all Cohort 1 subjects, there will be no dose escalation in Cohort 2. If these criteria are not met, the subjects in Cohort 2 will receive $2 \times 10^{14}$ vg/kg. Three of the patients in Cohort 2 will receive placebo Lactated Ringers'. These placebo subjects will be treated with the same dose as the treated subjects in their cohort approximately one year later.

Baseline Measurements Prior to Injection (Day −60 to Day −2)

After obtaining informed consent and completing the registration procedures, a baseline patient history was collected, including records of all medications and supplements that the patient is taking. Baseline functional testing to establish a stable baseline were compared to functional testing results gathered in a previous natural history study for consistency of the baseline testing. At the screening visit, the 100 m timed test must be ≥40% of predicted for age, height and weight matched healthy controls for inclusion. If a subject does not screen-in, he or she may continue to participate in an LGMD natural history study. The following assessments will be performed to confirm subject eligibility for this study. Baseline tests which must be completed prior to treatment administration include the following:

| Baseline |
| --- |
| Day −60 to day −2 before gene transfer |
|   Informed Consent |
|   Medical History |
|   Physical exam/ vitals |
|   EKG |
|   Cardiac MRI (will be done without anesthesia but if the procedure is poorly tolerated and considering the importance of cardiac evaluations in this disease, we will discuss options with anesthesia using an acceptable protocol at Nationwide Children's protocol) |
|   Skeletal muscle MRI without anesthesia |
|   Antibody (IgG and IgM) testing for Hepatitis B, and C, and for HIV |
|   Safety Labs: |
|     Complete blood count (CBC) with differential and platelets |
|     Serum total protein |
|     Serum gamma-glutamyl transferase (GGT) |
|       GGT will be used to monitor liver enzymes rather than ALT or AST because of the source of these enzymes from damaged muscle, where levels can reach 9-10× ULN. ALT and AST can vary by 30-40% from day to day making interpretation difficult. GGT is not affected by muscle disease [22,23] |
|     Serum total bilirubin |
|     Glucose |
|     Creatine kinase (CK) (CK levels will only be drawn preferably on 2 day visits but may be tested on a one day visit per PI discretion) |
|     Creatinine/BUN |
|     Cystatin C |
|     Alkaline phosphatase |
|     Amylase |
|     AST |
|     ALT |
|     Prothrombin time (PT), partial thromboplastin time (PTT) |
|     Electrolytes (sodium, potassium, chloride, C02) |
|     Urinalysis |
|   Serum binding antibody to rAAVrh74 |
|   Serum binding antibody to β-sarcoglycan |
|   ELISpot assay to AAVrh74 capsid proteins and β-sarcoglycan |
|   Pregnancy test (if judged by the investigator to be of childbearing potential) |
|   Strength testing (handheld dynamometry) of knee and elbow flexors and extensors, hip adductors, and shoulder abductors |
|   PROMIS questionnaires |
|   Set up with equipment for activity monitoring |
|   Pulmonary function testing (PFTs), including spirometry |
|   Timed Functional Testing [100 meter timed test, Ascending 4 stairs, Timed Up and Go] |
|   Workspace volume |
|   North Star Assessment for Limb Girdle Muscular Dystrophies (NSAD) |
|   Baseline muscle biopsy, may use guided ultrasound, of upper and lower limb muscle; choice depending on clinical findings targeting a muscle that will be adequate for analysis with the least risk to the patient. Placebo delayed subjects will not have a second baseline muscle biopsy performed. |
|   Chest X-ray |
| Day −1 |
|   Physical exam and vital signs |
|   Begin Prednisone or similar glucocorticoid |
|   Photographs of potential injection site |
|   Safety Labs: |
|     Complete blood count (CBC) with differential and platelets |
|     Serum total protein |
|     Serum gamma-glutamyl transferase (GGT) |
|       GGT will be used to monitor liver enzymes rather than ALT or AST because of the source of these enzymes from damaged muscle, where levels can reach 9-10× ULN. ALT and AST can vary by 30-40% from day to day making interpretation difficult. GGT is not affected by muscle disease [22,23] |
|     Serum total bilirubin |
|     Glucose |
|     Creatine kinase (CK) (CK levels will only be drawn preferably on 2 day visits but may be tested on a one day visit per PI discretion) |
|     Creatinine/BUN |
|     Cystatin C |
|     Alkaline phosphatase |
|     Amylase |
|     AST |
|     ALT |
|     Prothrombin time (PT), partial thromboplastin time (PTT) |
|     Electrolytes (sodium, potassium, chloride, C02) |
|     Urinalysis |

Prophylactic Administration of Prednisone

An expected antigen specific T-cell response to the AAV vector was expected between 2-4 weeks following gene transfer. One possible consequence to such antigen specific T-cell responses was clearance of the transduced cells and loss of transgene expression. To dampen the host immune response to the AAV based therapy, twenty-four hours prior to the procedure subjects were started on approximately 1 mg/kg/day prophylactic prednisone or comparable glucocorticoid by mouth with a maximum dose of 60 mg/day. IV administration of a comparable glucocorticoid at the approximate dose of 1 mg/kg/day was also be allowable if needed. Treatment continued for approximately one month. A tapering protocol for prednisone or comparable glucocorticoid was implemented based on individual subjects' immune response to the gene transfer, assessed by ELISpot assay and also by liver function monitoring with GGT.

Protocol for Gene Transfer

The scAAVrh74.MHCK7.hSGCB gene vector was prepared by the research pharmacist according to the Manual of Operating Procedures (MOOP). Immediately prior to transportation to the clinical setting, appropriate dilutions of the test article were completed by the pharmacy. The vector was diluted using lactated Ringer's and drawn up in sterile 60 ml polypropylene syringes. Documentation of the dilution was completed by the pharmacy following standard pharmacy protocol.

The vector-containing syringes were delivered at room temperature and administered to the subject within 24 hours of preparation. Handling of scAAVrh74.MHCK7.hSGCB followed compliance standards for Biosafety Level 1 vectors. (NIH Guidelines for Research Involving recombinant or Synthetic Acid Molecules [NIH Guidelines], April 2016, Department of Health and Human Services, National Institutes of Health Office of Science Policy, Office of Biotechnology Activities.

Subjects were admitted for gene transfer, either PICU or Pulmonary PICU, the night before gene transfer and were examined by either the PI or Co-Is (DAY −1). Subjects were held NPO after midnight the night before the gene transfer procedure. Procedures were performed under sterile conditions in the hospital room.

An intravenous catheter with heparin lock was placed in a peripheral vein for delivery of vector. A second intravenous catheter was placed to be used in the event of a complication with the first site. Pictures were taken of these sites on the day of the gene transfer. The vector was delivered intravenously while the patient is awake. If deemed necessary by the study doctor, the patient received conscious sedation per protocol. The patient were dosed with scAAVrh74.MHCK7.hSGCB administered over approximately 1-2 hours through 60 mL polypropylene syringes using a syringe pump. The patient's vital signs were monitored during the infusion and every 15 minutes for 4 hours and every hour for the remaining 24 hours post-infusion.

Post-Gene Transfer Monitoring

The patient's vital signs were monitored every 15 minutes for 4 hours and every hour for the remaining 24 hours post-infusion. Safety labs and a urinalysis were checked the day after the procedure. Concomitant medications and all adverse events/serious adverse events were also be monitored and documented following injection. Subjects were discharged one day after gene transfer (if no side effects are observed that are a concern for safety). Subjects returned for follow up visits on days 7, 14, 30, 60, 90, and 180 and months 9, 12, 18, 24, 30 and 36. Toxicity monitoring on each of these dates included:

Physical Exam and vital signs
Safety Labs:
    Complete blood count (CBC) with differential and platelets
    Serum total protein
    Serum gamma-glutamyl transferase (GGT)*
        GGT will be used to monitor liver enzymes rather than ALT or AST because of the source of these enzymes from damaged muscle, where levels can reach 9-10× ULN. ALT and AST can vary by 30-40% from day to day making interpretation difficult. GGT is not affected by muscle disease [22,23]
    Serum total bilirubin
    Glucose
    Creatine kinase (CK) (CK levels will only be drawn preferably on 2 day visits but may be tested on a one day visit per PI discretion)
    Creatinine/BUN
    Cystatin C
    Alkaline phosphatase
    Amylase
    AST
    ALT
    Prothrombin time (PT), partial thromboplastin time (PTT)
    Electrolytes (sodium, potassium, chloride, C02)
    Urinalysis
Immunology studies
Physical Therapy assessments starting at Day 30 (100 meter timed test, strength testing, PROMIS questionnaires, North Star Assessment for Limb Girdle Muscular Dystrophies (NSAD), Ascending 4 stairs, Timed Up and Go and workspace volume)
Urinalysis
Photograph of injection site (Days −1, 0, 1, 7, 14, 30)
Adverse events (collected at all study visits)
EKG (Day 180, Months 12, 24, 36)
Cardiac and skeletal muscle MRI (Months 12, 24, 36),
Pulmonary Function Tests (Days 60, 180, Months 12, 24, 36)
Post gene transfer muscle biopsy at 60 days for Cohort 1 and 2 and at 2 years post treatment for all subjects; choice of muscle will be the same as pre-treatment biopsy sites. The post treatment biopsy will preferably be on the same side unless risks dictate biopsies be done on the opposite limb.

Long-Term Monitoring

The recent FDA guidelines are followed with regard to long-term subject follow-up following gene transfer. As discussed and based on prior experience with rAAV or transgene, there is a very low probability of gene transfer-related delayed adverse events. Short-term safety over a three-year period is evaluated that incorporates the active phase of the protocol. If newly identified risks are associated with the product, or if the subjects suffer any adverse events during this period, a long-term follow-up is initiated according to the FDA guidelines.

CBER is notified if there is any indication of need to extend follow-up period. All subjects will be provided with written instructions on how to contact the Principal Investigator or study coordinator if they experience any serious adverse event that they consider possibly related to study treatment or study participation. This information is included in the Informed Consent document. All subjects are instructed to notify the Principal Investigator of a change of address or contact information.

Post-Study Follow-up

The most recent FDA guidance are followed with regard to long-term subject follow-up post gene transfer. As indicated by the guidelines, the vector has a very low probability of gene transfer-related delayed adverse events. Safety is evaluated over a three-year period post-dosing that incorporates the active phase of the protocol. If newly identified risks are associated with our product, or if the subjects suffer any adverse events during this period, a long-term follow-up is initiated according to the FDA guidelines.

Primary Outcome for Clinical Trial

This is a Phase I clinical trial and safety is the primary outcome. Demonstration of 3-SG protein expression, as judged by quantified immunofluorescent or immunoblot analysis (≥20% above baseline) on muscle biopsy at 8 weeks.

Exploratory Outcomes

Improvement in 100 meter time ≥10% compared to baseline for each participant 3 years post gene transfer A decrease in CK following gene therapy will serve as an exploratory outcome. CK levels will only be drawn preferably on 2 day visits but may be tested on a one day visit per PI discretion Workspace volume Handheld dynamometry of knee and elbow extensors and flexors, hip adductors, and shoulder abductors Improvement in ejection fraction as measured by cMRI Skeletal MRI Pulmonary Function Testing (PFTs), including spirometry Timed Functional Testing [Ascending 4 stairs, Timed Up and Go]

North Star Assessment for Limb Girdle Muscular Dystrophies (NSAD)

Activity level as determined by a Fitbit or similar activity monitoring device

Patient report of physical function using PROMIS Upper Extremity and Mobility questionnaires Cohort 1 Results All subjects in Cohort 1 were doing well at the time of testing (Subjects 1 and 2: tested 90 days post injection; Subject 3 tested 60 days post injection). All subjects continued to do well out to 9 months post injection. There was one serious adverse event in this study, in which one subject demonstrated elevated liver enzymes and bilirubin following discontinuation of steroids. This event was resolved with increased steroids. Two of the subjects had elevated liver enzymes that resolved with increased steroids and these level returned to baseline.

Muscle needle biopsies of the tibialis anterior and biceps were used to quantify transgene expression comparing baseline to day 60 in Cohort 1. The primary endpoint was ≥20% expression of SGCB protein. If expression of SGCB is ≥50% above baseline in all of the treated subjects there will be no increase in dosing. If expression of SGCB is <50% in all treated subjects, the dose will be escalated to $2 \times 10^{14}$ vg/kg for Cohort 2 and the placebo subjects. The 2 year post-treatment biopsies will be done on the same muscle(s) as the baseline biopsies, when possible. All biopsy samples were blinded and coded by the laboratory director with a computer generated code. Quantification of expression was done using direct immunofluorescence and Western Blot studies of the muscle biopsies. Bioquant® automated software will be used to quantify the number of muscle fibers expressing SGCB. Baseline demographics are set out in Table 5.

TABLE 5

| Baseline Demographics | | |
|---|---|---|
| Subject | Age (years) | CK Levels at Baseline (U/L) |
| 1 | 13 | 10,727 |
| 2 | 4 | 12,826 |
| 3 | 13 | 10,985 |

Figure 7:
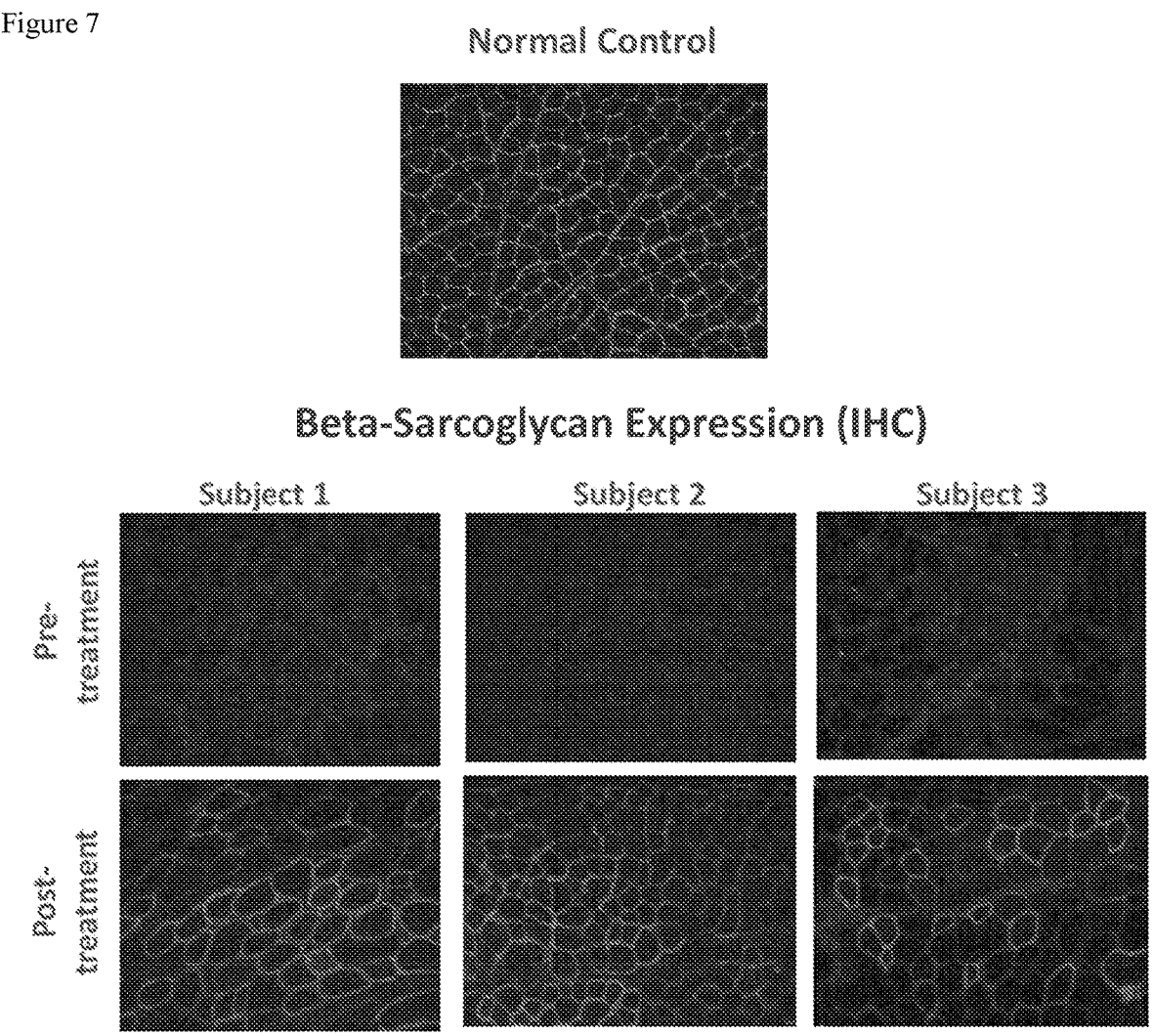
FIG. 7 provides β-sarcoglycan protein expression in muscle biopsies in human subjects after systemic administration of $5.0 \times 10^{13}$ vg/kg scAAVrh.74.MHCK7.hSGCB as detected and quantitated by immunohistochemistry.
Figure 8:
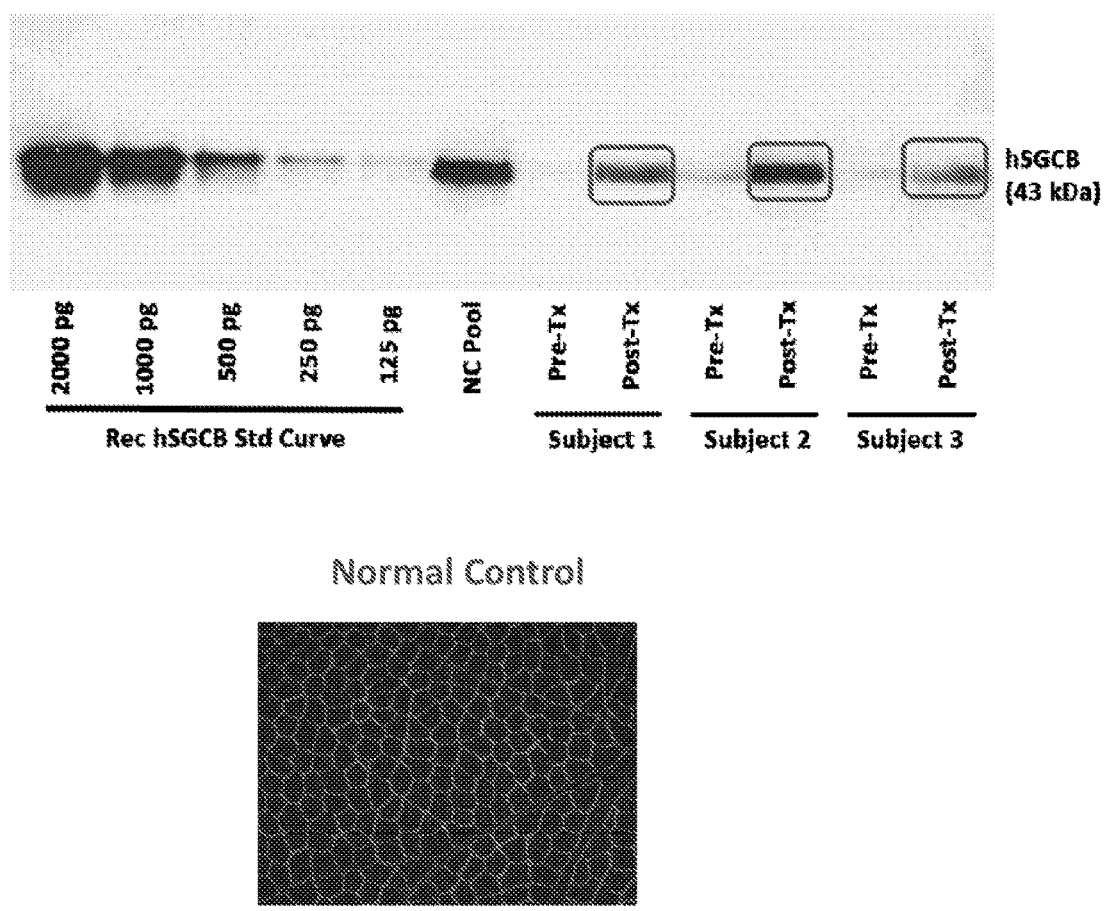
FIG. 8 provides β-sarcoglycan protein expression in muscle biopsies in human subjects 90 days after systemic administration of $5.0 \times 10^{13}$ vg/kg scAAVrh.74.MHCK7.hSGCB as detected and quantitated by Western Blot.

FIG. 7 provides representative images that demonstrate robust SGCB expression in the muscles of all three subjects 8 weeks after vector administration. Table 6 provides the mean intensity and percentage of SGCB-positive fibers in each subject. The mean intensity of immunohistochemistry staining for the entire cohort was 47% and the mean percentage of SGCB-positive fibers was 51%. FIG. 8 provides a Western Blot demonstrating detection of β-sarcoglycan expression in the three subjects 90 days after vector administration. The Western Blot data demonstrates that the gene transfer delivers full length β-sarcoglycan. Quantification by Western Blot is provided in Table 7, which demonstrates a mean β-sarcoglycan protein expression is about 36.1% increased compared to normal.

TABLE 6

| Immunohistochemisty | | |
|---|---|---|
| Subject | Mean Intensity | Percentage of SCGB-Positive Fibers |
| 1 | 47% | 63% |
| 2 | 57% | 49% |
| 3 | 38% | 42% |
| MEAN | 47% | 51% |

TABLE 7

| Western Blot | |
|---|---|
| Subject | Mean Beta-Sarcoglycan Expression (N = 3) vs. Normal |
| 1 | 34.7% |
| 2 | 39.2% |
| 3 | 34.5% |
| MEAN | 36.1% |

The presence of test article-specific DNA sequences was examined using a real time, quantitative PCR assay (qPCR) on the collected muscle biopsies. A positive signal is anything equal to or greater than 100 single-stranded DNA copies/µg genomic DNA detected. A mean 8.4E+04 vector copies/µg DNA, and 0.6 copies per nucleus, was detected in the muscle biopsies.

Figure 9:
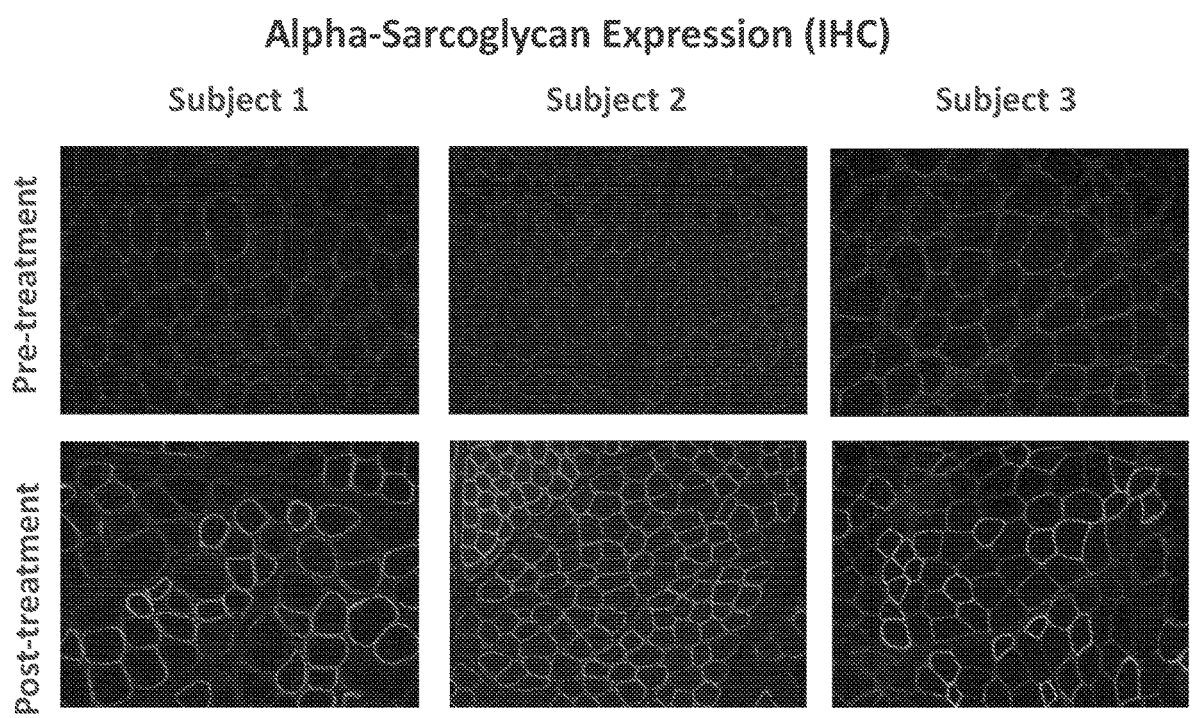
FIG. 9 demonstrates that β-sarcoglycan protein expression upregulated expression of the sarcoglycan complex as indicated by detection and quantification of alpha-sarcoglycan by immunohistochemistry.

The presence of the sarcoglycan complex in each subject was also investigated. As determined by Western Blot, mean micro-dystrophin expression was 36% of normal (n=3). In addition, alpha-sarcoglycan expression was quantified by immunohistochemistry. FIG. 9 demonstrates that beta-sarcoglycan expression in the subjects upregulated the sarcoglycan complex as indicated by alpha-sarcoglycan expression.

The creatine kinase (CK) levels in the blood of the subject were tested. As shown in Table 9, there was a mean reduction of about 82% in CK levels in the subjects.

TABLE 9

| | | CK Levels (U/L) at | | | | | |
|---|---|---|---|---|---|---|---|
| Subject | Age | Baseline | Day 30 | Day 60 | Day 90 | Day 180 | Day 270 |
| 1 | 13 | 10,727 | 619 | 2257 | 1135 | 1553 | 2300 |
| 2 | 4 | 12,826 | 4795 | 910 | 2159 | 5070 | 2665 |
| 3 | 13 | 10,985 | 687 | 2061 | 2392 | 10,055 | 1295 |

Example 6

β-Sarcoglycan Gene Transfer Restores Sarcoglycan Complex to the Membrane

Figure 10:
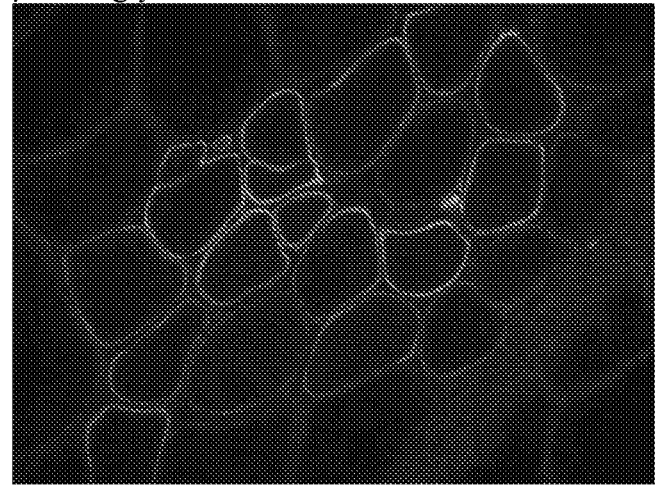
FIG. 10 shows the restoration of expression of p-sarcoglycan, α-sarcoglycan, and the colocalization of both β-sarcoglycan and α-sarcoglycan at the membrane for patient #3 in the trial.
Figure 10:
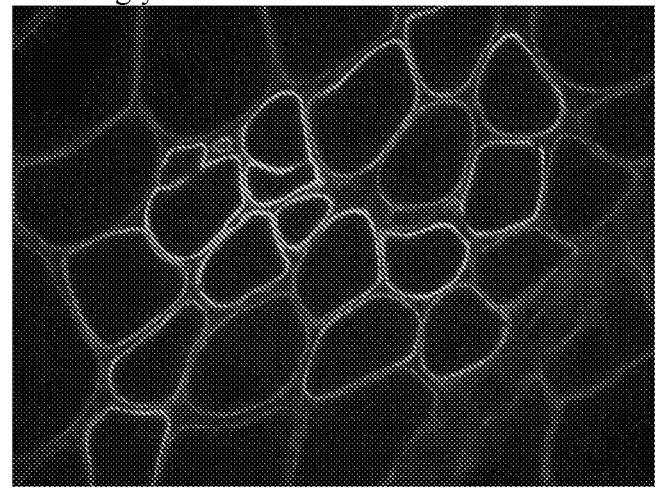
Figure 10:
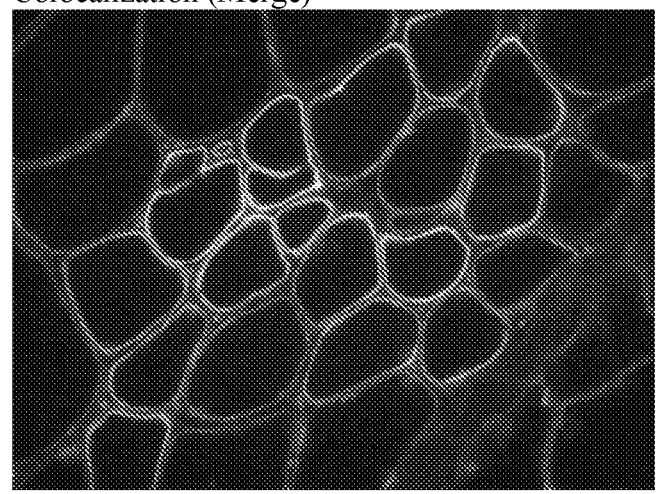

Treatment with scAAVrh74.MHCK7.hSGCB restored sarcoglycan complex to the membrane (FIG. 10). FIG. 10 shows the restoration of expression of β-sarcoglycan, α-sarcoglycan, and the colocalization of both β-sarcoglycan and α-sarcoglycan at the membrane for a patient in the trial. Co-localization of β-sarcoglycan and α-sarcoglycan indicates that scAAVrh74.MHCK7.hSGCB restored the sarcoglycan complex.

Example 7

LGMD2E Patients Treated with β-Sarcoglycan Gene Transfer Improved on the 100 Meter Timed Test at Three Months Post-Administration Treatment with scAAVrh74.MHCK7.hSGCB provided patients with demonstrable improvement in the 100 meter timed test over only a 3-month period following gene transfer (FIG. 11). Timed walking tests, like the 100 meter timed test, are used to measure function in subjects with a muscular dystrophy. The test in this study measured the patients baseline performance compared to their performance after treatment. FIG. 11 shows the mean percent change from baseline in three subjects over the first three months post-gene transfer. The data show that there was a greater than 15% mean increase over baseline after 3 months, demonstrating the improvement in motor function after β-sarcoglycan gene transfer.

Example 8

LGMD2E Patients Treated with β-Sarcoglycan Gene Transfer Showed Improved Functional Measures at Nine Months Post-Administration Treatment with scAAVrh74.MHCK7.hSGCB provided patients with demonstrable and improvement nine months following systemic administration of scAAVrh.74.MHCK7.hSGCB. Three patients participated the functional study. For example, in a 100 m timed test, at the baseline (before administration) one patient had limited hip extension and flexion when running the 100 m. However, at 9 months post-administration, the same patient showed improved hip extension and flexion and a faster speed when running. In addition, for the trunk control test, another patient showed an improvement in the time to rise test 9 months after post-administration. At baseline or before administration, the subjects showed poor trunk control but this was also improved 9 months post-administration. Also, in the sitting up test, the patients were asked to sit up from the sitting position. The remaining patient, for example, showed a shortened getting up time 9-month post administration as compared to that before administration. These data are summarized in Table 10.

TABLE 10

| Subject | Assessment | NSAD (Δ) | Time to Rise (sec) | 4 Stairs Up (sec) | 100 m (sec) | 10 m (sec) |
|---|---|---|---|---|---|---|
| 1 | Baseline | 40 | 5.0 | 2.4 | 49.3 | 5 |
|   | Day 270 | 41 | 4.1 | 2.3 | 43.2 | 4.5 |
| 2 | Baseline | 41 | 3.5 | 2.8 | 49.9 | 5.2 |
|   | Day 270 | 47 | 3.0 | 1.9 | 48.6 | 4.3 |
| 3 | Baseline | 48 | 1.5 | 1.6 | 59.3 | 3.4 |
|   | Day 270 | 54 | 1.2 | 1.3 | 48.4 | 3.2 |

Figure 12A:
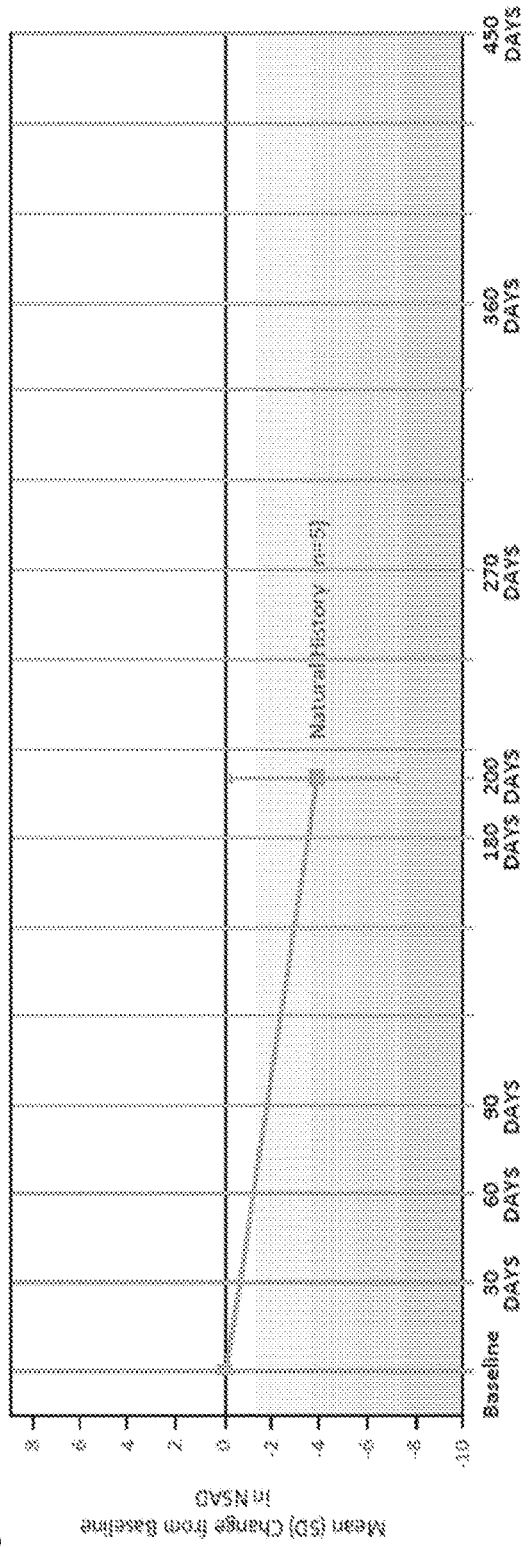
FIG. 12A-C provide the change from baseline in the North Star Assessment for Limb Girdle Muscular Dystrophies (NSAD) for the natural history control group (FIG. 12A) and for the test subjects after administration of $5.0 \times 10^{13}$ vg/kg scAAVrh.74.MHCK7.hSGCB (FIG. 12B). The NSAD data for six individual natural history control patients are shown in FIG. 12C.
Figure 12B:
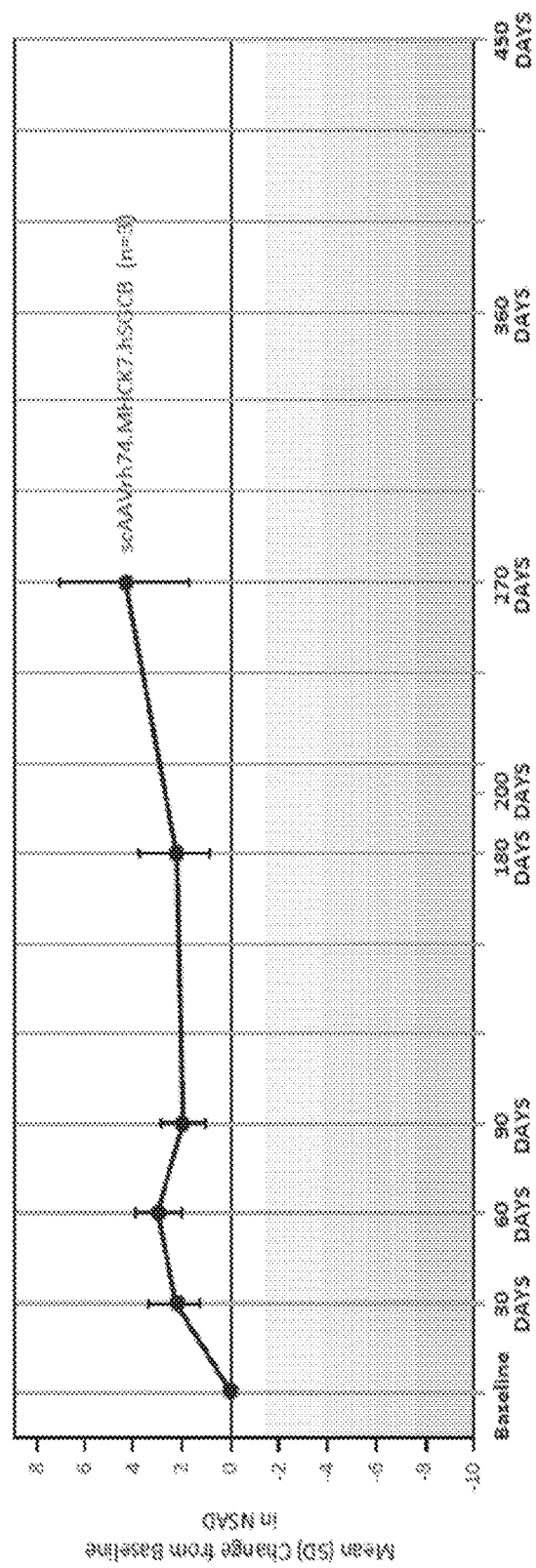
Figure 12C:
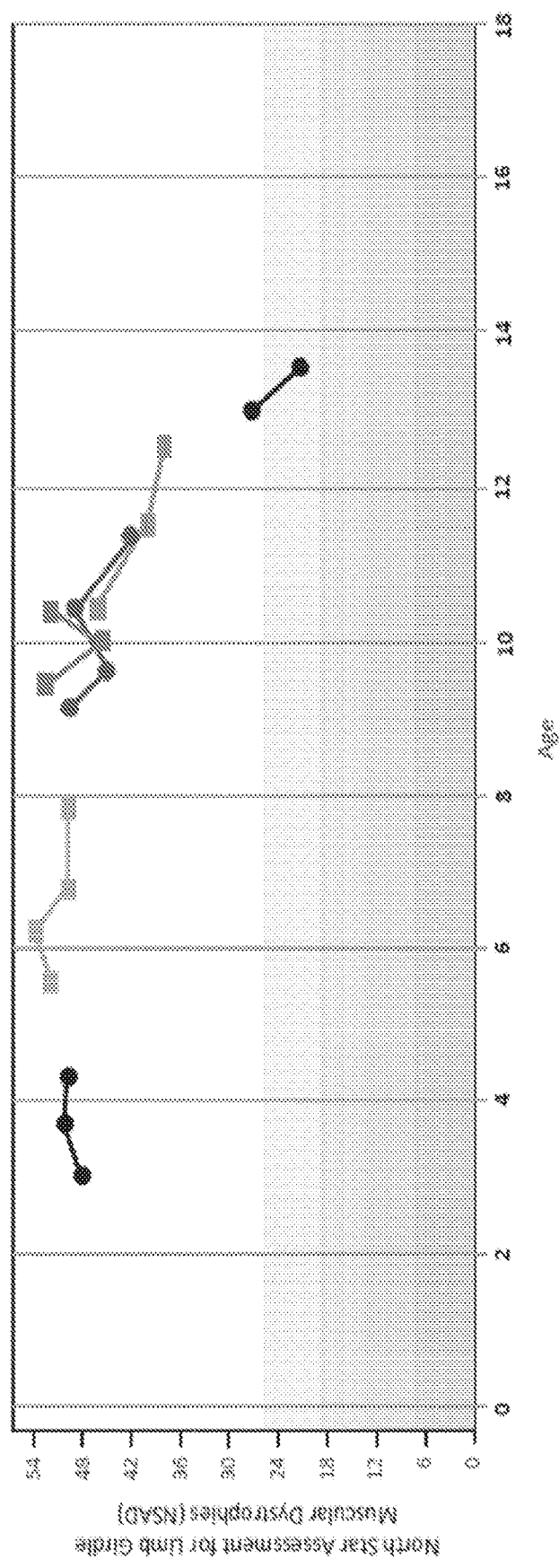
Figure 13:
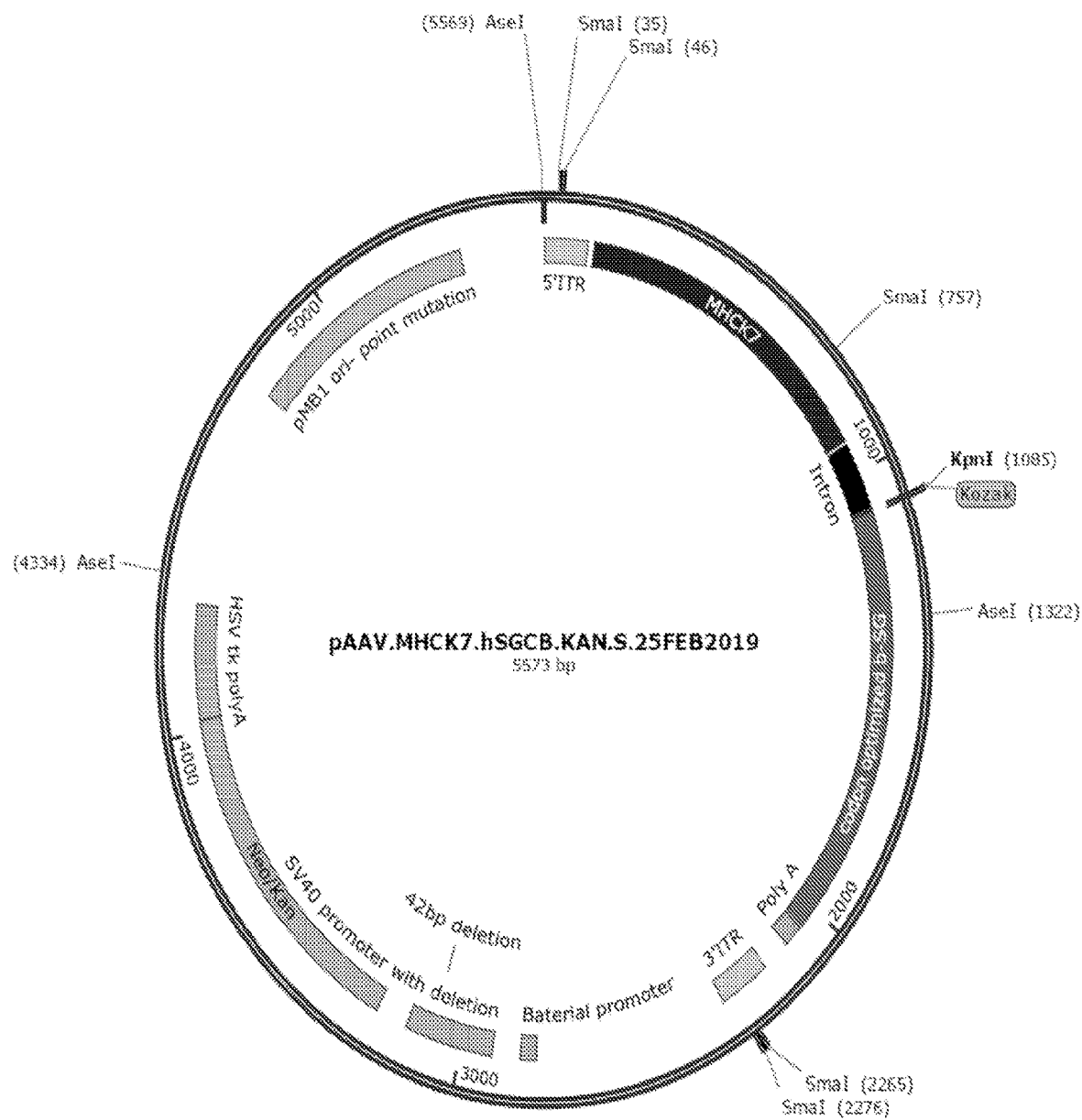
FIG. 13 provides a schematic map of pAAV.MHCK7.hSGCB. KAN AAV vector plasmid.

An age matched natural history study compared the change from baseline in the NSAD, herein denoted as "North Star Assessment for Limb Girdle Muscular Dystrophies," for untreated subjects (denoted as natural history subjects; see Table 11) and subjects administered scAAVrh74.MHCK7.hSGCB. As shown in FIGS. 12A-C, the natural history subjects had a steady decreased in change in NSAD over 200 days, while the treated subjects showed a steady improvement in change in NSAD over 270 days (FIGS. 12A and 12C), while the treated subject showed a steady improvement in change in NSAD over 270 days (FIG. 12B).

TABLE 11

| Subject | Age (years) |
|---|---|
| 1 | 5 |
| 2 | 12 |
| 3 | 10 |
| 4 | 9 |
| 5 | 9 |

Example 9

Formulations scAAVrh74.MHCK7.hSGCB is formulated in a buffer containing 20 mM Tris (pH 8.0), 1 mM magnesium chloride ($MgCl_2$), 200 mM sodium chloride (NaCl), and 0.001% Poloxamer 188. In one embodiment, the formulation information is summarized in Table 12.

TABLE 12

| Formulation (as Frozen Liquid) | |
|---|---|
| Component | Concentration |
| scAAVrh.74.MHCK7.hSGCB | $2 \times 10^{13}$ vg/ml, $5 \times 10^{13}$ vg/ml, or $4 \times 10^{13}$ vg/ml $^a$ |
| Tris (pH 8.0) | 20 mM |
| Magnesium Chloride (MgCl2) | 1 mM |
| Sodium Chloride (NaQ) | 200 mM |
| Poloxamer 188 | 0.001% |

The drug product is stored as a frozen liquid at temperatures below −60° C. The frozen drug product must be thawed prior to clinical administration.

scAAVrh74.MHCK7.hSGCB is stored at temperatures below −60° C., under which the material is stable under the long-term storage condition. scAAVrh74.MHCK7.hSGCB vials are thawed at room temperature (20° C. to 25° C.). Thawed vector vials are wiped with alcohol and placed in the biosafety cabinet. The scAAVrh74.MHCK7.hSGCB formulation is prepared aseptically in a Class II biosafety cabinet under sterile conditions.

The scAAVrh74.MHCK7.hSGCB for intravenous (IV) infusion is supplied in a vial (2 mL per vial). The total vg dose is calculated based on the patient's body weight. The appropriate number of vials is determined for each patient based on body weight at the equivalent of $5\times10^{13}$ vg/kg or $2\times10^{14}$ vg/kg, as well as product titer for the scAAVrh74.MHCK7.hSGCB lot of $2\times10^{13}$ vg/mL, $5\times10^{13}$ vg/mL, or $4\times10^{13}$ vg/ml.

The scAAVrh74.MHCK7.hSGCB is administered as a one-time IV infusion, delivered over approximately 1 to 2 hours via syringe pump into a peripheral limb vein.

Example 10

Elder Patients and Durability scAAVrh74.MHCK7.hSGCB-mediated gene replacement has shown positive results in treating LGMD-2E and other associated diseases. The study is to test the ability of scAAVrh74.MHCK7.hSGCB to treat older more severely affected muscle, and the long-term durability of the AAV viral vector. First, for the long-term durability study, sgcb$^{-/-}$ mice at 4 weeks of age were treated systemically with scAAVrh74.MHCK7.hSGCB. More than 24 months post-treatment, high-level vector genome copy numbers were detected with PCR across all transduced muscles. Moreover, immunofluorescence staining of treated muscle showed no decrease of protein expression levels in all muscles (>95%) compared to earlier timepoints, with hSGCB protein remaining correctly localized at the membrane.

Second, a mouse model of LGMD2E (β-sarcoglycan) is treated at older age (e.g., 12 month) with systemic delivery of an scAAVrh74.MHCK7.hSGCB vector. At the 6-month endpoint post treatment, the muscle from these mice are evaluated for protein expression, histological rescue, and functional improvement. In particular, the gene expression in muscles throughout the lower limb, upper limb, and proximal torso muscles, including the diaphragm and heart, is observed. Moreover, the level of fibrosis is compared to untreated controls. Further, a functional study involves evaluation of force output in the tibialis anterior (TA) and diaphragm (DIA) muscle and resistance to contraction-induced injury in the TA muscle.

While the present disclosure has been described in terms of specific embodiments, it is understood that variations and modifications will occur to those skilled in the art. Accordingly, only such limitations as appear in the claims should be placed on the disclosure.

All documents referred to in this application are hereby incorporated by reference in their entirety.

REFERENCES

1 Bonnemann C G, Modi R, Noguchi S, Mizuno Y, Yoshida M, Gussoni E et al. Beta-sarcoglycan (A3b) mutations cause autosomal recessive muscular dystrophy with loss of the sarcoglycan complex. Nat Genet 1995; 11: 266-273.
2 Moore S A, Shilling C J, Westra S, Wall C, Wicklund M P, Stolle C et al. Limb-girdle muscular dystrophy in the United States. J Neuropathol Exp Neurol 2006; 65: 995-1003.
3 Araishi K, Sasaoka T, Imamura M, Noguchi S, Hama H, Wakabayashi E et al. Loss of the sarcoglycan complex and sarcospan leads to muscular dystrophy in beta-sarcoglycan-deficient mice. Hum Mol Genet 1999; 8: 1589-1598.
4 Durbeej M, Cohn R D, Hrstka R F, Moore S A, Allamand V, Davidson B L et al. Disruption of the beta-sarcoglycan gene reveals pathogenetic complexity of limb-girdle muscular dystrophy type 2E. Mol Cell 2000; 5: 141-151.
5 Bonnemann C G, Passos-Bueno M R, McNally E M, Vainzof M, de Sa Moreira E, Marie S K et al. Genomic screening for beta-sarcoglycan gene mutations: missense mutations may cause severe limb-girdle muscular dystrophy type 2E (LGMD 2E). Hum Mol Genet 1996; 5: 1953-1961.
6 Angelini C, Fanin M, Freda M P, Duggan D J, Siciliano G, Hoffman E P. The clinical spectrum of sarcoglycanopathies. Neurology 1999; 52: 176-179.
7 Sandona D, Betto R. Sarcoglycanopathies: molecular pathogenesis and therapeutic prospects. Exp Rev Mol Med 2009; 11: e28.
8 Fanin M, Melacini P, Boito C, Pegoraro E, Angelini C. LGMD2E patients risk developing dilated cardiomyopathy. Neuromusc Disord 2003; 13: 303-309.
9 Sveen M L, Thune J J, Kober L, Vissing J. Cardiac involvement in patients with limb-girdle muscular dystrophy type 2 and Becker muscular dystrophy. Arch Neurol 2008; 65: 1196-1201.
10 Melacini P, Fanin M, Duggan D J, Freda M P, Berardinelli A, Danieli G A et al. Heart involvement in muscular dystrophies due to sarcoglycan gene mutations. Muscle Nerve 1999; 22: 473-479.
11 Narayanaswami P, Weiss M, Selcen D, David W, Raynor E, Carter G et al. Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine. Neurology 2014; 83: 1453-1463.
12 Wong-Kisiel L C, Kuntz N L. Two siblings with limb-girdle muscular dystrophy type 2E responsive to deflazacort. Neuromusc Disord 2010; 20: 122-124.
13 Barresi R, Di Blasi C, Negri T, Brugnoni R, Vitali A, Felisari G et al. Disruption of heart sarcoglycan complex and severe cardiomyopathy caused by beta sarcoglycan mutations. J Med Genet 2000; 37: 102-107.
14 Gibertini S, Zanotti S, Savadori P, Curcio M, Saredi S, Salerno F et al. Fibrosis and inflammation are greater in muscles of beta-sarcoglycan-null mouse than mdx mouse. Cell Tissue Res 2014; 356: 427-443.
15 McCarty D M, Fu H, Monahan P E, Toulson C E, Naik P, Samulski R J. Adeno-associated virus terminal repeat (TR) mutant generates self-complementary vectors to overcome the rate-limiting step to transduction in vivo. Gene Ther 2003; 10: 2112-2118.
16 McCarty D M, Monahan P E, Samulski R J. Self-complementary recombinant adeno-associated virus (scAAV) vectors promote efficient transduction independently of DNA synthesis. Gene Ther 2001; 8: 1248-1254.
17 Chicoine L G, Rodino-Klapac L R, Shao G, Xu R, Bremer W G, Camboni M et al. Vascular delivery of rAAVrh74.MCK.GALGT2 to the gastrocnemius muscle of the rhesus macaque stimulates the expression of dystrophin and laminin alpha2 surrogates. Mol Ther 2014; 22: 713-724.
18 Rodino-Klapac L R, Montgomery C L, Bremer W G, Shontz K M, Malik V, Davis N et al. Persistent expression of FLAG-tagged micro dystrophin in nonhuman primates following intramuscular and vascular delivery. Mol Ther 2010; 18: 109-117.
19 Rodino-Klapac L R, Janssen P M, Montgomery C L, Coley B D, Chicoine L G, Clark K R et al. A translational approach for limb vascular delivery of the micro-dystro- 20. Wang B, Li J, Fu F H, Chen C, Zhu X, Zhou L et al. Construction and analysis of compact muscle-specific promoters for AAV vectors. Gene Ther 2008; 15: 1489-1499.
21. Chicoine L G, Montgomery C L, Bremer W G, Shontz K M, Griffin D A, Heller K N et al. Plasmapheresis eliminates the negative impact of AAV antibodies on microdystrophin gene expression following vascular delivery. Mol Ther 2014; 22: 338-347.
22. Matsuda R, Nishikawa A, Tanaka H. Visualization of dystrophic muscle fibers in mdx mouse by vital staining with Evans blue: evidence of apoptosis in dystrophin-deficient muscle. J Biochem 1995; 118: 959-964.
23. Straub V, Rafael J A, Chamberlain J S, Campbell K P. Animal models for muscular dystrophy show different patterns of sarcolemmal disruption. J Cell Biol 1997; 139: 375-385.
24. Mendell J R, Sahenk Z, Malik V, Gomez A M, Flanigan K M, Lowes L P et al. A phase 1/2a follistatin gene therapy trial for becker muscular dystrophy. Mol Ther 2015; 23: 192-201.
25. Dressman D, Araishi K, Imamura M, Sasaoka T, Liu L A, Engvall E et al. Delivery of alpha- and beta-sarcoglycan by recombinant adeno-associated virus: efficient rescue of muscle, but differential toxicity. Hum Gene Ther 2002; 13: 1631-1646.
26. Rodino-Klapac L R, Lee J S, Mulligan R C, Clark K R, Mendell J R. Lack of toxicity of alpha-sarcoglycan overexpression supports clinical gene transfer trial in LGMD2D. Neurology 2008; 71: 240-247.
27. Shield M A, Haugen H S, Clegg C H, Hauschka S D. E-box sites and a proximal regulatory region of the muscle creatine kinase gene differentially regulate expression in diverse skeletal muscles and cardiac muscle of transgenic mice. Mol Cell Biol 1996; 16: 5058-5068.
28. Rabinowitz J E, Rolling F, Li C, Conrath H, Xiao W, Xiao X et al. Cross-packaging of a single adeno-associated virus (AAV) type 2 vector genome into multiple AAV serotypes enables transduction with broad specificity. J Virol 2002; 76: 791-801.
29. Grieger J C, Choi V W, Samulski R J. Production and characterization of adeno-associated viral vectors. Nat Protoc 2006; 1: 1412-1428.
30. Clark K R, Liu X, McGrath J P, Johnson P R. Highly purified recombinant adeno-associated virus vectors are biologically active and free of detectable helper and wild-type viruses. Hum Gene Ther 1999; 10: 1031-1039.
31. Liu M, Yue Y, Harper S Q, Grange R W, Chamberlain J S, Duan D. Adeno-associated virus-mediated microdystrophin expression protects young mdx muscle from contraction-induced injury. Mol Ther 2005; 11: 245-256.
32. Hakim C H, Grange R W, Duan D. The passive mechanical properties of the extensor digitorum longus muscle are compromised in 2- to 20-mo-old mdx mice. J Appl Physiol 2011; 110:1656-1663.
33. Wein N, Vulin A, Falzarano M S, Szigyarto C A, Maiti B, Findlay A et al. Translation from a DMD exon 5 IRES results in a functional dystrophin isoform that attenuates dystrophinopathy in humans and mice. Nat Med 2014; 20: 992-1000.

---

What is claimed is:

1. A method of treating limb-girdle muscular dystrophy Type 2E ("LGMD2E") in a subject in need thereof, comprising the step of administering a recombinant adeno-associated virus (rAAV) which comprises SEQ ID NO: 19 to the subject, wherein the rAAV is administered using a systemic route of administration and at a dose of a) about $1.85 \times 10^{13}$ vg/kg or about $7.41 \times 10^{13}$ vg/kg based on a linearized plasmid as the quantitation standard, or b) about $1.0 \times 10^{13}$ vg/kg or about $5.0 \times 10^{14}$ vg/kg based on a supercoiled plasmid as the quantitation standard.

2. A method of treating limb-girdle muscular dystrophy Type 2E ("LGMD2E") in a subject in need thereof, comprising the step of administering a recombinant adeno-associated virus (rAAV) which comprises SEQ ID NO: 19 to the subject, wherein administration of the rAAV decreases the serum creatine kinase (CK) level in the subject as compared to the serum CK level before the administration of the rAAV.

3. The method of claim 1, wherein the rAAV is administered using an intravenous route.

4. The method of claim 2, wherein the rAAV is administered at about $1.0 \times 10^{13}$ vg/kg or about $5.0 \times 10^{14}$ vg/kg based on a supercoiled plasmid as the quantitation standard, or about $1.85\times10^{13}$ vg/kg or $7.41\times10^{13}$ vg/kg based on a linearized plasmid as the quantitation standard.

5. The method of claim 1, wherein the rAAV comprises one or more of the following:
(i) nucleotide sequence of SEQ ID NO: 1,
(ii) the MHCK7 promoter sequence of SEQ ID NO: 4,
(iii) an intron sequence of SEQ ID NO: 20,
(iv) a polyA sequence of SEQ ID NO: 21,
(v) 5' inverted terminal repeat (ITR) sequence of SEQ ID NO: 22, and
(vi) 3' inverted terminal repeat (ITR) sequence of SEQ ID NO: 23.

6. The method of claim 1, wherein the rAAV is administered at a dose of about $1.0\times10^{13}$ vg/kg to about $1.0\times10^{14}$ vg/kg based on a supercoiled plasmid as the quantitation standard.

7. A method of treating limb-girdle muscular dystrophy Type 2E in a subject in need, comprising administering to the subject an intravenous infusion of an rAAV construct over approximately 1 to 2 hours at a dose of about $5.0\times10^{13}$ vg/kg or about $2.0\times10^{14}$ vg/kg based on a supercoiled plasmid as the quantitation standard, or about $1.85\times10^{13}$ vg/kg or $7.41\times10^{13}$ vg/kg based on a linearized plasmid as the quantitation standard, and wherein the rAAV construct comprises SEQ ID NO: 19.

8. The method of claim 1, wherein the subject is a human subject that is (i) 4 to 15 years of age, (ii) 25 to 55 years of age, or (iii) over 50 years of age.

9. The method of claim 1, wherein the rAAV is administered using a systemic route of administration and at a dose of $7.41\times10^{13}$ vg/kg based on a linearized plasmid as the quantitation standard.

10. A method of increasing localization of alpha-sarcoglycan to a cell membrane in a subject in need thereof comprising administering to the subject a recombinant adeno-associated virus (rAAV) construct which comprises SEQ ID NO: 19.

\* \* \* \* \*

SEQUENCE LISTING

```
<160> NUMBER OF SEQ ID NOS: 24

<210> SEQ ID NO 1
<211> LENGTH: 957
<212> TYPE: DNA
<213> ORGANISM: Homo sapiens
<220> FEATURE:
<221> NAME/KEY: misc_feature
<223> OTHER INFORMATION: Beta-sarcoglycan

<400> SEQUENCE: 1 atgcagcag cagccgccgc agccgccgag cagcagtcaa gcaatggacc agtgaaaaaa      60
tcaatgagag aaaaagccgt cgagaggaga tcagtgaata aggagcacaa cagcaatttc     120
aaagccggct acatccctat tgacgaagat cgcctgcata agacaggcct gaggggggc      180 aaaggaaacc tggcaatctg cgtcatcatt ctgctgttta tcctggccgt gattaatctg     240
atcattactc tggtgatttg ggctgtcatc cgcattggcc aaacggtg tgactctatg       300 gagttccacg aaagtggcct gctgcgattt aagcaggtgt ccgatatggg ggtcatccat    360
ccactgtaca aatctactgt cggcgggcgg agaaacgaga atctggtgat cacccgggaac   420 aatcagccca ttgtgttcca gcagggaacc acaaagctgt ctgtggaaaa caataaaaca    480
tcaatcacta gcgacattgg catgcagttc tttgatcccc ggacccagaa tatcctgttc    540
agtaccgact atgagacaca cgaatttcat ctgccttccg gggtgaagtc tctgaacgtc    600
cagaaagcca gcactgagag aatcaccagt aacgctacat cagacctgaa tatcaaggtg    660
gatggacgag ctattgtccg gggaaatgag ggcgtgttca tcatgggcaa gacaattgaa    720
tttcacatgg gaggcaacat ggagctgaaa gcagaaaaca gcatcattct gaatgggagc    780
```

-continued

```
gtgatggtct ccactaccag actgcccagc tcctctagtg gagaccagct ggggtccgga    840
gattgggtca ggtataagct gtgcatgtgt gccgatggca ccctgtttaa agtgcaggtc    900
accagccaga atatgggatg tcagattagc gataacccctt gtgggaatac tcattaa      957
```

<210> SEQ ID NO 2
<211> LENGTH: 318
<212> TYPE: PRT
<213> ORGANISM: Homo sapiens
<220> FEATURE:
<221> NAME/KEY: MISC_FEATURE
<223> OTHER INFORMATION: Beta-sarcoglycan

<400> SEQUENCE: 2

```
Met Ala Ala Ala Ala Ala Ala Ala Glu Gln Gln Ser Ser Asn Gly
1               5                   10                  15

Pro Val Lys Lys Ser Met Arg Glu Lys Ala Val Glu Arg Arg Ser Val
            20                  25                  30

Asn Lys Glu His Asn Ser Asn Phe Lys Ala Gly Tyr Ile Pro Ile Asp
        35                  40                  45

Glu Asp Arg Leu His Lys Thr Gly Leu Arg Gly Arg Lys Gly Asn Leu
    50                  55                  60

Ala Ile Cys Val Ile Ile Leu Leu Phe Ile Leu Ala Val Ile Asn Leu
65                  70                  75                  80

Ile Ile Thr Leu Val Ile Trp Ala Val Ile Arg Ile Gly Pro Asn Gly
                85                  90                  95

Cys Asp Ser Met Glu Phe His Glu Ser Gly Leu Leu Arg Phe Lys Gln
            100                 105                 110

Val Ser Asp Met Gly Val Ile His Pro Leu Tyr Lys Ser Thr Val Gly
        115                 120                 125

Gly Arg Arg Asn Glu Asn Leu Val Ile Thr Gly Asn Asn Gln Pro Ile
    130                 135                 140

Val Phe Gln Gln Gly Thr Thr Lys Leu Ser Val Glu Asn Asn Lys Thr
145                 150                 155                 160

Ser Ile Thr Ser Asp Ile Gly Met Gln Phe Phe Asp Pro Arg Thr Gln
                165                 170                 175

Asn Ile Leu Phe Ser Thr Asp Tyr Glu Thr His Glu Phe His Leu Pro
            180                 185                 190

Ser Gly Val Lys Ser Leu Asn Val Gln Lys Ala Ser Thr Glu Arg Ile
        195                 200                 205

Thr Ser Asn Ala Thr Ser Asp Leu Asn Ile Lys Val Asp Gly Arg Ala
    210                 215                 220

Ile Val Arg Gly Asn Glu Gly Val Phe Ile Met Gly Lys Thr Ile Glu
225                 230                 235                 240

Phe His Met Gly Gly Asn Met Glu Leu Lys Ala Glu Asn Ser Ile Ile
                245                 250                 255

Leu Asn Gly Ser Val Met Val Ser Thr Thr Arg Leu Pro Ser Ser Ser
            260                 265                 270

Ser Gly Asp Gln Leu Gly Ser Gly Asp Trp Val Arg Tyr Lys Leu Cys
        275                 280                 285

Met Cys Ala Asp Gly Thr Leu Phe Lys Val Gln Val Thr Ser Gln Asn
    290                 295                 300

Met Gly Cys Gln Ile Ser Asp Asn Pro Cys Gly Asn Thr His
305                 310                 315
```

```
<210> SEQ ID NO 3
<211> LENGTH: 2306
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: pAAV.MHCK7.hSCGB

<400> SEQUENCE: 3
ctgcgcgctc gctcgctcac tgaggccgcc cgggcaaagc ccgggcgtcg ggcgaccttt      60
ggtcgcccgg cctcagtgag cgagcgagcg cgcagagagg gagtgggtt aaccaattgg     120 cgcggccgca agcttgcatg tctaagctag acccttcaga ttaaaaataa ctgaggtaag    180
ggcctgggta ggggaggtgg tgtgagacgc tcctgtctct cctctatctg cccatcggcc    240 cttggggag gaggaatgtg cccaaggact aaaaaaaggc catggagcca gaggggcgag    300
ggcaacagac ctttcatggg caaaccttgg ggccctgctg tctagcatgc cccactacgg    360
gtctaggctg cccatgtaag gaggcaaggc ctggggacac ccgagatgcc tggttataat    420
taacccagac atgtggctgc ccccccccc ccaacacctg ctgcctctaa aaataaccct    480
gtccctggtg gatcccctgc atgcgaagat cttcgaacaa ggctgtgggg gactgagggc    540
aggctgtaac aggcttgggg gccagggctt atacgtgcct gggactccca aagtattact    600
gttccatgtt cccggcgaag ggccagctgt cccccgccag ctagactcag cacttagttt    660
aggaaccagt gagcaagtca gcccttgggg cagcccatac aaggccatgg ggctgggcaa    720
gctgcacgcc tgggtccggg gtgggcacgg tgcccgggca acgagctgaa agctcatctg    780
ctctcagggg cccctccctg gggacagccc ctcctggcta gtcacaccct gtaggctcct    840
ctatataacc caggggcaca ggggctgccc tcattctacc accacctcca cagcacagac    900
agacactcag gagcagccag cggcgcgccc aggtaagttt agtctttttg tcttttattt    960
caggtcccgg atccggtggt ggtgcaaatc aaagaactgc tcctcagtgg atgttgcctt   1020
tacttctagg cctgtacgga agtgttactt ctgctctaaa agctgcggaa ttgtacccgg   1080
taccgccacc atggcagcag cagccgccgc agccgccgag cagcagtcaa gcaatggacc   1140
agtgaaaaaa tcaatgagag aaaaagccgt cgagaggaga tcagtgaata aggagcacaa   1200
cagcaatttc aaagccggct acatccctat tgacgaagat cgcctgcata agacaggcct   1260 gaggggggcgc aaaggaaacc tggcaatctg cgtcatcatt ctgctgttta tcctggccgt   1320
gattaatctg atcattactc tggtgatttg ggctgtcatc cgcattggcc caaacgggtg   1380
tgactctatg gagttccacg aaagtggcct gctgcgattt aagcaggtgt ccgatatggg   1440
ggtcatccat ccactgtaca aatctactgt cggcgggcgg agaaacgaga atctggtgat   1500
caccgggaac aatcagccca ttgtgttcca gcagggaacc acaaagctgt ctgtggaaaa   1560
caataaaaca tcaatcacta gcgacattgg catgcagttc tttgatcccc ggacccagaa   1620
tatcctgttc agtaccgact atgagacaca cgaatttcat ctgccttccg gggtgaagtc   1680
tctgaacgtc cagaaagcca gcactgagag aatcaccagt aacgctacat cagacctgaa   1740
tatcaaggtg gatggacgag ctattgtccg gggaaatgag ggcgtgttca tcatgggcaa   1800
gacaattgaa tttcacatgg gaggcaacat ggagctgaaa gcagaaaaca gcatcattct   1860
gaatgggagc gtgatggtct ccactaccag actgcccagc tcctctagtg agaccagct    1920 gggggtccgga gattgggtca ggtataagct gtgcatgtgt gccgatggca ccctgtttaa    1980
agtgcaggtc accagccaga atatgggatg tcagattagc gataaccctt gtgggaatac   2040
```

| tcattaaaag cttggccgca ataaaagatc tttattttca ttagatctgt gtgttggttt | 2100 |
| tttgtgtgtc ctgcaggggc gcgcctctag agcatggcta cgtagataag tagcatggcg | 2160 |
| ggttaatcat taactacaag gaaccccctag tgatggagtt ggccactccc tctctgcgcg | 2220 |
| ctcgctcgct cactgaggcc gggcgaccaa aggtcgcccg acgcccgggc tttgcccggg | 2280 |
| cggcctcagt gagcgagcga gcgcgc | 2306 |

<210> SEQ ID NO 4
<211> LENGTH: 792
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: MHCK7 promoter

<400> SEQUENCE: 4

| aagcttgcat gtctaagcta gacccttcag attaaaaata actgaggtaa gggcctgggt | 60 |
| aggggaggtg gtgtgagacg ctcctgtctc tcctctatct gcccatcggc cctttgggga | 120 |
| ggaggaatgt gcccaaggac taaaaaaagg ccatggagcc agaggggcga gggcaacaga | 180 |
| cctttcatgg gcaaaccttg gggccctgct gtctagcatg ccccactacg ggtctaggct | 240 |
| gcccatgtaa ggaggcaagg cctggggaca cccgagatgc ctggttataa ttaacccaga | 300 |
| catgtggctg ccccccccccc cccaacacct gctgcctcta aaaataaccc tgtccctggt | 360 |
| ggatcccctg catgcgaaga tcttcgaaca aggctgtggg ggactgaggg caggctgtaa | 420 |
| caggcttggg ggccagggct tatacgtgcc tgggactccc aaagtattac tgttccatgt | 480 |
| tcccggcgaa gggccagctg tccccgcca gctagactca gcacttagtt taggaaccag | 540 |
| tgagcaagtc agcccttggg gcagcccata caaggccatg gggctgggca agctgcacgc | 600 |
| ctgggtccgg ggtgggcacg gtgcccgggc aacgagctga aagctcatct gctctcaggg | 660 |
| gcccctccct ggggacagcc cctcctggct agtcacaccc tgtaggctcc tctatataac | 720 |
| ccaggggcac aggggctgcc ctcattctac caccacctcc acagcacaga cagacactca | 780 |
| ggagcagcca gc | 792 |

<210> SEQ ID NO 5
<211> LENGTH: 2244
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: pAAV.tMCK.hSGCB

<400> SEQUENCE: 5

| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgggggtt aaccaattgg | 120 |
| cggccgcaaa cttgcatgcc ccactacggg tctaggctgc ccatgtaagg aggcaaggcc | 180 |
| tggggacacc cgagatgcct ggttataatt aaccccaaca cctgctgccc cccccccccc | 240 |
| aacacctgct gcctgagcct gagcggttac cccaccccgg tgcctgggtc ttaggctctg | 300 |
| tacaccatgg aggagaagct cgctctaaaa ataaccctgt ccctggtgga tcccactacgg | 360 |
| gtctatgctg cccatgtaag gaggcaaggc ctggggacac ccgagatgcc tggttataat | 420 |

| | | |
|---|---|---|
| taaccccaac acctgctgcc cccccccccc caacacctgc tgcctgagcc tgagcggtta | 480 | |
| ccccaccccg gtgcctgggt cttaggctct gtacaccatg gaggagaagc tcgctctaaa | 540 | |
| aataaccctg tccctggtgg accactacgg gtctaggctg cccatgtaag gaggcaaggc | 600 | |
| ctggggacac ccgagatgcc tggttataat taaccccaac acctgctgcc cccccccccc | 660 | |
| aacacctgct gcctgagcct gagcggttac cccaccccgg tgcctgggtc ttaggctctg | 720 | |
| tacaccatgg aggagaagct cgctctaaaa ataaccctgt ccctggtcct ccctggggac | 780 | |
| agcccctcct ggctagtcac accctgtagg ctcctctata acccagggg gcacaggggc | 840 | |
| tgcccccggg tcacctgcag aagttggtcg tgaggcactg ggcaggtaag tatcaaggtt | 900 | |
| acaagacagg tttaaggaga ccaatagaaa ctgggcttgt cgagacagag aagactcttg | 960 | |
| cgtttctgat aggcacctat tggtcttact gacatccact ttgccttct ctccacaggt | 1020 | |
| gtccactccc agttcaatta cagcgcgtgg taccaccatg gcagcagcag ccgccgcagc | 1080 | |
| cgccgagcag cagtcaagca atggaccagt gaaaaatca atgagagaaa aagccgtcga | 1140 | |
| gaggagatca gtgaataagg agcacaacag caatttcaaa gccggctaca tcccctattga | 1200 | |
| cgaagatcgc ctgcataaga caggcctgag ggggcgcaaa ggaaacctgg caatctgcgt | 1260 | |
| catcattctg ctgtttatcc tggccgtgat taatctgatc attactctgg tgatttgggc | 1320 | |
| tgtcatccgc attgggccaa acgggtgtga ctctatggag ttccacgaaa gtggcctgct | 1380 | |
| gcgatttaag caggtgtccg atatggggggt catccatcca ctgtacaaat ctactgtcgg | 1440 | |
| cgggcggaga acgagaatc tggtgatcac cgggaacaat cagcccattg tgttccagca | 1500 | |
| gggaaccaca aagctgtctg tggaaaacaa taaaacatca atcactagcg acattggcat | 1560 | |
| gcagttcttt gatccccgga cccagaatat cctgttcagt accgactatg agacacacga | 1620 | |
| atttcatctg ccttccgggg tgaagtctct gaacgtccag aaagccagca ctgagagaat | 1680 | |
| caccagtaac gctacatcag acctgaatat caaggtggat ggacgagcta ttgtccgggg | 1740 | |
| aaatgagggc gtgttcatca tgggcaagac aattgaattt cacatgggag caacatgga | 1800 | |
| gctgaaagca gaaaacagca tcattctgaa tgggagcgtg atggtctcca ctaccagact | 1860 | |
| gcccagctcc tctagtggag accagctggg gtccggagat tgggtcaggt ataagctgtg | 1920 | |
| catgtgtgcc gatggcaccc tgtttaaagt gcaggtcacc agccagaata tgggatgtca | 1980 | |
| gattagcgat aacccttgtg ggaatactca ttaaaagctt ggccgcaata aaagatcttt | 2040 | |
| attttcatta gatctgtgtg ttggttttt tgtgtgtcctg cagggggcgcg cctctagagc | 2100 | |
| atggctacgt agataagtag catggcgggt taatcattaa ctacaaggaa ccccctagtga | 2160 | |
| tggagttggc cactccctct ctgcgcgctc gctcgctcac tgaggccggg cgaccaaagg | 2220 | |
| tcgcccgacg cccgggcttt gccc | 2244 | |

<210> SEQ ID NO 6
<211> LENGTH: 714
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: tMCK promoter

<400> SEQUENCE: 6

| | | |
|---|---|---|
| ccactacggg tctaggctgc ccatgtaagg aggcaaggcc tggggacacc cgagatgcct | 60 | |
| ggttataatt aaccccaaca cctgctgccc cccccccc aacacctgct gcctgagcct | 120 | |

```
gagcggttac cccaccccgg tgcctgggtc ttaggctctg tacaccatgg aggagaagct    180
cgctctaaaa ataaccctgt ccctggtgga tccactacgg gtctatgctg cccatgtaag    240
gaggcaaggc ctggggacac ccgagatgcc tggttataat taaccccaac acctgctgcc    300
cccccccccc caacacctgc tgcctgagcc tgagcggtta ccccaccccg gtgcctgggt    360
cttaggctct gtacaccatg gaggagaagc tcgctctaaa ataaccctgt ccctggtgg     420 accactacgg gtctaggctg cccatgtaag gaggcaaggc ctggggacac ccgagatgcc    480
tggttataat taaccccaac acctgctgcc cccccccccc aacacctgct gcctgagcct    540
gagcggttac cccaccccgg tgcctgggtc ttaggctctg tacaccatgg aggagaagct    600
cgctctaaaa ataaccctgt ccctggtcct ccctggggac agccctcct ggctagtcac     660 accctgtagg ctcctctata taacccaggg gcacaggggc tgccccgggg tcac          714

<210> SEQ ID NO 7
<211> LENGTH: 296
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: miR29c

<400> SEQUENCE: 7
ggccggcctg tttgaatgag gcttcagtac tttacagaat cgttgcctgc acatcttgga     60
aacacttgct gggattactt cttcaggtta acccaacaga aggctcgaga aggtatattg    120
ctgttgacag tgagcgcaac cgatttcaaa tggtgctaga gtgaagccac agatgtctag    180
caccatttga aatcggttat gcctactgcc tcggaattca aggggctact ttaggagcaa    240
ttatcttgtt tactaaaact gaataccttg ctatctcttt gatacattgg ccggcc        296

<210> SEQ ID NO 8
<211> LENGTH: 3384
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: pAAV.CMV.Mir29C

<400> SEQUENCE: 8
cagcagctgc gcgctcgctc gctcactgag gccgcccggg caaagcccgg gcgtcgggcg     60
acctttggtc gcccggcctc agtgagcgag cgagcgcgca gagagggagt ggggttaaac    120
tcgttacata acttacggta aatggcccgc ctggctgacc gcccaacgac ccccgcccat    180
tgacgtcaat aatgacgtat gttcccatag taacgccaat agggactttc cattgacgtc    240
aatgggtgga gtatttacgg taaactgccc acttggcagt acatcaagtg tatcatatgc    300
caagtacgcc ccctattgac gtcaatgacg gtaaatggcc cgcctggcat tatgcccagt    360
acatgacctt atgggacttt cctacttggc agtacatcta cgtattagtc atcgctatta    420
ccatggtgat gcggttttgg cagtacatca atgggcgtgg atagcggttt gactcacggg    480
gatttccaag tctccacccc attgacgtca atgggagttt gttttggcac caaaatcaac    540
gggactttcc aaaatgtcgt aacaactccg ccccattgac gcaaatgggc ggtaggcgtg    600
tacggtggga ggtctatata agcagagctc gtttagtgaa ccgtcagatc gcctggagac    660
gccatccacg ctgttttgac ctccatagaa gacaccggga ccgatccagc ctccggactc    720
```

```
tagaggatcc ggtactcgag gaactgaaaa accagaaagt taactggtaa gtttagtctt      780
tttgtctttt atttcaggtc ccggatccgg tggtggtgca aatcaaagaa ctgctcctca      840
gtggatgttg cctttacttc taggcctgta cggaagtgtt acttctgctc taaaagctgc      900
ggaattgtac ccggggccga tccaccggtc tttttcgcaa cgggtttgcc gccagaacac      960
aggtaagtgc cgtgtgtggt tcccgcgggc ggcgacgggg cccgtgcgtc ccagcgcaca     1020
tgttcggcga ggcggggcct gcgagcgcgg ccaccgagaa tcggacgggg gtagtctcaa     1080
gctggccggc ctgtttgaat gaggcttcag tactttacag aatcgttgcc tgcacatctt     1140
ggaaacactt gctgggatta cttcttcagg ttaacccaac agaaggctcg agaaggtata     1200
ttgctgttga cagtgagcgc aaccgatttc aaatggtgct agagtgaagc cacagatgtc     1260
tagcaccatt tgaaatcggt tatgcctact gcctcggaat tcaagggct acttaggag      1320 caattatctt gtttactaaa actgaatacc ttgctatctc tttgatacat tggccggcct     1380
gctctggtgc ctggcctcgc gccgccgtgt atcgccccgc cctgggcggc aaggctggcc     1440
cggtcggcac cagttgcgtg agcggaaaga tggccgcttc ccggccctgc tgcagggagc     1500
tcaaaatgga ggacgcggcg ctcgggagag cgggcgggtg agtcacccac acaaaggaaa     1560
agggcctttc cgtcctcagc cgtcgcttca tgtgactcca cggagtaccg ggcgccgtcc     1620
aggcacctcg attagttctc gagcttttgg agtacgtcgt ctttaggttg ggggagggg      1680 ttttatgcga tggagtttcc ccacactgag tgggtggaga ctgaagttag gccagcttgg     1740
cacttgatgt aattctcctt ggaatttgcc ctttttgagt ttggatcttg gttcattctc     1800
aagcctcaga cagtggttca agtttttttt cttccatttc aggtgtcgtg aaaagctagc     1860
gctaccggac tcagatctcg agctcaagct gcggggatcc agacatgata agatacattg     1920
atgagtttgg acaaaccaca actagaatgc agtgaaaaaa atgctttatt tgtgaaattt     1980
gtgatgctat tgctttattt gtaaccatta taagctgcaa taaacaagtt aacaacaaca     2040
attgcattca ttttatgttt caggttcagg gggaggtgtg ggaggttttt tcactagtag     2100
catggctacg tagataagta gcatggcggg ttaatcatta actacaagga acccctagtg     2160
atggagttgg ccactccctc tctgcgcgct cgctcgctca ctgaggccgg gcgaccaaag     2220
gtcgcccgac gcccgggctt tgcccgggcg gcctcagtga gcgagcgagc gcgccagctg     2280
gcgtaatagc gaagaggccc gcaccgatcg cccttcccaa cagttgcgca gcctgaatgg     2340
cgaatggaat tccagacgat tgagcgtcaa aatgtaggta tttccatgag cgttttcct     2400 gttgcaatgg ctggcggtaa tattgttctg gatattacca gcaaggccga tagtttgagt     2460
tcttctactc aggcaagtga tgttattact aatcaaagaa gtattgcgac aacggttaat     2520
ttgcgtgatg gacagactct tttactcggt ggcctcactg attataaaaa cacttctcag     2580
gattctggcg taccgttcct gtctaaaatc cctttaatcg gcctcctgtt tagctcccgc     2640
tctgattcta acgaggaaag cacgttatac gtgctcgtca aagcaaccat agtacgcgcc     2700
ctgtagcggc gcattaagcg cggcgggtgt ggtggttacg cgcagcgtga ccgctacact     2760
tgccagcgcc ctagcgcccg ctcctttcgc tttcttccct cctttctcg ccacgttcgc      2820 cggctttccc cgtcaagctc taaatcgggg ctccctttta gggttccgat ttagtgcttt     2880
acggcacctc gaccccaaaa aacttgatta gggtgatggt tcacgtagtg gccatcgcc      2940 ctgatagacg gttttcgcc ctttgacgtt ggagtccacg ttctttaata gtggactctt      3000
gttccaaact ggaacaacac tcaaccctat ctcggtctat tcttttgatt tataagggat     3060
```

```
tttgccgatt tcggcctatt ggttaaaaaa tgagctgatt taacaaaaat ttaacgcgaa    3120
ttttaacaaa atattaacgt ttacaattta aatatttgct tatacaatct tcctgttttt    3180
ggggcttttc tgattatcaa ccggggtaca tatgattgac atgctagttt tacgattacc    3240
gttcatcgat tctcttgttt gctccagact ctcaggcaat gacctgatag cctttgtaga    3300
gacctctcaa aaatagctac cctctccggc atgaatttat cagctagaac ggttgaatat    3360
catattgatg gtgatttgac tgtc                                            3384

<210> SEQ ID NO 9
<211> LENGTH: 296
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: miR29c

<400> SEQUENCE: 9
ggccggcctg tttgaatgag gcttcagtac tttacagaat cgttgcctgc acatcttgga     60
aacacttgct gggattactt cttcaggtta acccaacaga aggctcgaga aggtatattg    120
ctgttgacag tgagcgcaac cgatttcaaa tggtgctaga gtgaagccac agatgtctag    180
caccatttga aatcggttat gcctactgcc tcggaattca aggggctact ttaggagcaa    240
ttatcttgtt tactaaaact gaatacctty ctatctcttt gatacattgg ccggcc        296

<210> SEQ ID NO 10
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK forward primer

<400> SEQUENCE: 10
acccgagatg cctggttata att                                             23

<210> SEQ ID NO 11
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK reverse primer

<400> SEQUENCE: 11
tccatggtgt acagagccta agac                                            24

<210> SEQ ID NO 12
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK probe
<220> FEATURE:
<221> NAME/KEY: misc_feature
<222> LOCATION: (1)..(1)
<223> OTHER INFORMATION: 5' FAM
```

```
<220> FEATURE:
<221> NAME/KEY: misc_feature
<222> LOCATION: (25)..(25)
<223> OTHER INFORMATION: 3' TAMRA

<400> SEQUENCE: 12
ctgctgcctg agcctgagcg gttac                                              25

<210> SEQ ID NO 13
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK intron Forward Primer

<400> SEQUENCE: 13
gtgaggcact gggcaggtaa                                                    20

<210> SEQ ID NO 14
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK intron Reverse Primer

<400> SEQUENCE: 14
acctgtggag agaaaggcaa ag                                                 22

<210> SEQ ID NO 15
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: tMCK intron Probe
<220> FEATURE:
<221> NAME/KEY: misc_feature
<222> LOCATION: (1)..(1)
<223> OTHER INFORMATION: 5' 6FAM
<220> FEATURE:
<221> NAME/KEY: misc_feature
<222> LOCATION: (39)..(39)
<223> OTHER INFORMATION: 3' TAMRA

<400> SEQUENCE: 15
atcaaggtta caagacaggt ttaaggagac caatagaaa                               39

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ccaacacctg ctgcctctaa a                                                  21

<210> SEQ ID NO 17
<211> LENGTH: 19
<212> TYPE: DNA
<213> ORGANISM: Artificial Sequence
```

```
<220> FEATURE:
<223> OTHER INFORMATION: Primer
<220> FEATURE:
<221> NAME/KEY: misc_feature
<223> OTHER INFORMATION: MHCK7 reverse primer

<400> SEQUENCE: 17
gtcccccaca gccttgttc                                                      19

<210> SEQ ID NO 18
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: MHCK7 probe
<220> FEATURE:
<221> NAME/KEY: misc_feature
<222> LOCATION: (1)..(1)
<223> OTHER INFORMATION: 5' FAM
<220> FEATURE:
<221> NAME/KEY: misc_feature
<222> LOCATION: (9)..(9)
<223> OTHER INFORMATION: Zen
<220> FEATURE:
<221> NAME/KEY: misc_feature
<222> LOCATION: (23)..(23)
<223> OTHER INFORMATION: 3IABKFQ

<400> SEQUENCE: 18
tggatcccct gcatgcgaag atc                                                 23

<210> SEQ ID NO 19
<211> LENGTH: 2303
<212> TYPE: DNA
<213> ORGANISM: Artificial Sequence
<220> FEATURE:
<223> OTHER INFORMATION: Synthetic Polynucleotide

<400> SEQUENCE: 19
ctgcgcgctc gctcgctcac tgaggccgcc cgggcaaagc ccgggcgtcg ggcgaccttt          60
ggtcgcccgg cctcagtgag cgagcgagcg cgcagagagg gagtggggtt aaccaattgg        120
cggccgcaag cttgcatgtc taagctagac ccttcagatt aaaaataact gaggtaaggg       180
cctgggtagg ggaggtggtg tgagacgctc ctgtctctcc tctatctgcc catcggccct       240
ttggggagga ggaatgtgcc caaggactaa aaaaggcca tggagccaga ggggcgaggg        300
caacagacct ttcatgggca aaccttgggg ccctgctgtc tagcatgccc cactacgggt       360
ctaggctgcc catgtaagga ggcaaggcct ggggacaccc gagatgcctg gttataatta       420
acccagacat gtggctgccc cccccccccc aacacctgct gcctctaaaa ataaccctgt       480
ccctggtgga tcccctgcat gcgaagatct tcgaacaagg ctgtggggga ctgagggcag       540
gctgtaacag gcttggggc cagggcttat acgtgcctgg gactcccaaa gtattactgt        600
tccatgttcc cggcgaaggg ccagctgtcc cccgccagct agactcagca cttagtttag      660
gaaccagtga gcaagtcagc ccttggggca gcccatacaa ggccatgggg ctgggcaagc      720
tgcacgcctg ggtccggggt gggcacggtg cccgggcaac gagctgaaag ctcatctgct     780
ctcaggggcc cctccctggg gacagcccct cctggctagt cacaccctgt aggctcctct    840
atataaccca ggggcacagg ggctgccctc attctaccac cacctccaca gcacagacag    900
acactcagga gcagccagcg cgcgcgccag gtaagtttag tcttttttgtc ttttattttca  960
```

-continued

```
ggtcccggat ccggtggtgg tgcaaatcaa agaactgctc ctcagtggat gttgccttta   1020
cttctaggcc tgtacggaag tgttacttct gctctaaaag ctgcggaatt gtacccggta   1080
ccaccatggc agcagcagcc gccgcagccg ccgagcagca gtcaagcaat ggaccagtga   1140
aaaaatcaat gagagaaaaa gccgtcgaga ggagatcagt gaataaggag cacaacagca   1200
atttcaaagc cggctacatc cctattgacg aagatcgcct gcataagaca ggcctgaggg   1260
ggcgcaaagg aaacctggca atctgcgtca tcattctgct gtttatcctg gccgtgatta   1320
atctgatcat tactctggtg atttgggctg tcatccgcat tggcccaaac gggtgtgact   1380
ctatggagtt ccacgaaagt ggcctgctgc gatttaagca ggtgtccgat atgggggtca   1440
tccatccact gtacaaatct actgtcggcg ggcggagaaa cgagaatctg gtgatcaccg   1500
ggaacaatca gcccattgtg ttccagcagg gaaccacaaa gctgtctgtg gaaaacaata   1560
aaacatcaat cactagcgac attggcatgc agttctttga tccccggacc cagaatatcc   1620
tgttcagtac cgactatgag acacacgaat ttcatctgcc ttccggggtg aagtctctga   1680
acgtccagaa agccagcact gagagaatca ccagtaacgc tacatcagac ctgaatatca   1740
aggtggatgg acgagctatt gtccggggaa atgagggcgt gttcatcatg ggcaagacaa   1800
ttgaatttca catgggaggc aacatggagc tgaaagcaga aaacagcatc attctgaatg   1860
ggagcgtgat ggtctccact accagactgc ccagctcctc tagtggagac cagctggggt   1920
ccggagattg ggtcaggtat aagctgtgca tgtgtgccga tggcaccctg tttaaagtgc   1980
aggtcaccag ccagaatatg ggatgtcaga ttagcgataa cccttgtggg aatactcatt   2040
aaaagcttgg ccgcaataaa agatctttat tttcattaga tctgtgtgtt ggttttttgt   2100
gtgtcctgca ggggcgcgcc tctagagcat ggctacgtag ataagtagca tggcgggtta   2160
atcattaact acaaggaacc cctagtgatg gagttggcca ctccctctct gcgcgctcgc   2220
tcgctcactg aggccgggcg accaaaggtc gcccgacgcc cgggctttgc ccgggcggcc   2280
tcagtgagcg agcgagcgcg cag                                           2303
```

<210> SEQ ID NO 20
<211> LENGTH: 148
<212> TYPE: DNA
<213> ORGANISM: Artificial Sequence
<220> FEATURE:
<223> OTHER INFORMATION: Synthetic Polynucleotide

<400> SEQUENCE: 20

```
aggtaagttt agtctttttg tcttttattt caggtcccgg atccggtggt ggtgcaaatc     60
aaagaactgc tcctcagtgg atgttgcctt tacttctagg cctgtacgga agtgttactt    120
ctgctctaaa agctgcggaa ttgtaccc                                       148
```

<210> SEQ ID NO 21
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 21

```
ggccgcaata aaagatcttt attttcatta gatctgtgtg ttggtttttt gtg            53
```

<210> SEQ ID NO 22
<211> LENGTH: 110
<212> TYPE: DNA
<213> ORGANISM: Artificial Sequence

```
<220> FEATURE:
<223> OTHER INFORMATION: Synthetic Polynucleotide

<400> SEQUENCE: 22
ctgcgcgctc gctcgctcac tgaggccgcc cgggcaaagc ccgggcgtcg ggcgaccttt    60
ggtcgcccgg cctcagtgag cgagcgagcg cgcagagagg gagtgggtt              110

<210> SEQ ID NO 23
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 23
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag                                                          130

<210> SEQ ID NO 24
<211> LENGTH: 5573
<212> TYPE: DNA
<213> ORGANISM: Artificial Sequence
<220> FEATURE:
<223> OTHER INFORMATION: Synthetic Polynucleotide

<400> SEQUENCE: 24
gcagctgcgc gctcgctcgc tcactgaggc cgcccgggca agcccgggcg tcgggcgac     60 ctttggtcgc ccgcctcag tgagcgagcg agcgcgcaga gagggagtgg ggttaaccaa    120
ttggcggccg caagcttgca tgtctaagct agacccttca gattaaaaat aactgaggta   180
agggcctggg taggggaggt ggtgtgagac gctcctgtct ctcctctatc tgcccatcgg   240 cccttttgggg aggaggaatg tgcccaagga ctaaaaaaag gccatggagc cagaggggcg   300
agggcaacag acctttcatg ggcaaaacctt ggggccctgc tgtctagcat gccccactac   360
gggtctaggc tgcccatgta aggaggcaag gcctggggac acccgagatg cctggttata   420
attaacccag acatgtggct gccccccccc ccccaacacc tgctgcctct aaaaataacc   480
ctgtccctgg tggatcccct gcatgcgaag atcttcgaac aaggctgtgg gggactgagg   540
gcaggctgta acaggcttgg ggccagggc ttatacgtgc ctgggactcc caagtatta    600 ctgttccatg ttcccggcga agggccagct gtcccccgcc agctagactc agcacttagt   660
ttaggaacca gtgagcaagt cagcccttgg ggcagcccat acaaggccat ggggctgggc   720
aagctgcacg cctgggtccg gggtgggcac ggtgcccggg caacgagctg aaagctcatc   780
tgctctcagg ggcccctccc tggggacagc ccctcctggc tagtcacacc ctgtaggctc   840
ctctatataa cccaggggca caggggctgc cctcattcta ccaccacctc cacagcacag   900
acagacactc aggagcagcc agcggcgcgc ccaggtaagt ttagtctttt tgtcttttat   960
ttcaggtccc ggatccggtg gtggtgcaaa tcaaagaact gctcctcagt ggatgttgcc  1020
tttacttcta ggcctgtacg gaagtgttac ttctgctcta aaagctgcgg aattgtaccc  1080
ggtaccacca tggcagcagc agccgccgca gccgccgagc agcagtcaag caatggacca  1140
gtgaaaaaat caatgagaga aaaagccgtc gagaggagat cagtgaataa ggagcacaac  1200
agcaatttca agccggcta catccctatt gacgaagatc gcctgcataa gacaggcctg  1260 aggggggcgca aggaaaacct ggcaatctgc gtcatcattc tgctgtttat cctggccgtg  1320
```

```
attaatctga tcattactct ggtgatttgg gctgtcatcc gcattggccc aaacgggtgt    1380
gactctatgg agttccacga aagtggcctg ctgcgattta agcaggtgtc cgatatgggg    1440
gtcatccatc cactgtacaa atctactgtc ggcgggcgga gaaacgagaa tctggtgatc    1500
accgggaaca atcagcccat tgtgttccag cagggaacca caaagctgtc tgtggaaaac    1560
aataaaacat caatcactag cgacattggc atgcagttct ttgatcccg gacccagaat    1620 atcctgttca gtaccgacta tgagacacac gaatttcatc tgccttccgg ggtgaagtct    1680
ctgaacgtcc agaaagccag cactgagaga atcaccagta acgctacatc agacctgaat    1740
atcaaggtgg atggacgagc tattgtccgg ggaaatgagg gcgtgttcat catgggcaag    1800
acaattgaat ttcacatggg aggcaacatg gagctgaaag cagaaaacag catcattctg    1860
aatgggagcg tgatggtctc cactaccaga ctgcccagct cctctagtgg agaccagctg    1920
gggtccggag attgggtcag gtataagctg tgcatgtgtg ccgatggcac cctgttaaa    1980 gtgcaggtca ccagccagaa tatgggatgt cagattagcg ataaccctg tgggaatact    2040 cattaaaagc ttggccgcaa taaagatct ttatttcat tagatctgtg tgttggttt    2100 ttgtgtgtcc tgcagggcg cgcctctaga gcatggctac gtagataagt agcatggcgg    2160
gttaatcatt aactacaagg aaccctagt gatggagttg ccactccct ctctgcgcgc    2220 tcgctcgctc actgaggccg ggcgaccaaa ggtcgccga cgcccgggct tgcccgggc    2280 ggcctcagtg agcgagcgag cgcgcagctg gcgtaatagc gaagaggccc gcaccgatcg    2340
cccttcccaa cagttgcgca gcctgaatgg cgaatggcga ttccgttgca atggctggcg    2400
gtaatattgt tctggatatt accagcaagg ccgatagttt gagttcttct actcaggcaa    2460
gtgatgttat tactaatcaa agaagtattg cgacaacggt taatttgcgt gatggacaga    2520
ctcttttact cggtggcctc actgattata aaaacacttc tcaggattct ggcgtaccgt    2580
tcctgtctaa atccctttta atcggcctcc tgtttagctc ccgctctgat tctaacgagg    2640
aaagcacgtt atacgtgctc gtcaaagcaa ccatagtacg cgccctgtag cggcgcatta    2700
agcgcggcgg gtgtggtggt tacgcgcagc gtgaccgcta cacttgccag cgccctagcg    2760
cccgctcctt tcgctttctt cccttccttt ctcgccacgt tcgccatctt caaatatgta    2820
tccgctcatg agacaataac cctgataaat gcttcaataa tattgaaaaa ggaagagtcc    2880
tgaggcggaa agaaccagct gtggaatgtg tgtcagttag ggtgtggaaa gtccccaggc    2940
tccccagcag gcagaagtat gcaaagcatg catctcaatt agtcagcaac caggtgtgga    3000
aagtccccag gctccccagc aggcagaagt atgcaaagca tgcatctcaa ttagtcagca    3060
accatagtcc cgcccctaac tccgcccat ggctgactaa ttttttttat ttatgcagag    3120
gccgaggccg cctcggcctc tgagctattc cagaagtagt gaggaggctt ttttggaggc    3180
ctaggctttt gcaaagatcg atcaagagac aggatgagga tcgtttcgca tgattgaaca    3240
agatggattg cacgcaggtt ctccggccgc ttgggtggag aggctattcg gctatgactg    3300
ggcacaacag acaatcggct gctctgatgc cgccgtgttc cggctgtcag cgcaggggcg    3360
cccggttctt tttgtcaaga ccgacctgtc cggtgccctg aatgaactgc aagacgaggc    3420
agcgcggcta tcgtggctgg ccacgacggg cgttccttgc gcagctgtgc tcgacgttgt    3480
cactgaagcg ggaagggact ggctgctatt gggcgaagtg ccggggcagg atctcctgtc    3540
atctcacctt gctcctgccg agaaagtatc catcatggct gatgcaatgc ggcggctgca    3600
tacgcttgat ccggctacct gcccattcga ccaccaagcg aaacatcgca tcgagcgagc    3660
acgtactcgg atggaagccg gtcttgtcga tcaggatgat ctggacgaag agcatcaggg    3720
```

```
gctcgcgcca gccgaactgt tcgccaggct caaggcgagc atgcccgacg gcgaggatct    3780
cgtcgtgacc catggcgatg cctgcttgcc gaatatcatg gtggaaaatg gccgcttttc    3840
tggattcatc gactgtggcc ggctgggtgt ggcggaccgc tatcaggaca tagcgttggc    3900
tacccgtgat attgctgaag agcttggcgg cgaatgggct gaccgcttcc tcgtgcttta    3960
cggtatcgcc gctcccgatt cgcagcgcat cgccttctat cgccttcttg acgagttctt    4020
ctgagcggga ctctggggtt cgaaatgacc gaccaagcga cgcccaacct gccatcacga    4080
gatttcgatt ccaccgccgc cttctatgaa aggttgggct tcggaatcgt tttccgggac    4140
gccggctgga tgatcctcca gcgcggggat ctcatgctgg agttcttcgc ccaccctagg    4200
gggaggctaa ctgaaacacg gaaggagaca ataccggaag gaacccgcgc tatgacggca    4260
ataaaaagac agaataaaaa cgttgcgcaa actattaact ggcgaactac ttactctagc    4320
ttcccggcaa caattaatag actggatgga ggcggataaa gttgcaggac cacttctgcg    4380
ctcggccctt ccggctggct ggtttattgc tgataaatct ggagccggtg agcgtgggtc    4440
tcgcggtatc attgcagcac tggggccaga tggtaagccc tcccgtatcg tagttatcta    4500
cacgacgggg agtcaggcaa ctatggatga acgaaataga cagatcgctg agataggtgc    4560
ctcactgatt aagcattggt aactgtcaga ccaagtttac tcatatatac tttagattga    4620
tttaaaactt cattttaat ttaaaaggat ctaggtgaag atccttttg ataatctcat    4680 gaccaaaatc ccttaacgtg agttttcgtt ccactgagcg tcagacccg tagaaaagat    4740 caaaggatct tcttgagatc ctttttttct gcgcgtaatc tgctgcttgc aaacaaaaaa    4800
accaccgcta ccagcggtgg tttgtttgcc ggatcaagag ctaccaactc ttttccgaa    4860 ggtaactggc ttcagcagag cgcagatacc aaatactgtt cttctagtgt agccgtagtt    4920
aggccaccac ttcaagaact ctgtagcacc gcctacatac ctcgctctgc taatcctgtt    4980
accagtggct gctgccagtg gcgataagtc gtgtcttacc gggttggact caagacgata    5040
gttaccggat aaggcgcagc ggtcgggctg aacgggggt tcgtgcacac agcccagctt    5100
ggagcgaacg acctacaccg aactgagata cctacagcgt gagctatgag aaagcgccac    5160
gcttcccgaa gggagaaagg cggacaggta tccggtaagc ggcagggtcg gaacaggaga    5220
gcgcacgagg gagcttccag ggggaaacgc ctggtatctt tatagtcctg tcgggtttcg    5280
ccacctctga cttgagcgtc gatttttgtg atgctcgtca gggggcgga gcctatgaa    5340 aaacgccagc aacgcggcct ttttacggtt cctggccttt tgctggcctt ttgctcacat    5400
gttctttcct gcgttatccc ctgattctgt ggataaccgt attaccgcct ttgagtgagc    5460
tgataccgct cgccgcagcc gaacgaccga gcgcagcgag tcagtgagcg aggaagcgga    5520
agagcgccca atacgcaaac cgcctctccc cgcgcgttgg ccgattcatt aat    5573
```